United States Patent
Yam et al.

(10) Patent No.: US 10,822,414 B2
(45) Date of Patent: Nov. 3, 2020

(54) ANTI-PD-1 ANTIBODIES, COMPOSITIONS COMPRISING ANTI-PD-1 ANTIBODIES AND METHODS OF USING ANTI-PD-1 ANTIBODIES

(71) Applicant: SUTRO BIOPHARMA, INC., South San Francisco, CA (US)

(72) Inventors: Alice Yam, Tiburon, CA (US); Ryan Stafford, Emeryville, CA (US); Aaron Sato, Burlingame, CA (US); John Lee, San Francisco, CA (US); Avinash Gill, Emeryville, CA (US); Junhao Yang, Palo Alto, CA (US); Heather Stephenson, San Jose, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 246 days.

(21) Appl. No.: 15/525,943

(22) PCT Filed: Nov. 10, 2015

(86) PCT No.: PCT/US2015/060033
§ 371 (c)(1),
(2) Date: May 10, 2017

(87) PCT Pub. No.: WO2016/077397
PCT Pub. Date: May 19, 2016

(65) Prior Publication Data
US 2018/0142022 A1 May 24, 2018

Related U.S. Application Data

(60) Provisional application No. 62/078,115, filed on Nov. 11, 2014.

(51) Int. Cl.
*C07K 16/28* (2006.01)
*A61P 37/00* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *A61P 37/00* (2018.01); *A61K 2039/505* (2013.01); *C07K 2317/24* (2013.01); *C07K 2317/33* (2013.01); *C07K 2317/34* (2013.01); *C07K 2317/41* (2013.01); *C07K 2317/622* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS 8,735,553 B1  5/2014  Kang et al.

FOREIGN PATENT DOCUMENTS

| AU | 2014 201 367 A1 | 4/2014 | |
| WO | WO 2004/056875 A1 | 7/2001 | |
| WO | WO 2006/121168 | * 11/2006 | ............. C12N 15/09 |
| WO | WO 2006/121168 A1 | 11/2006 | |
| WO | WO 2010/036959 A2 | 4/2010 | |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Hamid et al., "Safety and Tumor Responses with Lambrolizumab (Anti-PD-1) in Melanoma", New England Journal of Medicine, Jul. 11, 2013, vol. 369, No. 2, pp. 134-144, XP055182016.
Ohaegbulam et al., "Human cancer immunotherapy with antibodies to the PD-1 and PD-L1 pathway", Trends in Molecular Medicine, vol. 21, No. 1, Oct. 30, 2014, pp. 24-33, XP055249717.
Latchman et al., "PD-L2 is a second ligand for PD-1 and inhibits T cell activation", Nat. Immunol., vol. 2 No. 3, Mar. 2001, pp. 261-268.
Freeman et al., "Engagement of the PD-1 Immunoinhibitory Receptor by a Novel B7 Family Member Leads to Negative Regulation of Lymphocyte Activation", J. Exp. Med., vol. 192, No. 7, Oct. 2, 2000, pp. 1027-1034.
Blank et al., "Contribution of the PD-L1/PD-1 pathway to T-cell exhaustion: an update on implications for chronic infections and tumor evasion", Cancer Immunol Immunother, (2007) 56:739-745.
Dai et al., "The PD-1/PD-Ls pathway and autoimmune diseases", Cellular Immunology 290, (2014), pp. 72-79.
Ishida et al., "Induced expression of PD-1, a novel member of the immunoglobulingene superfamily, upon programmed cell death", The EMBO Journal, (1992), vol. 11, No. 11, pp. 3887-3895.
Ribas et al., "The Future of Cancer Therapy: Selecting Patients Likely to Respond to PD1/L1 Blockade", Clin Cancer Res; Oct. 1, 2014, vol. 20, No. 19, pp. 4982-4984.
Day et al., "PD-1 expression on HIV-specific T cells is associated with T-cell exhaustion and disease Progression", NATURE, vol. 443, Sep. 21, 2006, pp. 350-354.

* cited by examiner

Primary Examiner — Nelson B Moseley, II
(74) Attorney, Agent, or Firm — Squire Patton Boggs (US) LLP

(57) ABSTRACT

Provided herein are antibodies that selectively bind to PD-1 and its isoforms and homologs, and compositions comprising the antibodies. Also provided are methods of using the antibodies, such as therapeutic and diagnostic methods.

35 Claims, 5 Drawing Sheets
Specification includes a Sequence Listing.

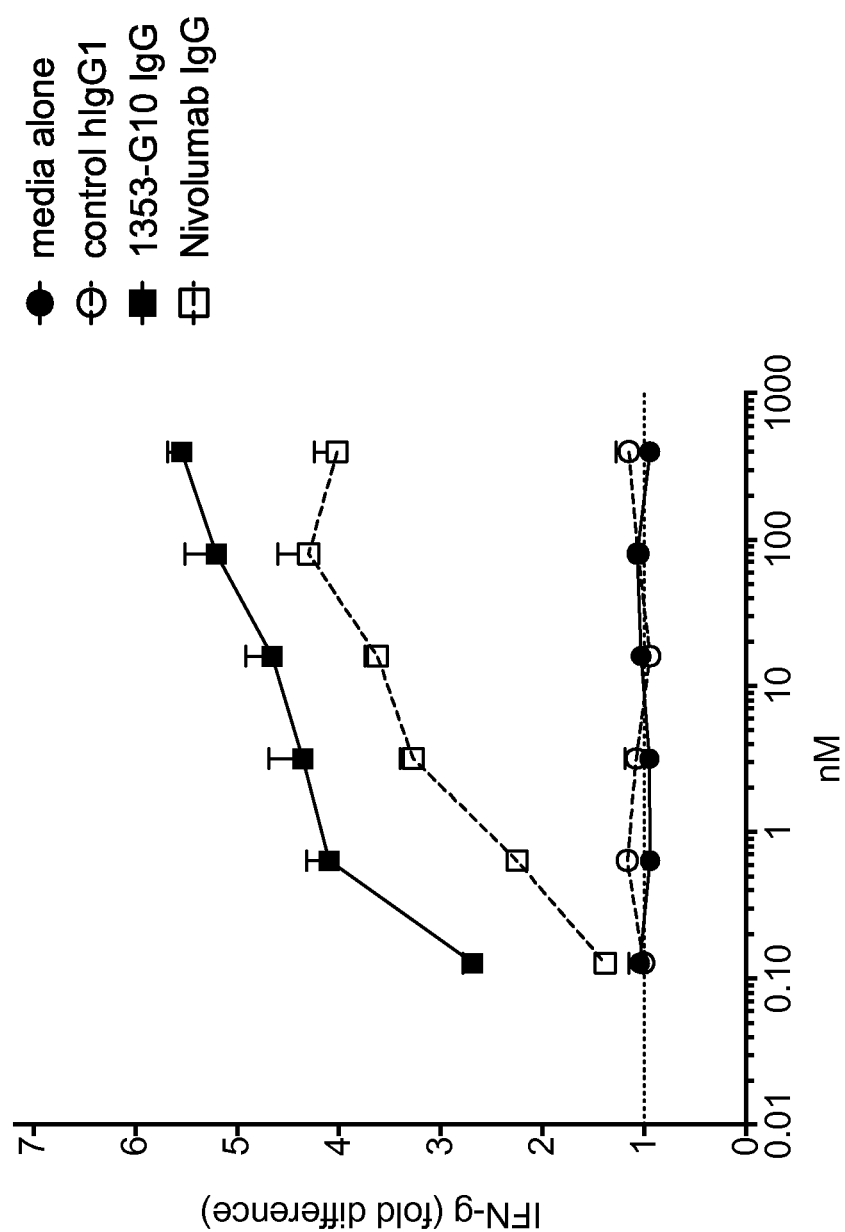

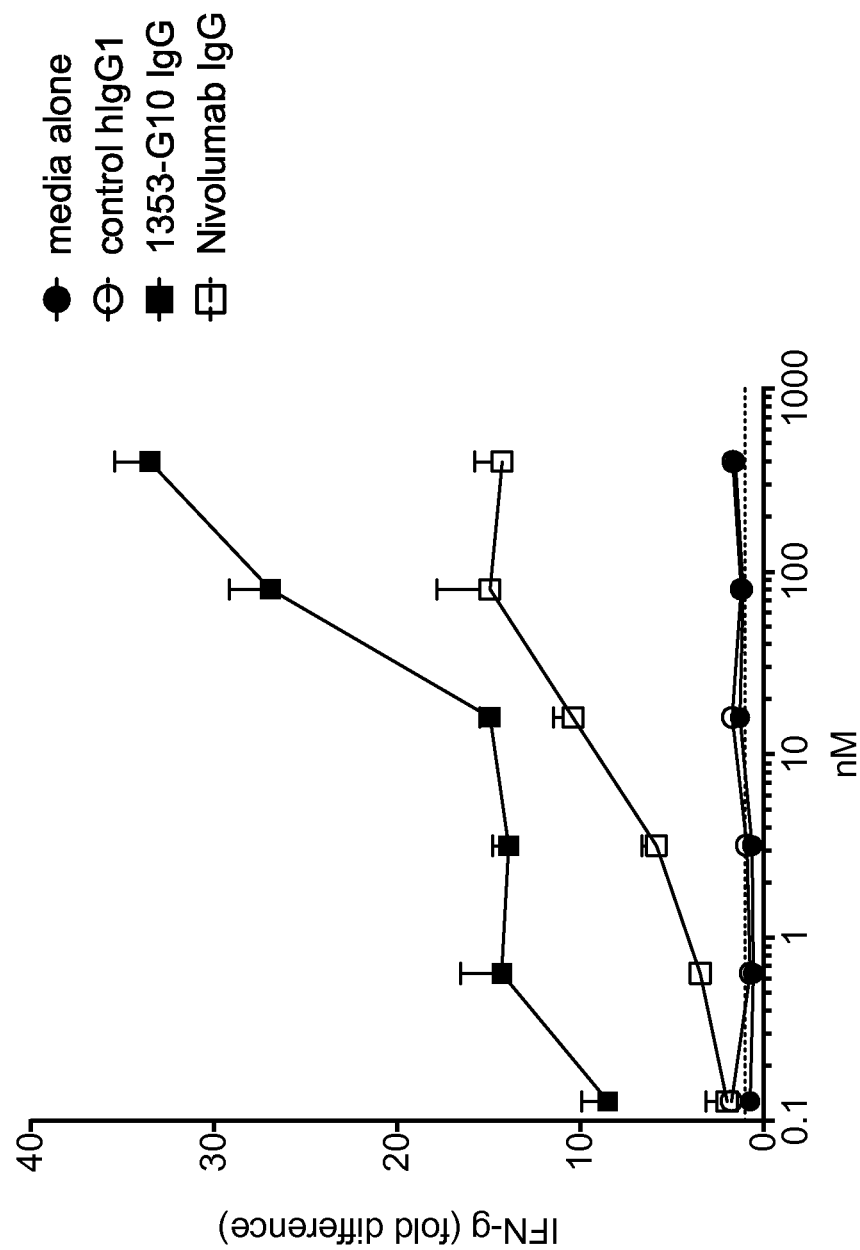
FIG. 4 MLR Assay

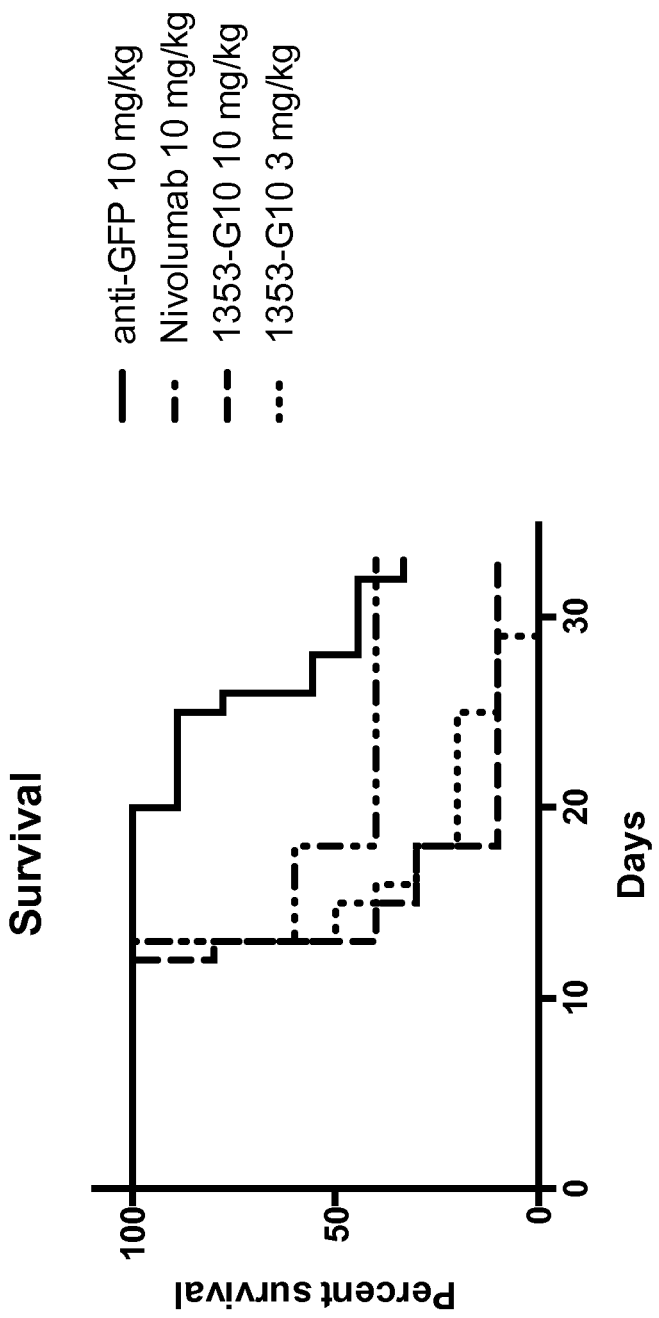
FIG. 5 GVHD Response

SEQUENCE LISTING

```
<160> NUMBER OF SEQ ID NOS: 331

<210> SEQ ID NO 1
<211> LENGTH: 288
<212> TYPE: PRT
<213> ORGANISM: Homo sapiens
<220> FEATURE:
<221> NAME/KEY: misc_feature
<222> LOCATION: (1)..(288)
<223> OTHER INFORMATION: Human PD-1

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
```

-continued

```
                180                 185                 190
Ser Arg Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 12
<212> TYPE: PRT
<213> ORGANISM: Artificial Sequence
<220> FEATURE:
<223> OTHER INFORMATION: Synthetic: PD1-17, CDR-H1

<400> SEQUENCE: 2

Ser Gly Gly Ser Ile Arg Ser Thr Arg Trp Trp Ser
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic: PD1-28, CDR-H1

<400> SEQUENCE: 3

Ser Tyr Gly Ile Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic: PD1-33, CDR-H1

<400> SEQUENCE: 4

Ser Tyr Tyr Ile His
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic: PD1-35, CDR-H1

<400> SEQUENCE: 5

Ser Gly Ala Tyr Tyr Trp Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic: PD1-F2, CDR-H1
```

```
<400> SEQUENCE: 6

Ser Ser Tyr Trp Met Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic: 10B4, CDR-H1

<400> SEQUENCE: 7

Gly Tyr Ile Phe Ser Ser Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic: 1353-A09, CDR-H1

<400> SEQUENCE: 8

Gly Tyr Arg Phe Thr Trp Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic: 1353-C07, CDR-H1

<400> SEQUENCE: 9

Gly Tyr Arg Phe Ser Thr Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic: 1353-E07, CDR-H1

<400> SEQUENCE: 10

Gly Tyr Arg Phe Glu Thr Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic: 1353-F09, CDR-H1

<400> SEQUENCE: 11

Gly Tyr Arg Phe Arg Gln Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic: 1353-G08, CDR-H1
```

```
<400> SEQUENCE: 12

Gly Tyr Arg Phe Thr Arg Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic: 1353-G10, CDR-H1

<400> SEQUENCE: 13

Gly Tyr Arg Phe Pro His Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic: 1353-H08, CDR-H1

<400> SEQUENCE: 14

Gly Tyr Arg Phe Thr Arg Gln
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic: 1353-H09, CDR-H1

<400> SEQUENCE: 15

Gly Tyr Arg Phe Pro His Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic: 1B10, CDR-H1

<400> SEQUENCE: 16

Gly His Ser Ile Thr Ser Asp Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic: 1E9, CDR-H1

<400> SEQUENCE: 17

Gly Phe Thr Phe Ser Thr Phe
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic: 4B10, CDR-H1

<400> SEQUENCE: 18
```

Gly Phe Thr Phe Ser Thr Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic: h1E9-1, CDR-H1

<400> SEQUENCE: 19

Gly Phe Thr Phe Ser Thr Phe
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic: h1E9-2, CDR-H1

<400> SEQUENCE: 20

Gly Phe Thr Phe Ser Thr Phe
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic: h1E9-4, CDR-H1

<400> SEQUENCE: 21

Gly Phe Thr Phe Ser Thr Phe
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic: h1E9-5, CDR-H1

<400> SEQUENCE: 22

Gly Phe Thr Phe Ser Thr Phe
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic: h4B10-1, CDR-H1

<400> SEQUENCE: 23

Gly Phe Thr Phe Ser Thr Tyr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic: h4B10-2, CDR-H1

<400> SEQUENCE: 24

```
Gly Phe Thr Phe Ser Thr Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic: h4B10-3, CDR-H1

<400> SEQUENCE: 25

Gly Phe Thr Phe Ser Thr Tyr
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic: PD1-17, CDR-H1

<400> SEQUENCE: 26

Gly Gly Ser Ile Gly Ser Gly Gly Ser Ile Arg Ser Thr Arg
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic: PD1-28, CDR-H1

<400> SEQUENCE: 27

Gly Tyr Arg Phe Thr Ser Tyr
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic: PD1-33, CDR-H1

<400> SEQUENCE: 28

Gly Tyr Thr Leu Thr Ser Tyr
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic: PD1-35, CDR-H1

<400> SEQUENCE: 29

Gly Gly Ser Ile Ser Ser Gly Ala Tyr
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic: PD1-F2, CDR-H1

<400> SEQUENCE: 30

Gly Phe Thr Phe Ser Ser Tyr Trp Cys Asp
```

```
1               5              10
```

<210> SEQ ID NO 31
<211> LENGTH: 5
<212> TYPE: PRT
<213> ORGANISM: Artificial Sequence
<220> FEATURE:
<223> OTHER INFORMATION: Synthetic: 10B4, CDR-H1

<400> SEQUENCE: 31

```
Ser Tyr Trp Ile Gly
1               5
```

<210> SEQ ID NO 32
<211> LENGTH: 5
<212> TYPE: PRT
<213> ORGANISM: Artificial Sequence
<220> FEATURE:
<223> OTHER INFORMATION: Synthetic: 1353-A09, CDR-H1

<400> SEQUENCE: 32

```
Trp Tyr Gly Ile Ser
1               5
```

<210> SEQ ID NO 33
<211> LENGTH: 5
<212> TYPE: PRT
<213> ORGANISM: Artificial Sequence
<220> FEATURE:
<223> OTHER INFORMATION: Synthetic: 1353-C07, CDR-H1

<400> SEQUENCE: 33

```
Thr Phe Gly Ile Ser
1               5
```

<210> SEQ ID NO 34
<211> LENGTH: 5
<212> TYPE: PRT
<213> ORGANISM: Artificial Sequence
<220> FEATURE:
<223> OTHER INFORMATION: Synthetic: 1353-E07, CDR-H1

<400> SEQUENCE: 34

```
Thr Tyr Gly Ile Ser
1               5
```

<210> SEQ ID NO 35
<211> LENGTH: 5
<212> TYPE: PRT
<213> ORGANISM: Artificial Sequence
<220> FEATURE:
<223> OTHER INFORMATION: Synthetic: 1353-F09, CDR-H1

<400> SEQUENCE: 35

```
Gln Tyr Gly Ile Ser
1               5
```

<210> SEQ ID NO 36
<211> LENGTH: 5
<212> TYPE: PRT
<213> ORGANISM: Artificial Sequence
<220> FEATURE:
<223> OTHER INFORMATION: Synthetic: 1353-G08, CDR-H1

<400> SEQUENCE: 36

```
Arg Tyr Gly Ile Ser
1               5
```

```
<210> SEQ ID NO 37
<211> LENGTH: 5
<212> TYPE: PRT
<213> ORGANISM: Artificial Sequence
<220> FEATURE:
<223> OTHER INFORMATION: Synthetic: 1353-G10, CDR-H1

<400> SEQUENCE: 37

His Tyr Gly Ile Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic: 1353-H08, CDR-H1

<400> SEQUENCE: 38

Arg Gln Gly Ile Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic: 1353-H09, CDR-H1

<400> SEQUENCE: 39

His Tyr Gly Ile Ser
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic: 1B10, CDR-H1

<400> SEQUENCE: 40

Ser Asp Tyr Ala Trp Asn
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic: 1E9, CDR-H1

<400> SEQUENCE: 41

Thr Phe Gly Met Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic: 4B10, CDR-H1

<400> SEQUENCE: 42

Thr Tyr Gly Met Ser
1               5
```

<210> SEQ ID NO 43
<211> LENGTH: 5
<212> TYPE: PRT
<213> ORGANISM: Artificial Sequence
<220> FEATURE:
<223> OTHER INFORMATION: Synthetic: h1E9-1, CDR-H1

<400> SEQUENCE: 43

Thr Phe Gly Met Ser
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic: h1E9-2, CDR-H1

<400> SEQUENCE: 44

Thr Phe Gly Met Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic: h1E9-4, CDR-H1

<400> SEQUENCE: 45

Thr Phe Gly Met Ser
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic: h1E9-5, CDR-H1

<400> SEQUENCE: 46

Thr Phe Gly Met Ser
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic: h4B10-1, CDR-H1

<400> SEQUENCE: 47

Thr Tyr Gly Met Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic: h4B10-2, CDR-H1

<400> SEQUENCE: 48

Thr Tyr Gly Met Ser
1               5

```
<210> SEQ ID NO 49
<211> LENGTH: 5
<212> TYPE: PRT
<213> ORGANISM: Artificial Sequence
<220> FEATURE:
<223> OTHER INFORMATION: Synthetic: h4B10-3, CDR-H1

<400> SEQUENCE: 49

Thr Tyr Gly Met Ser
1               5

<210> SEQ ID NO 50
<211> LENGTH: 12
<212> TYPE: PRT
<213> ORGANISM: Artificial Sequence
<220> FEATURE:
<223> OTHER INFORMATION: Synthetic: PD1-17, CDR-H1

<400> SEQUENCE: 50

Ser Gly Gly Ser Ile Arg Ser Thr Arg Trp Trp Ser
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Synthetic: PD1-28, CDR-H1

<400> SEQUENCE: 51

Ser Tyr Gly Ile Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic: PD1-33, CDR-H1

<400> SEQUENCE: 52

Ser Tyr Tyr Ile His
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic: PD1-35, CDR-H1

<400> SEQUENCE: 53

Ser Gly Ala Tyr Tyr Trp Ser
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic: PD1-F2, CDR-H1

<400> SEQUENCE: 54

Ser Tyr Trp Cys Asp Arg Met Ser
1               5

<210> SEQ ID NO 55
```

```
<211> LENGTH: 16
<212> TYPE: PRT
<213> ORGANISM: Artificial Sequence
<220> FEATURE:
<223> OTHER INFORMATION: Synthetic: PD1-17, CDR-H2

<400> SEQUENCE: 55

Glu Ile Tyr His Ser Gly Ser Thr Asn Tyr Asn Pro Ser Leu Lys Ser
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Synthetic: PD1-28, CDR-H2

<400> SEQUENCE: 56

Trp Ile Ser Ala Tyr Asn Gly Asn Thr Asn Tyr Ala Gln Lys Leu Gln
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: Synthetic: PD1-33, CDR-H2

<400> SEQUENCE: 57

Ile Ile Asn Pro Arg Gly Ala Thr Ile Ser Tyr Ala Gln Lys Phe Gln
1               5                   10                  15

Gly

<210> SEQ ID NO 58
<211> LENGTH: 16
<212> TYPE: PRT
<213> ORGANISM: Artificial Sequence
<220> FEATURE:
<223> OTHER INFORMATION: Synthetic: PD1-35, CDR-H2

<400> SEQUENCE: 58

Tyr Ile Tyr Tyr Asn Gly Asn Thr Tyr Tyr Asn Pro Ser Leu Arg Ser
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Synthetic: PD1-F2, CDR-H2

<400> SEQUENCE: 59

Ala Ile Ser Gly Ser Gly Gly Ser Thr Tyr Tyr Ala Asp Ser Val Lys
1               5                   10                  15

Gly

<210> SEQ ID NO 60
<211> LENGTH: 6
<212> TYPE: PRT
<213> ORGANISM: Artificial Sequence
<220> FEATURE:
<223> OTHER INFORMATION: Synthetic: 10B4, CDR-H2

<400> SEQUENCE: 60
```

Phe Pro Gly Ser Gly Ser
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic: 1353-A09, CDR-H2

<400> SEQUENCE: 61

Ser Ala Tyr Asn Gly Asn
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic: 1353-C07, CDR-H2

<400> SEQUENCE: 62

Ser Ala Tyr Asn Gly Asn
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic: 1353-E07, CDR-H2

<400> SEQUENCE: 63

Ser Ala Tyr Asn Gly Asn
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic: 1353-F09, CDR-H2

<400> SEQUENCE: 64

Ser Ala Tyr Asn Gly Asn
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic: 1353-G08, CDR-H2

<400> SEQUENCE: 65

Ser Ala His Asn Gly Asn
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic: 1353-G10, CDR-H2

<400> SEQUENCE: 66

Ser Ala Tyr Asn Gly Asn

<210> SEQ ID NO 67
<211> LENGTH: 6
<212> TYPE: PRT
<213> ORGANISM: Artificial Sequence
<220> FEATURE:
<223> OTHER INFORMATION: Synthetic: 1353-H08, CDR-H2

<400> SEQUENCE: 67

Ser Ala Tyr Asn Gly Asn
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic: 1353-H09, CDR-H2

<400> SEQUENCE: 68

Ser Ala Tyr Asn Gly Asn
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic: 1B10, CDR-H2

<400> SEQUENCE: 69

Ser Tyr Ser Gly Arg
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic: 1E9, CDR-H2

<400> SEQUENCE: 70

Ser Gly Gly Gly Ser Asp
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic: 4B10, CDR-H2

<400> SEQUENCE: 71

Ser Gly Gly Gly Ser Asn
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic: h1E9-1, CDR-H2

<400> SEQUENCE: 72

Ser Gly Gly Gly Ser Asp
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic: h1E9-2, CDR-H2

<400> SEQUENCE: 73

Ser Gly Gly Gly Ser Asp
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic: h1E9-4, CDR-H2

<400> SEQUENCE: 74

Ser Gly Gly Gly Ser Asp
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic: h1E9-5, CDR-H2

<400> SEQUENCE: 75

Ser Gly Gly Gly Ser Asp
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic: h4B10-1, CDR-H2

<400> SEQUENCE: 76

Ser Gly Gly Gly Ser Asn
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic: h4B10-2, CDR-H2

<400> SEQUENCE: 77

Ser Gly Gly Gly Ser Asn
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic: h4B10-3, CDR-H2

<400> SEQUENCE: 78

Ser Gly Gly Gly Ser Asn
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic: PD1-17, CDR-H2

<400> SEQUENCE: 79

Tyr His Ser Gly Ser
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic: PD1-28, CDR-H2

<400> SEQUENCE: 80

Ser Ala Tyr Asn Gly Asn
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic: PD1-33, CDR-H2

<400> SEQUENCE: 81

Asn Pro Arg Gly Ala Thr
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic: PD1-35, CDR-H2

<400> SEQUENCE: 82

Tyr Tyr Asn Gly Asn
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic: PD1-F2, CDR-H2

<400> SEQUENCE: 83

Ser Gly Ser Gly Gly Ser
1               5

<210> SEQ ID NO 84
<211> LENGTH: 17
<212> TYPE: PRT
<213> ORGANISM: Artificial Sequence
<220> FEATURE:
<223> OTHER INFORMATION: Synthetic: 10B4, CDR-H2

<400> SEQUENCE: 84

Lys Ile Phe Pro Gly Ser Gly Ser Ala Asp Tyr Asn Glu Asn Phe Lys
1               5                   10                  15

Gly

```
<210> SEQ ID NO 85
<211> LENGTH: 17
<212> TYPE: PRT
<213> ORGANISM: Artificial Sequence
<220> FEATURE:
<223> OTHER INFORMATION: Synthetic: 1353-A09, CDR-H2

<400> SEQUENCE: 85

Trp Ile Ser Ala Tyr Asn Gly Asn Thr Asn Tyr Ala Gln Lys Leu Gln
1               5                   10                  15

Gly

<210> SEQ ID NO 86
<211> LENGTH: 17
<212> TYPE: PRT
<213> ORGANISM: Artificial Sequence
<220> FEATURE:
<223> OTHER INFORMATION: Synthetic: 1353-C07, CDR-H2

<400> SEQUENCE: 86

Trp Ile Ser Ala Tyr Asn Gly Asn Thr Asn Tyr Ala Gln Lys Leu Gln
1               5                   10                  15

Gly

<210> SEQ ID NO 87
<211> LENGTH: 17
<212> TYPE: PRT
<213> ORGANISM: Artificial Sequence
<220> FEATURE:
<223> OTHER INFORMATION: Synthetic: 1353-E07, CDR-H2

<400> SEQUENCE: 87

Trp Ile Ser Ala Tyr Asn Gly Asn Thr Asn Tyr Ala Gln Lys Leu Gln
1               5                   10                  15

Gly

<210> SEQ ID NO 88
<211> LENGTH: 17
<212> TYPE: PRT
<213> ORGANISM: Artificial Sequence
<220> FEATURE:
<223> OTHER INFORMATION: Synthetic: 1353-F09, CDR-H2

<400> SEQUENCE: 88

Trp Ile Ser Ala Tyr Asn Gly Asn Thr Asn Tyr Ala Gln Lys Leu Gln
1               5                   10                  15

Gly

<210> SEQ ID NO 89
<211> LENGTH: 17
<212> TYPE: PRT
<213> ORGANISM: Artificial Sequence
<220> FEATURE:
<223> OTHER INFORMATION: Synthetic: 1353-G08, CDR-H2

<400> SEQUENCE: 89

Trp Val Ser Ala His Asn Gly Asn Thr Asn Tyr Ala Gln Lys Leu Gln
1               5                   10                  15

Gly

<210> SEQ ID NO 90
<211> LENGTH: 17
```

<212> TYPE: PRT
<213> ORGANISM: Artificial Sequence
<220> FEATURE:
<223> OTHER INFORMATION: Synthetic: 1353-G10, CDR-H2

<400> SEQUENCE: 90

Trp Ile Ser Ala Tyr Asn Gly Asn Thr Asn Tyr Ala Gln Lys Leu Gln
1               5                   10                  15
Gly

<210> SEQ ID NO 91
<211> LENGTH: 17
<212> TYPE: PRT
<213> ORGANISM: Artificial Sequence
<220> FEATURE:
<223> OTHER INFORMATION: Synthetic: 1353-H08, CDR-H2

<400> SEQUENCE: 91

Trp Ile Ser Ala Tyr Asn Gly Asn Thr Lys Tyr Ala Gln Lys Leu Gln
1               5                   10                  15
Gly

<210> SEQ ID NO 92
<211> LENGTH: 17
<212> TYPE: PRT
<213> ORGANISM: Artificial Sequence
<220> FEATURE:
<223> OTHER INFORMATION: Synthetic: 1353-H09, CDR-H2

<400> SEQUENCE: 92

Trp Ile Ser Ala Tyr Asn Gly Asn Thr Asn Tyr Ala Gln Lys Leu Gln
1               5                   10                  15
Gly

<210> SEQ ID NO 93
<211> LENGTH: 16
<212> TYPE: PRT
<213> ORGANISM: Artificial Sequence
<220> FEATURE:
<223> OTHER INFORMATION: Synthetic: 1B10, CDR-H2

<400> SEQUENCE: 93

Tyr Ile Ser Tyr Ser Gly Arg Thr Ser Tyr Asn Pro Ser Leu Thr Ser
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Synthetic: 1E9, CDR-H2

<400> SEQUENCE: 94

Thr Ile Ser Gly Gly Gly Ser Asp Thr Tyr Tyr Pro Asp Ser Val Gln
1               5                   10                  15
Gly

<210> SEQ ID NO 95
<211> LENGTH: 17
<212> TYPE: PRT
<213> ORGANISM: Artificial Sequence
<220> FEATURE:
<223> OTHER INFORMATION: Synthetic: 4B10, CDR-H2

<400> SEQUENCE: 95

Thr Ile Ser Gly Gly Gly Ser Asn Thr Tyr Tyr Ser Asp Ser Val Lys
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Synthetic: h1E9-1, CDR-H2

<400> SEQUENCE: 96

Thr Ile Ser Gly Gly Gly Ser Asp Thr Tyr Tyr Pro Asp Ser Val Gln
1               5                   10                  15

Gly

<210> SEQ ID NO 97
<211> LENGTH: 17
<212> TYPE: PRT
<213> ORGANISM: Artificial Sequence
<220> FEATURE:
<223> OTHER INFORMATION: Synthetic: h1E9-2, CDR-H2

<400> SEQUENCE: 97

Thr Ile Ser Gly Gly Gly Ser Asp Thr Tyr Tyr Pro Asp Ser Val Gln
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic: h1E9-4, CDR-H2

<400> SEQUENCE: 98

Thr Ile Ser Gly Gly Gly Ser Asp Thr Tyr Tyr Pro Asp Ser Val Gln
1               5                   10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic: h1E9-5, CDR-H2

<400> SEQUENCE: 99

Thr Ile Ser Gly Gly Gly Ser Asp Thr Tyr Tyr Pro Asp Ser Val Gln
1               5                   10                  15

Gly

<210> SEQ ID NO 100
<211> LENGTH: 17
<212> TYPE: PRT
<213> ORGANISM: Artificial Sequence
<220> FEATURE:
<223> OTHER INFORMATION: Synthetic: h4B10-1, CDR-H2

<400> SEQUENCE: 100

Thr Ile Ser Gly Gly Gly Ser Asn Thr Tyr Tyr Ser Asp Ser Val Lys
1               5                   10                  15

Gly

<210> SEQ ID NO 101
<211> LENGTH: 17
<212> TYPE: PRT
<213> ORGANISM: Artificial Sequence
<220> FEATURE:
<223> OTHER INFORMATION: Synthetic: h4B10-2, CDR-H2

<400> SEQUENCE: 101

Thr Ile Ser Gly Gly Gly Ser Asn Thr Tyr Tyr Ser Asp Ser Val Lys
1               5                   10                  15

Gly

<210> SEQ ID NO 102
<211> LENGTH: 17
<212> TYPE: PRT
<213> ORGANISM: Artificial Sequence
<220> FEATURE:
<223> OTHER INFORMATION: Synthetic: h4B10-3, CDR-H2

<400> SEQUENCE: 102

Thr Ile Ser Gly Gly Gly Ser Asn Thr Tyr Tyr Ser Asp Ser Val Lys
1               5                   10                  15

Gly

<210> SEQ ID NO 103
<211> LENGTH: 16
<212> TYPE: PRT
<213> ORGANISM: Artificial Sequence
<220> FEATURE:
<223> OTHER INFORMATION: Synthetic: PD1-17, CDR-H2

<400> SEQUENCE: 103

Glu Ile Tyr His Ser Gly Ser Thr Asn Tyr Asn Pro Ser Leu Lys Ser
1               5                   10                  15

<210> SEQ ID NO 104
<211> LENGTH: 17
<212> TYPE: PRT
<213> ORGANISM: Artificial Sequence
<220> FEATURE:
<223> OTHER INFORMATION: Synthetic: PD1-28, CDR-H2

<400> SEQUENCE: 104

Trp Ile Ser Ala Tyr Asn Gly Asn Thr Asn Tyr Ala Gln Lys Leu Gln
1               5                   10                  15

Gly

<210> SEQ ID NO 105
<211> LENGTH: 17
<212> TYPE: PRT
<213> ORGANISM: Artificial Sequence
<220> FEATURE:
<223> OTHER INFORMATION: Synthetic: PD1-33, CDR-H2

<400> SEQUENCE: 105

Ile Ile Asn Pro Arg Gly Ala Thr Ile Ser Tyr Ala Gln Lys Phe Gln
1               5                   10                  15

Gly

<210> SEQ ID NO 106
<211> LENGTH: 16
<212> TYPE: PRT

```
<213> ORGANISM: Artificial Sequence
<220> FEATURE:
<223> OTHER INFORMATION: Synthetic: PD1-35, CDR-H2

<400> SEQUENCE: 106

Tyr Ile Tyr Tyr Asn Gly Asn Thr Tyr Tyr Asn Pro Ser Leu Arg Ser
1               5                   10                  15

<210> SEQ ID NO 107
<211> LENGTH: 17
<212> TYPE: PRT
<213> ORGANISM: Artificial Sequence
<220> FEATURE:
<223> OTHER INFORMATION: Synthetic: PD1-F2, CDR-H2

<400> SEQUENCE: 107

Ala Ile Ser Gly Ser Gly Gly Ser Thr Tyr Tyr Ala Asp Ser Val Lys
1               5                   10                  15

Gly

<210> SEQ ID NO 108
<211> LENGTH: 13
<212> TYPE: PRT
<213> ORGANISM: Artificial Sequence
<220> FEATURE:
<223> OTHER INFORMATION: Synthetic: PD1-17, CDR-H3

<400> SEQUENCE: 108

Gln Asp Tyr Gly Asp Ser Gly Asp Trp Tyr Phe Asp Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic: PD1-28, CDR-H3

<400> SEQUENCE: 109

Asp Ala Asp Tyr Ser Ser Gly Ser Gly Tyr
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic: PD1-33, CDR-H3

<400> SEQUENCE: 110

Ala Gly Ile Tyr Gly Phe Asp Phe Asp Tyr
1               5                   10

<210> SEQ ID NO 111
<211> LENGTH: 17
<212> TYPE: PRT
<213> ORGANISM: Artificial Sequence
<220> FEATURE:
<223> OTHER INFORMATION: Synthetic: PD1-35, CDR-H3

<400> SEQUENCE: 111

Ala Ser Asp Tyr Val Trp Gly Gly Tyr Arg Tyr Met Asp Ala Phe Asp
1               5                   10                  15

Ile
```

```
<210> SEQ ID NO 112
<211> LENGTH: 9
<212> TYPE: PRT
<213> ORGANISM: Artificial Sequence
<220> FEATURE:
<223> OTHER INFORMATION: Synthetic: PD1-F2, CDR-H3

<400> SEQUENCE: 112

Glu Asn Trp Gly Ser Tyr Phe Asp Leu
1               5

<210> SEQ ID NO 113
<211> LENGTH: 10
<212> TYPE: PRT
<213> ORGANISM: Artificial Sequence
<220> FEATURE:
<223> OTHER INFORMATION: Synthetic: 10B4, CDR-H3

<400> SEQUENCE: 113

Gly Tyr Gly Asn Tyr Leu Tyr Phe Asp Val
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthetic: 1353-A09, CDR-H3

<400> SEQUENCE: 114

Asp Ser Glu Tyr Ser Ser Gly Ser Gly Tyr
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic: 1353-C07, CDR-H3

<400> SEQUENCE: 115

Asp Val Asp Tyr Ser Ser Gly Ser Gly Tyr
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic: 1353-E07, CDR-H3

<400> SEQUENCE: 116

Asp Ala Glu Tyr Ser Leu Gly Ser Gly Tyr
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthetic: 1353-F09, CDR-H3

<400> SEQUENCE: 117

Asp Ala Glu Tyr Gly Ser Gly Ser Gly Tyr
1               5                   10

<210> SEQ ID NO 118
```

```
<210> SEQ ID NO 118
<211> LENGTH: 10
<212> TYPE: PRT
<213> ORGANISM: Artificial Sequence
<220> FEATURE:
<223> OTHER INFORMATION: Synthetic: 1353-G08, CDR-H3

<400> SEQUENCE: 118

Asp Ala Asp Tyr Gly Ser Gly Ser Gly Tyr
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic: 1353-G10, CDR-H3

<400> SEQUENCE: 119

Asp Val Asp Tyr Gly Thr Gly Ser Gly Tyr
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthetic: 1353-H08, CDR-H3

<400> SEQUENCE: 120

Asp Val Asp Tyr Gly Ser Gly Ser Gly Tyr
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic: 1353-H09, CDR-H3

<400> SEQUENCE: 121

Asp Ala Glu Tyr Gly Ser Gly Ser Gly Tyr
1               5                   10

<210> SEQ ID NO 122
<211> LENGTH: 6
<212> TYPE: PRT
<213> ORGANISM: Artificial Sequence
<220> FEATURE:
<223> OTHER INFORMATION: Synthetic: 1B10, CDR-H3

<400> SEQUENCE: 122

Gly Tyr Ala Leu Asp Tyr
1               5

<210> SEQ ID NO 123
<211> LENGTH: 11
<212> TYPE: PRT
<213> ORGANISM: Artificial Sequence
<220> FEATURE:
<223> OTHER INFORMATION: Synthetic: 1E9, CDR-H3

<400> SEQUENCE: 123

Gln Gly Tyr Asp Val Tyr Ser Trp Phe Ala Tyr
1               5                   10

<210> SEQ ID NO 124
<211> LENGTH: 9
```

```
<212> TYPE: PRT
<213> ORGANISM: Artificial Sequence
<220> FEATURE:
<223> OTHER INFORMATION: Synthetic: 4B10, CDR-H3

<400> SEQUENCE: 124

Gln Arg Asp Ser Ala Trp Phe Ala Ser
1               5

<210> SEQ ID NO 125
<211> LENGTH: 11
<212> TYPE: PRT
<213> ORGANISM: Artificial Sequence
<220> FEATURE:
<223> OTHER INFORMATION: Synthetic: h1E9-1, CDR-H3

<400> SEQUENCE: 125

Gln Gly Tyr Asp Val Tyr Ser Trp Phe Ala Tyr
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthetic: h1E9-2, CDR-H3

<400> SEQUENCE: 126

Gln Gly Tyr Asp Val Tyr Ser Trp Phe Ala Tyr
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthetic: h1E9-4, CDR-H3

<400> SEQUENCE: 127

Gln Gly Tyr Asp Val Tyr Ser Trp Phe Ala Tyr
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic: h1E9-5, CDR-H3

<400> SEQUENCE: 128

Gln Gly Tyr Asp Val Tyr Ser Trp Phe Ala Tyr
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Synthetic: h4B10-1, CDR-H3

<400> SEQUENCE: 129

Gln Arg Asp Ser Ala Trp Phe Ala Ser
1               5

<210> SEQ ID NO 130
<211> LENGTH: 9
<212> TYPE: PRT
```

```
<213> ORGANISM: Artificial Sequence
<220> FEATURE:
<223> OTHER INFORMATION: Synthetic: h4B10-2, CDR-H3

<400> SEQUENCE: 130

Gln Arg Asp Ser Ala Trp Phe Ala Ser
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic: h4B10-3, CDR-H3

<400> SEQUENCE: 131

Gln Arg Asp Ser Ala Trp Phe Ala Ser
1               5

<210> SEQ ID NO 132
<211> LENGTH: 13
<212> TYPE: PRT
<213> ORGANISM: Artificial Sequence
<220> FEATURE:
<223> OTHER INFORMATION: Synthetic: PD1-17, CDR-H3

<400> SEQUENCE: 132

Gln Asp Tyr Gly Asp Ser Gly Asp Trp Tyr Phe Asp Leu
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Synthetic: PD1-28, CDR-H3

<400> SEQUENCE: 133

Asp Ala Asp Tyr Ser Ser Gly Ser Gly Tyr
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic: PD1-33, CDR-H3

<400> SEQUENCE: 134

Ala Gly Ile Tyr Gly Phe Asp Phe Asp Tyr
1               5                   10

<210> SEQ ID NO 135
<211> LENGTH: 17
<212> TYPE: PRT
<213> ORGANISM: Artificial Sequence
<220> FEATURE:
<223> OTHER INFORMATION: Synthetic: PD1-35, CDR-H3

<400> SEQUENCE: 135

Ala Ser Asp Tyr Val Trp Gly Gly Tyr Arg Tyr Met Asp Ala Phe Asp
1               5                   10                  15

Ile

<210> SEQ ID NO 136
<211> LENGTH: 9
```

```
<212> TYPE: PRT
<213> ORGANISM: Artificial Sequence
<220> FEATURE:
<223> OTHER INFORMATION: Synthetic: PD1-F2, CDR-H3

<400> SEQUENCE: 136

Glu Asn Trp Gly Ser Tyr Phe Asp Leu
1               5

<210> SEQ ID NO 137
<211> LENGTH: 13
<212> TYPE: PRT
<213> ORGANISM: Artificial Sequence
<220> FEATURE:
<223> OTHER INFORMATION: Synthetic: PD1-17, CDR-L1

<400> SEQUENCE: 137

Thr Arg Ser Ser Gly Ser Ile Ala Ser Asn Ser Val Gln
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Synthetic: PD1-28, CDR-L1

<400> SEQUENCE: 138

Ser Gly Asp Ala Leu Pro Lys Gln Tyr Ala Tyr
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Synthetic: PD1-33, CDR-L1

<400> SEQUENCE: 139

Thr Gly Thr Ser Asn Asp Val Gly Gly Tyr Asn Tyr Val Ser
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic: PD1-35, CDR-L1

<400> SEQUENCE: 140

Ser Gly Ser Asn Ser Asn Ile Gly Ser Asn Ser Val Asn
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic: PD1-F2, CDR-L1

<400> SEQUENCE: 141

Arg Ala Ser Gln Gly Ile Ser Ser Trp Leu Ala
1               5                   10

<210> SEQ ID NO 142
<211> LENGTH: 11
<212> TYPE: PRT
```

```
<213> ORGANISM: Artificial Sequence
<220> FEATURE:
<223> OTHER INFORMATION: Synthetic: 10B4, CDR-L1

<400> SEQUENCE: 142

Lys Ala Ser Gln Ser Val Ser Asp Asp Val Ala
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Synthetic: 1353-A09, CDR-L1

<400> SEQUENCE: 143

Ser Gly Asp Ala Leu Thr Thr Gln Tyr Ala Tyr
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Synthetic: 1353-C07, CDR-L1

<400> SEQUENCE: 144

Ser Gly Asp Ala Leu Ser Glu Gln Tyr Ala Tyr
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Synthetic: 1353-E07, CDR-L1

<400> SEQUENCE: 145

Ser Gly Asp Ala Leu Pro Lys Gln Tyr Ala Tyr
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic: 1353-F09, CDR-L1

<400> SEQUENCE: 146

Ser Gly Asp Ala Leu Pro Lys Gln Tyr Ala Tyr
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic: 1353-G08, CDR-L1

<400> SEQUENCE: 147

Ser Gly Asp Ala Leu Pro Met Gln Tyr Gly Tyr
1               5                   10

<210> SEQ ID NO 148
<211> LENGTH: 11
<212> TYPE: PRT
<213> ORGANISM: Artificial Sequence
```

```
<220> FEATURE:
<223> OTHER INFORMATION: Synthetic: 1353-G10, CDR-L1

<400> SEQUENCE: 148

Ser Gly Asp Ala Leu Pro Lys Gln Tyr Ala Tyr
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Synthetic: 1353-H08, CDR-L1

<400> SEQUENCE: 149

Ser Gly Asp Ala Leu Pro Lys Gln Tyr Ala Tyr
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Synthetic: 1353-H09, CDR-L1

<400> SEQUENCE: 150

Ser Gly Asp Ala Leu Pro Lys Gln Tyr Ala Tyr
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic: 1B10, CDR-L1

<400> SEQUENCE: 151

Arg Thr Ser Ser Ser Val Asn Tyr Met His
1               5                   10

<210> SEQ ID NO 152
<211> LENGTH: 15
<212> TYPE: PRT
<213> ORGANISM: Artificial Sequence
<220> FEATURE:
<223> OTHER INFORMATION: Synthetic: 1E9, CDR-L1

<400> SEQUENCE: 152

Arg Ala Ser Glu Ser Val Asp Asn Ser Gly Ile Ser Phe Met Ser
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Synthetic: 4B10, CDR-L1

<400> SEQUENCE: 153

Arg Ala Ser Glu Asn Val Asp Asp Tyr Gly Val Ser Phe Met Asn
1               5                   10                  15

<210> SEQ ID NO 154
<211> LENGTH: 15
<212> TYPE: PRT
<213> ORGANISM: Artificial Sequence
<220> FEATURE:
```

<223> OTHER INFORMATION: Synthetic: h1E9-1, CDR-L1

<400> SEQUENCE: 154

Arg Ala Ser Glu Ser Val Asp Asn Ser Gly Ile Ser Phe Met Ser
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Synthetic: h1E9-2, CDR-L1

<400> SEQUENCE: 155

Arg Ala Ser Glu Ser Val Asp Asn Ser Gly Ile Ser Phe Met Ser
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic: h1E9-4, CDR-L1

<400> SEQUENCE: 156

Arg Ala Ser Glu Ser Val Asp Asn Ser Gly Ile Ser Phe Met Ser
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic: h1E9-5, CDR-L1

<400> SEQUENCE: 157

Arg Ala Ser Glu Ser Val Asp Asn Ser Gly Ile Ser Phe Met Ser
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic: h4B10-1, CDR-L1

<400> SEQUENCE: 158

Arg Ala Ser Glu Asn Val Asp Asp Tyr Gly Val Ser Phe Met Asn
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Synthetic: h4B10-2, CDR-L1

<400> SEQUENCE: 159

Arg Ala Ser Glu Asn Val Asp Asp Tyr Gly Val Ser Phe Met Asn
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Synthetic: h4B10-3, CDR-L1

```
<400> SEQUENCE: 160

Arg Ala Ser Glu Asn Val Asp Asp Tyr Gly Val Ser Phe Met Asn
1               5                   10                  15

<210> SEQ ID NO 161
<211> LENGTH: 13
<212> TYPE: PRT
<213> ORGANISM: Artificial Sequence
<220> FEATURE:
<223> OTHER INFORMATION: Synthetic: PD1-17, CDR-L1

<400> SEQUENCE: 161

Thr Arg Ser Ser Gly Ser Ile Ala Ser Asn Ser Val Gln
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Synthetic: PD1-28, CDR-L1

<400> SEQUENCE: 162

Ser Gly Asp Ala Leu Pro Lys Gln Tyr Ala Tyr
1               5                   10

<210> SEQ ID NO 163
<211> LENGTH: 14
<212> TYPE: PRT
<213> ORGANISM: Artificial Sequence
<220> FEATURE:
<223> OTHER INFORMATION: Synthetic: PD1-33, CDR-L1

<400> SEQUENCE: 163

Thr Gly Thr Ser Asn Asp Val Gly Gly Tyr Asn Tyr Val Ser
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Synthetic: PD1-35, CDR-L1

<400> SEQUENCE: 164

Ser Gly Ser Asn Ser Asn Ile Gly Ser Asn Ser Val Asn
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthetic: PD1-F2, CDR-L1

<400> SEQUENCE: 165

Arg Ala Ser Gln Gly Ile Ser Ser Trp Leu Ala
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Synthetic: PD1-17, CDR-L2
```

```
<400> SEQUENCE: 166

Glu Asp Asn Gln Arg Pro Ser
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic: PD1-28, CDR-L2

<400> SEQUENCE: 167

Lys Asp Thr Glu Arg Pro Ser
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic: PD1-33, CDR-L2

<400> SEQUENCE: 168

Asp Val Thr Asn Arg Pro Ser
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic: PD1-35, CDR-L2

<400> SEQUENCE: 169

Gly Asn Asn Gln Arg Pro Ser
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic: PD1-F2, CDR-L2

<400> SEQUENCE: 170

Lys Ala Ser Thr Leu Glu Ser
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic: 10B4, CDR-L2

<400> SEQUENCE: 171

Tyr Ala Phe Lys Arg Tyr Ile
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic: 1353-A09, CDR-L2

<400> SEQUENCE: 172
```

```
Lys Asp Thr Glu Arg Pro Ser
1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic: 1353-C07, CDR-L2

<400> SEQUENCE: 173

Lys Asp Thr Glu Arg Pro Ser
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic: 1353-E07, CDR-L2

<400> SEQUENCE: 174

Lys Asp Thr Glu Arg Pro Ser
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic: 1353-F09, CDR-L2

<400> SEQUENCE: 175

Lys Asp Thr Glu Arg Pro Ser
1               5

<210> SEQ ID NO 176
<211> LENGTH: 7
<212> TYPE: PRT
<213> ORGANISM: Artificial Sequence
<220> FEATURE:
<223> OTHER INFORMATION: Synthetic: 1353-G08, CDR-L2

<400> SEQUENCE: 176

Lys Asp Thr Glu Arg Pro Ser
1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic: 1353-G10, CDR-L2

<400> SEQUENCE: 177

Lys Asp Thr Glu Arg Pro Ser
1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic: 1353-H08, CDR-L2

<400> SEQUENCE: 178
```

```
Lys Asp Thr Glu Arg Pro Ser
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic: 1353-H09, CDR-L2

<400> SEQUENCE: 179

Lys Asp Thr Glu Arg Pro Ser
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic: 1B10, CDR-L2

<400> SEQUENCE: 180

Ala Thr Ser Lys Leu Ala Ser
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic: 1E9, CDR-L2

<400> SEQUENCE: 181

Thr Ala Ser Asn Gln Gly Ser
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic: 4B10, CDR-L2

<400> SEQUENCE: 182

Pro Ala Ser Asn Gln Gly Ser
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic: h1E9-1, CDR-L2

<400> SEQUENCE: 183

Thr Ala Ser Asn Gln Gly Ser
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic: h1E9-2, CDR-L2

<400> SEQUENCE: 184

Thr Ala Ser Asn Gln Gly Ser
```

```
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic: h1E9-4, CDR-L2

<400> SEQUENCE: 185

Thr Ala Ser Asn Gln Gly Ser
1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic: h1E9-5, CDR-L2

<400> SEQUENCE: 186

Thr Ala Ser Asn Gln Gly Ser
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic: h4B10-1, CDR-L2

<400> SEQUENCE: 187

Pro Ala Ser Asn Gln Gly Ser
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic: h4B10-2, CDR-L2

<400> SEQUENCE: 188

Pro Ala Ser Asn Gln Gly Ser
1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic: h4B10-3, CDR-L2

<400> SEQUENCE: 189

Pro Ala Ser Asn Gln Gly Ser
1               5

<210> SEQ ID NO 190
<211> LENGTH: 7
<212> TYPE: PRT
<213> ORGANISM: Artificial Sequence
<220> FEATURE:
<223> OTHER INFORMATION: Synthetic: PD1-17, CDR-L2

<400> SEQUENCE: 190

Glu Asp Asn Gln Arg Pro Ser
1               5
```

<210> SEQ ID NO 191
<211> LENGTH: 7
<212> TYPE: PRT
<213> ORGANISM: Artificial Sequence
<220> FEATURE:
<223> OTHER INFORMATION: Synthetic: PD1-28, CDR-L2

<400> SEQUENCE: 191

Lys Asp Thr Glu Arg Pro Ser
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic: PD1-33, CDR-L2

<400> SEQUENCE: 192

Asp Val Thr Asn Arg Pro Ser
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic: PD1-35, CDR-L2

<400> SEQUENCE: 193

Gly Asn Asn Gln Arg Pro Ser
1               5

<210> SEQ ID NO 194
<211> LENGTH: 7
<212> TYPE: PRT
<213> ORGANISM: Artificial Sequence
<220> FEATURE:
<223> OTHER INFORMATION: Synthetic: PD1-F2, CDR-L2

<400> SEQUENCE: 194

Lys Ala Ser Thr Leu Glu Ser
1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic: PD1-17, CDR-L3

<400> SEQUENCE: 195

Gln Ser Ser Asp Ser Ser Ala Val Val
1               5

<210> SEQ ID NO 196
<211> LENGTH: 11
<212> TYPE: PRT
<213> ORGANISM: Artificial Sequence
<220> FEATURE:
<223> OTHER INFORMATION: Synthetic: PD1-28, CDR-L3

<400> SEQUENCE: 196

Gln Ser Ala Asp Asn Ser Ile Thr Tyr Arg Val
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Synthetic: PD1-33, CDR-L3

<400> SEQUENCE: 197

Ser Ser Tyr Thr Ile Val Thr Asn Phe Glu Val Leu
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Synthetic: PD1-35, CDR-L3

<400> SEQUENCE: 198

Ala Ala Trp Asp Asp Ser Leu Asn Gly Pro Val
1               5                   10

<210> SEQ ID NO 199
<211> LENGTH: 9
<212> TYPE: PRT
<213> ORGANISM: Artificial Sequence
<220> FEATURE:
<223> OTHER INFORMATION: Synthetic: PD1-F2, CDR-L3

<400> SEQUENCE: 199

Gln Gln Ser Tyr Ser Thr Pro Trp Thr
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic: 10B4, CDR-L3

<400> SEQUENCE: 200

Gln Gln Asn Tyr Asn Ser Pro Tyr Thr
1               5

<210> SEQ ID NO 201
<211> LENGTH: 11
<212> TYPE: PRT
<213> ORGANISM: Artificial Sequence
<220> FEATURE:
<223> OTHER INFORMATION: Synthetic: 1353-A09, CDR-L3

<400> SEQUENCE: 201

Gln Ser Ala Asp Asn Ser Ile Thr Tyr Arg Val
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Synthetic: 1353-C07, CDR-L3

<400> SEQUENCE: 202

Gln Ser Ala Asp Asn Ser Ile Thr Tyr Arg Val
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Synthetic: 1353-E07, CDR-L3

<400> SEQUENCE: 203

Gln Ser Ala Asp Asn Ser Ile Thr Tyr Arg Val
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Synthetic: 1353-F09, CDR-L3

<400> SEQUENCE: 204

Gln Ser Ala Asp Asn Ser Ile Thr Tyr Arg Val
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Synthetic: 1353-G08, CDR-L3

<400> SEQUENCE: 205

Gln Ser Ala Asp Asn Ser Ile Thr Tyr Arg Val
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Synthetic: 1353-G10, CDR-L3

<400> SEQUENCE: 206

Gln Ser Ala Asp Asn Ser Ile Thr Tyr Arg Val
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Synthetic: 1353-H08, CDR-L3

<400> SEQUENCE: 207

Gln Ser Ala Asp Asn Ser Ile Thr Tyr Arg Val
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Synthetic: 1353-H09, CDR-L3

<400> SEQUENCE: 208

Gln Ser Ala Asp Asn Ser Ile Thr Tyr Arg Val
1               5                   10

<210> SEQ ID NO 209

```
<211> LENGTH: 9
<212> TYPE: PRT
<213> ORGANISM: Artificial Sequence
<220> FEATURE:
<223> OTHER INFORMATION: Synthetic: 1B10, CDR-L3

<400> SEQUENCE: 209

Gln Gln Trp Ile Ser Asp Pro Trp Thr
1               5

<210> SEQ ID NO 210
<211> LENGTH: 9
<212> TYPE: PRT
<213> ORGANISM: Artificial Sequence
<220> FEATURE:
<223> OTHER INFORMATION: Synthetic: 1E9, CDR-L3

<400> SEQUENCE: 210

Gln Gln Ser Lys Glu Val Pro Trp Thr
1               5

<210> SEQ ID NO 211
<211> LENGTH: 9
<212> TYPE: PRT
<213> ORGANISM: Artificial Sequence
<220> FEATURE:
<223> OTHER INFORMATION: Synthetic: 4B10, CDR-L3

<400> SEQUENCE: 211

Gln Gln Ser Lys Glu Val Pro Trp Thr
1               5

<210> SEQ ID NO 212
<211> LENGTH: 9
<212> TYPE: PRT
<213> ORGANISM: Artificial Sequence
<220> FEATURE:
<223> OTHER INFORMATION: Synthetic: h1E9-1, CDR-L3

<400> SEQUENCE: 212

Gln Gln Ser Lys Glu Val Pro Trp Thr
1               5

<210> SEQ ID NO 213
<211> LENGTH: 9
<212> TYPE: PRT
<213> ORGANISM: Artificial Sequence
<220> FEATURE:
<223> OTHER INFORMATION: Synthetic: h1E9-2, CDR-L3

<400> SEQUENCE: 213

Gln Gln Ser Lys Glu Val Pro Trp Thr
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic: h1E9-4, CDR-L3

<400> SEQUENCE: 214

Gln Gln Ser Lys Glu Val Pro Trp Thr
1               5

<210> SEQ ID NO 215
<211> LENGTH: 9
```

```
<212> TYPE: PRT
<213> ORGANISM: Artificial Sequence
<220> FEATURE:
<223> OTHER INFORMATION: Synthetic: h1E9-5, CDR-L3

<400> SEQUENCE: 215

Gln Gln Ser Lys Glu Val Pro Trp Thr
1               5

<210> SEQ ID NO 216
<211> LENGTH: 9
<212> TYPE: PRT
<213> ORGANISM: Artificial Sequence
<220> FEATURE:
<223> OTHER INFORMATION: Synthetic: h4B10-1, CDR-L3

<400> SEQUENCE: 216

Gln Gln Ser Lys Glu Val Pro Trp Thr
1               5

<210> SEQ ID NO 217
<211> LENGTH: 9
<212> TYPE: PRT
<213> ORGANISM: Artificial Sequence
<220> FEATURE:
<223> OTHER INFORMATION: Synthetic: h4B10-2, CDR-L3

<400> SEQUENCE: 217

Gln Gln Ser Lys Glu Val Pro Trp Thr
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic: h4B10-3, CDR-L3

<400> SEQUENCE: 218

Gln Gln Ser Lys Glu Val Pro Trp Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic: PD1-17, CDR-L3

<400> SEQUENCE: 219

Gln Ser Ser Asp Ser Ser Ala Val Val
1               5

<210> SEQ ID NO 220
<211> LENGTH: 11
<212> TYPE: PRT
<213> ORGANISM: Artificial Sequence
<220> FEATURE:
<223> OTHER INFORMATION: Synthetic: PD1-28, CDR-L3

<400> SEQUENCE: 220

Gln Ser Ala Asp Asn Ser Ile Thr Tyr Arg Val
1               5                   10

<210> SEQ ID NO 221
<211> LENGTH: 12
<212> TYPE: PRT
```

<213> ORGANISM: Artificial Sequence
<220> FEATURE:
<223> OTHER INFORMATION: Synthetic: PD1-33, CDR-L3

<400> SEQUENCE: 221

Ser Ser Tyr Thr Ile Val Thr Asn Phe Glu Val Leu
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Synthetic: PD1-35, CDR-L3

<400> SEQUENCE: 222

Ala Ala Trp Asp Asp Ser Leu Asn Gly Pro Val
1               5                   10

<210> SEQ ID NO 223
<211> LENGTH: 9
<212> TYPE: PRT
<213> ORGANISM: Artificial Sequence
<220> FEATURE:
<223> OTHER INFORMATION: Synthetic: PD1-F2, CDR-L3

<400> SEQUENCE: 223

Gln Gln Ser Tyr Ser Thr Pro Trp Thr
1               5

<210> SEQ ID NO 224
<211> LENGTH: 330
<212> TYPE: PRT
<213> ORGANISM: Artificial Sequence
<220> FEATURE:
<223> OTHER INFORMATION: Synthetic: HC Constant

<400> SEQUENCE: 224

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu

```
                180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 225
<211> LENGTH: 108
<212> TYPE: PRT
<213> ORGANISM: Artificial Sequence
<220> FEATURE:
<223> OTHER INFORMATION: Synthetic: Kappa LC

<400> SEQUENCE: 225

His Met Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 226
<211> LENGTH: 106
<212> TYPE: PRT
<213> ORGANISM: Artificial Sequence
<220> FEATURE:
<223> OTHER INFORMATION: Synthetic: Lambda LD

<400> SEQUENCE: 226

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45
```

Val Lys Ala Gly Val Glu Thr Thr Pro Ser Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 227
<211> LENGTH: 267
<212> TYPE: PRT
<213> ORGANISM: Artificial Sequence
<220> FEATURE:
<223> OTHER INFORMATION: Synthetic: h1E9-1, scFv

<400> SEQUENCE: 227

Met Glu Val Gln Leu Val Glu Ser Gly Gly Gly Leu Val Lys Pro Gly
 1               5                  10                  15

Gly Ser Leu Arg Leu Ser Cys Ala Ala Ser Gly Phe Thr Phe Ser Thr
                 20                  25                  30

Phe Gly Met Ser Trp Val Arg Gln Ala Pro Gly Lys Gly Leu Glu Trp
             35                  40                  45

Val Ser Thr Ile Ser Gly Gly Gly Ser Asp Thr Tyr Tyr Pro Asp Ser
 50                  55                  60

Val Gln Gly Arg Phe Thr Ile Ser Arg Asp Asn Ala Lys Asn Ser Leu
 65                  70                  75                  80

Tyr Leu Gln Met Asn Ser Leu Arg Ala Glu Asp Thr Ala Val Tyr Tyr
                 85                  90                  95

Cys Ala Arg Gln Gly Tyr Asp Val Tyr Ser Trp Phe Ala Tyr Trp Gly
            100                 105                 110

Gln Gly Thr Leu Val Thr Val Ser Ser Gly Gly Gly Gly Ser Gly Gly
            115                 120                 125

Gly Gly Ser Gly Gly Gly Gly Ser Asp Ile Gln Leu Thr Gln Ser Pro
130                 135                 140

Ser Phe Leu Ser Ala Ser Val Gly Asp Arg Val Thr Ile Thr Cys Arg
145                 150                 155                 160

Ala Ser Glu Ser Val Asp Asn Ser Gly Ile Ser Phe Met Ser Trp Tyr
                165                 170                 175

Gln Gln Lys Pro Gly Lys Ala Pro Lys Leu Leu Ile Tyr Thr Ala Ser
            180                 185                 190

Asn Gln Gly Ser Gly Val Pro Ser Arg Phe Ser Gly Ser Gly Ser Gly
            195                 200                 205

Thr Glu Phe Thr Leu Thr Ile Ser Ser Leu Gln Pro Glu Asp Phe Ala
            210                 215                 220

Thr Tyr Tyr Cys Gln Gln Ser Lys Glu Val Pro Trp Thr Phe Gly Gln
225                 230                 235                 240

Gly Thr Lys Val Glu Ile Lys Gly Ser Gly Asp Tyr Lys Asp Asp Asp
                245                 250                 255

Asp Lys Gly Ser Gly His His His His His
            260                 265

<210> SEQ ID NO 228
<211> LENGTH: 267
<212> TYPE: PRT
<213> ORGANISM: Artificial Sequence
<220> FEATURE:

<223> OTHER INFORMATION: Synthetic: h1E9-2, scFv

<400> SEQUENCE: 228

```
Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Thr Phe Ser Thr
            20                  25                  30

Phe Gly Met Ser Trp Val Arg Gln Ala Pro Gly Lys Gly Leu Glu Trp
        35                  40                  45

Val Ser Thr Ile Ser Gly Gly Ser Asp Thr Tyr Tyr Pro Asp Ser
50                  55                  60

Val Gln Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gln Gly Tyr Asp Val Tyr Ser Trp Phe Ala Tyr Trp Gly
            100                 105                 110

Gln Gly Thr Leu Val Thr Val Ser Gly Gly Gly Gly Ser Gly Gly
        115                 120                 125

Gly Gly Ser Gly Gly Gly Ser Glu Ile Val Leu Thr Gln Ser Pro
130                 135                 140

Ala Thr Leu Ser Leu Ser Pro Gly Glu Arg Ala Thr Leu Ser Cys Arg
145                 150                 155                 160

Ala Ser Glu Ser Val Asp Asn Ser Gly Ile Ser Phe Met Ser Trp Tyr
                165                 170                 175

Gln Gln Lys Pro Gly Gln Ala Pro Arg Leu Leu Ile Tyr Thr Ala Ser
            180                 185                 190

Asn Gln Gly Ser Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
210                 215                 220

Val Tyr Tyr Cys Gln Gln Ser Lys Glu Val Pro Trp Thr Phe Gly Gln
225                 230                 235                 240

Gly Thr Lys Val Glu Ile Lys Gly Ser Gly Asp Tyr Lys Asp Asp Asp
                245                 250                 255

Asp Lys Gly Ser Gly His His His His His His
            260                 265
```

<210> SEQ ID NO 229
<211> LENGTH: 267
<212> TYPE: PRT
<213> ORGANISM: Artificial Sequence
<220> FEATURE:
<223> OTHER INFORMATION: Synthetic: h1E9-4, scFv

<400> SEQUENCE: 229

```
Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Thr
            20                  25                  30

Phe Gly Met Ser Trp Val Arg Gln Ala Pro Gly Lys Gly Leu Glu Trp
        35                  40                  45

Val Ala Thr Ile Ser Gly Gly Ser Asp Thr Tyr Tyr Pro Asp Ser
50                  55                  60

Val Gln Gly Arg Phe Thr Ile Ser Arg Asp Asn Ala Lys Asn Ser Leu
65                  70                  75                  80
```

```
Tyr Leu Gln Met Asn Ser Leu Arg Ala Glu Asp Thr Ala Val Tyr Tyr
                85                  90                  95

Cys Ala Arg Gln Gly Tyr Asp Val Tyr Ser Trp Phe Ala Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Leu Thr Gln Ser Pro
130                 135                 140

Ser Phe Leu Ser Ala Ser Val Gly Asp Arg Val Thr Ile Thr Cys Arg
145                 150                 155                 160

Ala Ser Glu Ser Val Asp Asn Ser Gly Ile Ser Phe Met Ser Trp Tyr
                165                 170                 175

Gln Gln Lys Pro Gly Lys Ala Pro Lys Leu Leu Ile Tyr Thr Ala Ser
            180                 185                 190

Asn Gln Gly Ser Gly Val Pro Ser Arg Phe Ser Gly Ser Gly Ser Gly
        195                 200                 205

Thr Glu Phe Thr Leu Thr Ile Ser Ser Leu Gln Pro Glu Asp Phe Ala
210                 215                 220

Thr Tyr Tyr Cys Gln Gln Ser Lys Glu Val Pro Trp Thr Phe Gly Gln
225                 230                 235                 240

Gly Thr Lys Val Glu Ile Lys Gly Ser Gly Asp Tyr Lys Asp Asp Asp
                245                 250                 255

Asp Lys Gly Ser Gly His His His His His His
            260                 265

<210> SEQ ID NO 230
<211> LENGTH: 267
<212> TYPE: PRT
<213> ORGANISM: Artificial Sequence
<220> FEATURE:
<223> OTHER INFORMATION: Synthetic: h1E9-5, scFv

<400> SEQUENCE: 230

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Thr
            20                  25                  30

Phe Gly Met Ser Trp Val Arg Gln Ala Pro Gly Lys Gly Leu Glu Trp
        35                  40                  45

Val Ala Thr Ile Ser Gly Gly Ser Asp Thr Tyr Tyr Pro Asp Ser
50                  55                  60

Val Gln Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gln Gly Tyr Asp Val Tyr Ser Trp Phe Ala Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Glu Ile Val Leu Thr Gln Ser Pro
130                 135                 140

Ala Thr Leu Ser Leu Ser Pro Gly Glu Arg Ala Thr Leu Ser Cys Arg
145                 150                 155                 160

Ala Ser Glu Ser Val Asp Asn Ser Gly Ile Ser Phe Met Ser Trp Tyr
                165                 170                 175
```

Gln Gln Lys Pro Gly Gln Ala Pro Arg Leu Leu Ile Tyr Thr Ala Ser
            180                 185                 190

Asn Gln Gly Ser Gly Ile Pro Ala Arg Phe Ser Gly Ser Gly
            195                 200                 205        Gly

Thr Asp Phe Thr Leu Thr Ile Ser Ser Leu Glu Pro Glu Asp Phe Ala
            210                 215                 220

Val Tyr Tyr Cys Gln Gln Ser Lys Glu Val Pro Trp Thr Phe Gly Gln
225                 230                 235                 240

Gly Thr Lys Val Glu Ile Lys Gly Ser Gly Asp Tyr Lys Asp Asp Asp
            245                 250                 255

Asp Lys Gly Ser Gly His His His His His His
            260                 265

<210> SEQ ID NO 231
<211> LENGTH: 265
<212> TYPE: PRT
<213> ORGANISM: Artificial Sequence
<220> FEATURE:
<223> OTHER INFORMATION: Synthetic: h4B10-1, scFv

<400> SEQUENCE: 231

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Thr Phe Ser Thr
            20                  25                  30

Tyr Gly Met Ser Trp Val Arg Gln Ala Pro Lys Gly Leu Glu Trp
            35                  40                  45

Val Ala Thr Ile Ser Gly Gly Gly Ser Asn Thr Tyr Tyr Ser Asp Ser
50                  55                  60

Val Lys Gly Arg Phe Thr Ile Ser Arg Asp Asp Ser Lys Asn Thr Leu
65                  70                  75                  80

Tyr Leu Gln Met Asn Ser Leu Lys Thr Glu Asp Thr Ala Val Tyr Tyr
            85                  90                  95

Cys Ala Arg Gln Arg Asp Ser Ala Trp Phe Ala Ser Trp Gly Gln Gly
            100                 105                 110

Thr Leu Val Thr Val Ser Ser Gly Gly Gly Ser Gly Gly Gly Gly
            115                 120                 125

Ser Gly Gly Gly Ser Glu Ile Val Leu Thr Gln Ser Pro Ala Thr
            130                 135                 140

Leu Ser Leu Ser Pro Gly Glu Arg Ala Thr Leu Ser Cys Arg Ala Ser
145                 150                 155                 160

Glu Asn Val Asp Asp Tyr Gly Val Ser Phe Met Asn Trp Tyr Gln Gln
            165                 170                 175

Lys Pro Gly Gln Ala Pro Arg Leu Leu Ile Tyr Pro Ala Ser Asn Gln
            180                 185                 190

Gly Ser Gly Ile Pro Ala Arg Phe Ser Gly Ser Gly Ser Gly Thr Asp
            195                 200                 205

Phe Thr Leu Thr Ile Ser Ser Leu Glu Pro Glu Asp Phe Ala Val Tyr
            210                 215                 220

Tyr Cys Gln Gln Ser Lys Glu Val Pro Trp Thr Phe Gly Gln Gly Thr
225                 230                 235                 240

Lys Val Glu Ile Lys Gly Ser Gly Asp Tyr Lys Asp Asp Asp Lys
            245                 250                 255

Gly Ser Gly His His His His His His
            260                 265

<210> SEQ ID NO 232
<211> LENGTH: 265
<212> TYPE: PRT
<213> ORGANISM: Artificial Sequence
<220> FEATURE:
<223> OTHER INFORMATION: Synthetic: h4B10-2, scFv

<400> SEQUENCE: 232

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Thr Phe Ser Thr
            20                  25                  30

Tyr Gly Met Ser Trp Val Arg Gln Ala Pro Gly Lys Gly Leu Glu Trp
        35                  40                  45

Val Ala Thr Ile Ser Gly Gly Gly Ser Asn Thr Tyr Tyr Ser Asp Ser
    50                  55                  60

Val Lys Gly Arg Phe Thr Ile Ser Arg Asp Asp Ser Lys Asn Thr Leu
65                  70                  75                  80

Tyr Leu Gln Met Asn Ser Leu Lys Thr Glu Asp Thr Ala Val Tyr Tyr
                85                  90                  95

Cys Ala Arg Gln Arg Asp Ser Ala Trp Phe Ala Ser Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Glu Ile Val Leu Thr Gln Ser Pro Gly Thr
    130                 135                 140

Leu Ser Leu Ser Pro Gly Glu Arg Ala Thr Leu Ser Cys Arg Ala Ser
145                 150                 155                 160

Glu Asn Val Asp Asp Tyr Gly Val Ser Phe Met Asn Trp Tyr Gln Gln
                165                 170                 175

Lys Pro Gly Gln Ala Pro Arg Leu Leu Ile Tyr Pro Ala Ser Asn Gln
            180                 185                 190

Gly Ser Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Ser Lys Glu Val Pro Trp Thr Phe Gly Gln Gly Thr
225                 230                 235                 240

Lys Val Glu Ile Lys Gly Ser Gly Asp Tyr Lys Asp Asp Asp Asp Lys
                245                 250                 255

Gly Ser Gly His His His His His His
            260                 265

<210> SEQ ID NO 233
<211> LENGTH: 265
<212> TYPE: PRT
<213> ORGANISM: Artificial Sequence
<220> FEATURE:
<223> OTHER INFORMATION: Synthetic: h4B10-3, scFv

<400> SEQUENCE: 233

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Thr Phe Ser Thr
            20                  25                  30

Tyr Gly Met Ser Trp Val Arg Gln Ala Pro Gly Lys Gly Leu Glu Trp

```
                35                  40                  45
Val Ala Thr Ile Ser Gly Gly Ser Asn Thr Tyr Tyr Ser Asp Ser
 50                  55                  60

Val Lys Gly Arg Phe Thr Ile Ser Arg Asp Asp Ser Lys Asn Thr Leu
 65                  70                  75                  80

Tyr Leu Gln Met Asn Ser Leu Lys Thr Glu Asp Thr Ala Val Tyr Tyr
                 85                  90                  95

Cys Ala Arg Gln Arg Asp Ser Ala Trp Phe Ala Ser Trp Gly Gln Gly
                100                 105                 110

Thr Leu Val Thr Val Ser Ser Gly Gly Gly Ser Gly Gly Gly Gly
                115                 120                 125

Ser Gly Gly Gly Ser Asp Ile Val Met Thr Gln Ser Pro Asp Ser
130                 135                 140

Leu Ala Val Ser Leu Gly Glu Arg Ala Thr Ile Asn Cys Arg Ala Ser
145                 150                 155                 160

Glu Asn Val Asp Asp Tyr Gly Val Ser Phe Met Asn Trp Tyr Gln Gln
                165                 170                 175

Lys Pro Gly Gln Pro Pro Lys Leu Leu Ile Tyr Pro Ala Ser Asn Gln
                180                 185                 190

Gly Ser Gly Val Pro Asp Arg Phe Ser Gly Ser Gly Ser Gly Thr Asp
                195                 200                 205

Phe Thr Leu Thr Ile Ser Ser Leu Gln Ala Glu Asp Val Ala Val Tyr
                210                 215                 220

Tyr Cys Gln Gln Ser Lys Glu Val Pro Trp Thr Phe Gly Gly Gly Thr
225                 230                 235                 240

Lys Leu Glu Ile Lys Gly Ser Gly Asp Tyr Lys Asp Asp Asp Asp Lys
                245                 250                 255

Gly Ser Gly His His His His His His
                260                 265

<210> SEQ ID NO 234
<211> LENGTH: 262
<212> TYPE: PRT
<213> ORGANISM: Artificial Sequence
<220> FEATURE:
<223> OTHER INFORMATION: Synthetic: m10B4, scFv

<400> SEQUENCE: 234

Met Gln Val Gln Leu Gln Gln Ser Gly Ala Glu Leu Met Lys Pro Gly
 1               5                  10                  15

Ala Ser Val Lys Met Ser Cys Lys Thr Thr Gly Tyr Ile Phe Ser Ser
                 20                  25                  30

Tyr Trp Ile Gly Trp Val Lys Gln Arg Pro Gly His Gly Leu Glu Trp
             35                  40                  45

Ile Gly Lys Ile Phe Pro Gly Ser Gly Ser Ala Asp Tyr Asn Glu Asn
 50                  55                  60

Phe Lys Gly Lys Ala Thr Phe Thr Val Asp Thr Ser Ser Asn Thr Ala
 65                  70                  75                  80

Tyr Met Gln Leu Ser Ser Leu Thr Ser Glu Asp Ser Ala Val Tyr Tyr
                 85                  90                  95

Cys Ala Arg Gly Tyr Gly Asn Tyr Leu Tyr Phe Asp Val Trp Gly Ala
                100                 105                 110

Gly Thr Thr Val Thr Val Ser Ser Gly Gly Gly Gly Ser Gly Gly Gly
                115                 120                 125

Gly Ser Gly Gly Gly Gly Ser Asn Ile Val Met Thr Gln Thr Pro Lys
```

```
            130                 135                 140
Phe Leu Leu Val Ser Ala Gly Asp Arg Ile Thr Ile Thr Cys Lys Ala
145                 150                 155                 160

Ser Gln Ser Val Ser Asp Val Ala Trp Tyr Gln Lys Pro Gly
                165                 170                 175

Gln Ser Pro Lys Leu Leu Ile Ser Tyr Ala Phe Lys Arg Tyr Ile Gly
            180                 185                 190

Val Pro Asp Arg Phe Thr Gly Ser Gly Tyr Gly Thr Asp Phe Thr Phe
            195                 200                 205

Thr Ile Ser Thr Val Gln Ala Glu Asp Leu Ala Val Tyr Phe Cys Gln
            210                 215                 220

Gln Asn Tyr Asn Ser Pro Tyr Thr Phe Gly Gly Gly Thr Lys Leu Glu
225                 230                 235                 240

Leu Lys Gly Ser Gly Asp Tyr Lys Asp Asp Asp Lys Gly Ser Gly
                245                 250                 255

His His His His His His
            260

<210> SEQ ID NO 235
<211> LENGTH: 258
<212> TYPE: PRT
<213> ORGANISM: Artificial Sequence
<220> FEATURE:
<223> OTHER INFORMATION: Synthetic: m1B10, scFv

<400> SEQUENCE: 235

Met Ser Asp Val Gln Leu Gln Glu Ser Gly Pro Gly Leu Val Lys Pro
1               5                   10                  15

Ser Gln Ser Leu Ser Leu Thr Cys Thr Val Thr Gly His Ser Ile Thr
                20                  25                  30

Ser Asp Tyr Ala Trp Asn Trp Ile Arg Gln Phe Pro Gly Asn Lys Leu
            35                  40                  45

Glu Trp Met Gly Tyr Ile Ser Tyr Ser Gly Arg Thr Ser Tyr Asn Pro
    50                  55                  60

Ser Leu Thr Ser Arg Ile Ser Ile Thr Arg Asp Thr Ser Lys Asn Gln
65                  70                  75                  80

Phe Phe Leu Gln Leu Asn Ser Val Thr Thr Glu Asp Thr Ala Thr Tyr
                85                  90                  95

Tyr Cys Ala Arg Gly Tyr Ala Leu Asp Tyr Trp Gly Gln Gly Thr Ser
            100                 105                 110

Val Thr Val Ser Ser Gly Gly Gly Gly Ser Gly Gly Gly Gly Ser Gly
            115                 120                 125

Gly Gly Ser Gln Ile Val Leu Ser Gln Ser Pro Ala Ile Leu Ser
        130                 135                 140

Ala Ser Pro Gly Glu Lys Val Thr Met Thr Cys Arg Thr Ser Ser Ser
145                 150                 155                 160

Val Asn Tyr Met His Trp Phe Gln Gln Lys Pro Gly Ser Ser Pro Lys
                165                 170                 175

Pro Trp Ile Tyr Ala Thr Ser Lys Leu Ala Ser Gly Val Pro Ala Arg
            180                 185                 190

Phe Ser Gly Ser Gly Ser Gly Thr Ser Tyr Ser Leu Thr Ile Ser Arg
            195                 200                 205

Val Glu Ala Glu Asp Ala Ala Thr Tyr Phe Cys Gln Gln Trp Ile Ser
            210                 215                 220

Asp Pro Trp Thr Phe Gly Gly Gly Thr Lys Leu Glu Ile Lys Gly Ser
```

Gly Asp Tyr Lys Asp Asp Asp Lys Gly Ser Gly His His His His
                245             250             255

His His

<210> SEQ ID NO 236
<211> LENGTH: 267
<212> TYPE: PRT
<213> ORGANISM: Artificial Sequence
<220> FEATURE:
<223> OTHER INFORMATION: Synthetic: m1E9, scFv

<400> SEQUENCE: 236

Met Glu Val Lys Leu Val Glu Ser Gly Gly Gly Leu Val Ser Pro Gly
1               5                   10                  15

Gly Ser Leu Lys Leu Ser Cys Ala Ala Ser Gly Phe Thr Phe Ser Thr
                20                  25                  30

Phe Gly Met Ser Trp Val Arg Gln Thr Pro Glu Lys Arg Leu Glu Trp
            35                  40                  45

Val Ala Thr Ile Ser Gly Gly Ser Asp Thr Tyr Tyr Pro Asp Ser
        50                  55                  60

Val Gln Gly Arg Phe Ile Ile Ser Arg Tyr Asn Ala Lys Asn Asn Leu
65                  70                  75                  80

Tyr Leu Gln Met Asn Ser Leu Arg Pro Glu Asp Thr Ala Leu Tyr Tyr
                85                  90                  95

Cys Ala Arg Gln Gly Tyr Asp Val Tyr Ser Trp Phe Ala Tyr Trp Gly
            100                 105                 110

Gln Gly Thr Leu Val Thr Val Ser Ala Gly Gly Gly Ser Gly Gly
            115                 120                 125

Gly Gly Ser Gly Gly Gly Ser Asp Ile Ile Leu Thr Gln Ser Pro
        130                 135                 140

Ala Ser Leu Ala Val Ser Leu Gly Gln Arg Ala Ala Ile Ser Cys Arg
145                 150                 155                 160

Ala Ser Glu Ser Val Asp Asn Ser Gly Ile Ser Phe Met Ser Trp Phe
                165                 170                 175

Gln Gln Lys Pro Gly Gln Pro Pro Lys Leu Leu Ile Tyr Thr Ala Ser
            180                 185                 190

Asn Gln Gly Ser Gly Val Pro Ala Arg Phe Ser Gly Ser Gly Ser Gly
        195                 200                 205

Thr Glu Phe Ser Leu Asn Ile His Pro Met Glu Glu Asp Asp Thr Ala
    210                 215                 220

Met Tyr Phe Cys Gln Gln Ser Lys Glu Val Pro Trp Thr Phe Gly Gly
225                 230                 235                 240

Gly Thr Lys Leu Glu Ile Arg Gly Ser Gly Asp Tyr Lys Asp Asp Asp
                245                 250                 255

Asp Lys Gly Ser Gly His His His His His His
            260                 265

<210> SEQ ID NO 237
<211> LENGTH: 265
<212> TYPE: PRT
<213> ORGANISM: Artificial Sequence
<220> FEATURE:
<223> OTHER INFORMATION: Synthetic: m4B10, scFv

<400> SEQUENCE: 237

Met Glu Val Lys Leu Val Glu Ser Gly Gly Gly Leu Val Lys Pro Gly

```
                1               5                  10                 15
            Gly Ser Leu Lys Leu Ser Cys Ala Ala Ser Gly Phe Thr Phe Ser Thr
                            20                  25                  30

Tyr Gly Met Ser Trp Val Arg Gln Thr Pro Glu Lys Arg Leu Gln Trp
                            35                  40                  45

Val Ala Thr Ile Ser Gly Gly Gly Ser Asn Thr Tyr Tyr Ser Asp Ser
                50                      55                  60

Val Lys Gly Arg Phe Thr Ile Ser Arg Asp Asn Ala Lys Asn Asn Leu
             65                 70                  75                  80

Tyr Leu Gln Met Ser Ser Leu Arg Ser Glu Asp Thr Ala Leu Tyr Tyr
                            85                  90                  95

Cys Ala Arg Gln Arg Asp Ser Ala Trp Phe Ala Ser Trp Gly Gln Gly
                            100                 105                 110

Thr Leu Val Thr Val Ser Ala Gly Gly Gly Ser Gly Gly Gly Gly
                            115                 120                 125

Ser Gly Gly Gly Ser Asp Ile Val Leu Thr Gln Ser Pro Ala Ser
                    130                 135                 140

Leu Ala Val Ser Leu Gly Gln Arg Ala Thr Ile Ser Cys Arg Ala Ser
            145                 150                 155                 160

Glu Asn Val Asp Asp Tyr Gly Val Ser Phe Met Asn Trp Phe Gln Gln
                            165                 170                 175

Lys Pro Gly Gln Pro Pro Lys Leu Leu Ile Tyr Pro Ala Ser Asn Gln
                            180                 185                 190

Gly Ser Gly Val Pro Ala Arg Phe Ser Gly Ser Gly Ser Gly Thr Asp
                            195                 200                 205

Phe Ser Leu Asn Ile His Pro Met Glu Glu Asp Asp Thr Ala Met Tyr
                    210                 215                 220

Phe Cys Gln Gln Ser Lys Glu Val Pro Trp Thr Phe Gly Gly Gly Thr
            225                 230                 235                 240

Lys Leu Glu Ile Lys Gly Ser Gly Asp Tyr Lys Asp Asp Asp Asp Lys
                            245                 250                 255

Gly Ser Gly His His His His His His
                            260                 265

<210> SEQ ID NO 238
<211> LENGTH: 512
<212> TYPE: PRT
<213> ORGANISM: Artificial Sequence
<220> FEATURE:
<223> OTHER INFORMATION: Synthetic: 1353-A09, scFv-Fc

<400> SEQUENCE: 238

Met Glu Val Gln Leu Val Gln Ser Gly Ala Glu Val Lys Lys Pro Gly
             1                  5                  10                  15

Ala Ser Val Lys Val Ser Cys Lys Ala Ser Gly Tyr Arg Phe Thr Trp
                            20                  25                  30

Tyr Gly Ile Ser Trp Val Arg Gln Ala Pro Gly Gln Gly Leu Glu Trp
                            35                  40                  45

Met Gly Trp Ile Ser Ala Tyr Asn Gly Asn Thr Asn Tyr Ala Gln Lys
                50                      55                  60

Leu Gln Gly Arg Val Thr Met Thr Thr Asp Thr Ser Asn Thr Ala
             65                 70                  75                  80

Tyr Met Glu Leu Arg Ser Leu Arg Ser Asp Asp Thr Ala Val Tyr Tyr
                            85                  90                  95

Cys Ala Arg Asp Ser Glu Tyr Ser Ser Gly Ser Gly Tyr Trp Gly Gln
```

```
                100                 105                 110
Gly Thr Leu Val Thr Val Ser Ser Gly Gly Gly Ser Gly Gly Gly
            115                 120                 125
Gly Ser Gly Gly Gly Ser Ser Tyr Glu Leu Thr Gln Pro Pro Ser
            130                 135                 140
Val Ser Val Ser Pro Gly Gln Thr Ala Arg Ile Thr Cys Ser Gly Asp
145                 150                 155                 160
Ala Leu Thr Thr Gln Tyr Ala Tyr Trp Tyr Gln Gln Lys Pro Gly Gln
                165                 170                 175
Ala Pro Val Met Val Ile Tyr Lys Asp Thr Glu Arg Pro Ser Gly Ile
                180                 185                 190
Pro Glu Arg Phe Ser Gly Ser Ser Ser Gly Thr Lys Val Thr Leu Thr
                195                 200                 205
Ile Ser Gly Val Gln Ala Glu Asp Glu Ala Asp Tyr Tyr Cys Gln Ser
                210                 215                 220
Ala Asp Asn Ser Ile Thr Tyr Arg Val Phe Gly Gly Gly Thr Lys Val
225                 230                 235                 240
Thr Val Leu Ala Ala Gly Ser Asp Gln Glu Pro Lys Lys Leu Ala Ala
                245                 250                 255
Gly Ser Asp Gln Glu Pro Lys Ser Ser Asp Lys Thr His Thr Cys Pro
                260                 265                 270
Pro Cys Ser Ala Pro Glu Leu Leu Gly Gly Ser Ser Val Phe Leu Phe
                275                 280                 285
Pro Pro Lys Pro Lys Asp Thr Leu Met Ile Ser Arg Thr Pro Glu Val
                290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
                340                 345                 350
Val Leu His Gln Asp Trp Leu Asn Gly Lys Glu Tyr Lys Cys Lys Val
                355                 360                 365
Ser Asn Lys Ala Leu Pro Ala Pro Ile Glu Lys Thr Ile Ser Lys Ala
                370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
                420                 425                 430
Glu Asn Asn Tyr Lys Thr Thr Pro Pro Val Leu Asp Ser Asp Gly Ser
                435                 440                 445
Phe Phe Leu Tyr Ser Lys Leu Thr Val Asp Lys Ser Arg Trp Gln Gln
                450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Gly Ser Gly Asp
                485                 490                 495
Tyr Lys Asp Asp Asp Asp Lys Gly Ser Gly His His His His His His
                500                 505                 510

<210> SEQ ID NO 239
```

```
<211> LENGTH: 512
<212> TYPE: PRT
<213> ORGANISM: Artificial Sequence
<220> FEATURE:
<223> OTHER INFORMATION: Synthetic: 1353-C07, scFv-Fc

<400> SEQUENCE: 239
```

Met Glu Val Gln Leu Val Gln Ser Gly Ala Glu Val Lys Lys Pro Gly
1               5                   10                  15

Ala Ser Val Lys Val Ser Cys Lys Ala Ser Gly Tyr Arg Phe Ser Thr
            20                  25                  30

Phe Gly Ile Ser Trp Val Arg Gln Ala Pro Gly Gln Gly Leu Glu Trp
        35                  40                  45

Met Gly Trp Ile Ser Ala Tyr Asn Gly Asn Thr Asn Tyr Ala Gln Lys
    50                  55                  60

Leu Gln Gly Arg Val Thr Met Thr Thr Asp Thr Ser Asn Thr Ala
65                  70                  75                  80

Tyr Met Glu Leu Arg Ser Leu Arg Ser Asp Asp Thr Ala Val Tyr Tyr
                85                  90                  95

Cys Ala Arg Asp Val Asp Tyr Ser Ser Gly Ser Gly Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Tyr Glu Leu Thr Gln Pro Pro Ser
    130                 135                 140

Val Ser Val Ser Pro Gly Gln Thr Ala Arg Ile Thr Cys Ser Gly Asp
145                 150                 155                 160

Ala Leu Ser Glu Gln Tyr Ala Tyr Trp Tyr Gln Gln Lys Pro Gly Gln
                165                 170                 175

Ala Pro Val Met Val Ile Tyr Lys Asp Thr Glu Arg Pro Ser Gly Ile
            180                 185                 190

Pro Glu Arg Phe Ser Gly Ser Ser Ser Gly Thr Lys Val Thr Leu Thr
        195                 200                 205

Ile Ser Gly Val Gln Ala Glu Asp Glu Ala Asp Tyr Tyr Cys Gln Ser
    210                 215                 220

Ala Asp Asn Ser Ile Thr Tyr Arg Val Phe Gly Gly Gly Thr Lys Val
225                 230                 235                 240

Thr Val Leu Ala Ala Gly Ser Asp Gln Glu Pro Lys Lys Leu Ala Ala
                245                 250                 255

Gly Ser Asp Gln Glu Pro Lys Ser Ser Asp Lys Thr His Thr Cys Pro
            260                 265                 270

Pro Cys Ser Ala Pro Glu Leu Leu Gly Gly Ser Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

```
Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
            405                 410                 415

Phe Tyr Pro Ser Asp Ile Ala Val Glu Trp Glu Ser Asn Gly Gln Pro
        420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
        450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Gly Ser Gly Asp
            485                 490                 495

Tyr Lys Asp Asp Asp Asp Lys Gly Ser Gly His His His His His His
        500                 505                 510

<210> SEQ ID NO 240
<211> LENGTH: 512
<212> TYPE: PRT
<213> ORGANISM: Artificial Sequence
<220> FEATURE:
<223> OTHER INFORMATION: Synthetic: 1353-E07, scFv-Fc

<400> SEQUENCE: 240

Met Glu Val Gln Leu Val Gln Ser Gly Ala Glu Val Lys Lys Pro Gly
1               5                   10                  15

Ala Ser Val Lys Val Ser Cys Lys Ala Ser Gly Tyr Arg Phe Glu Thr
            20                  25                  30

Tyr Gly Ile Ser Trp Val Arg Gln Ala Pro Gly Gln Gly Leu Glu Trp
        35                  40                  45

Met Gly Trp Ile Ser Ala Tyr Asn Gly Asn Thr Asn Tyr Ala Gln Lys
    50                  55                  60

Leu Gln Gly Arg Val Thr Met Thr Thr Asp Thr Ser Thr Asn Thr Ala
65                  70                  75                  80

Tyr Met Glu Leu Arg Ser Leu Arg Ser Asp Asp Thr Ala Val Tyr Tyr
                85                  90                  95

Cys Ala Arg Asp Ala Glu Tyr Ser Leu Gly Ser Gly Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Tyr Glu Leu Thr Gln Pro Pro Ser
    130                 135                 140

Val Ser Val Ser Pro Gly Gln Thr Ala Arg Ile Thr Cys Ser Gly Asp
145                 150                 155                 160

Ala Leu Pro Lys Gln Tyr Ala Tyr Trp Tyr Gln Gln Lys Pro Gly Gln
                165                 170                 175

Ala Pro Val Met Val Ile Tyr Lys Asp Thr Glu Arg Pro Ser Gly Ile
            180                 185                 190

Pro Glu Arg Phe Ser Gly Ser Ser Ser Gly Thr Lys Val Thr Leu Thr
        195                 200                 205

Ile Ser Gly Val Gln Ala Glu Asp Glu Ala Asp Tyr Tyr Cys Gln Ser
    210                 215                 220

Ala Asp Asn Ser Ile Thr Tyr Arg Val Phe Gly Gly Gly Thr Lys Val
225                 230                 235                 240
```

Thr Val Leu Ala Ala Gly Ser Asp Gln Glu Pro Lys Leu Ala Ala
                245                 250                 255

Gly Ser Asp Gln Glu Pro Lys Ser Ser Asp Lys Thr His Thr Cys Pro
            260                 265                 270

Pro Cys Ser Ala Pro Glu Leu Leu Gly Gly Ser Ser Val Phe Leu Phe
        275                 280                 285

Pro Pro Lys Pro Lys Asp Thr Leu Met Ile Ser Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Gly Ser Gly Asp
                485                 490                 495

Tyr Lys Asp Asp Asp Lys Gly Ser Gly His His His His
            500                 505                 510

<210> SEQ ID NO 241
<211> LENGTH: 512
<212> TYPE: PRT
<213> ORGANISM: Artificial Sequence
<220> FEATURE:
<223> OTHER INFORMATION: Synthetic: 1353-F09, scFv-Fc

<400> SEQUENCE: 241

Met Glu Val Gln Leu Val Gln Ser Gly Ala Glu Val Lys Lys Pro Gly
1               5                   10                  15

Ala Ser Val Lys Val Ser Cys Lys Ala Ser Gly Tyr Arg Phe Arg Gln
            20                  25                  30

Tyr Gly Ile Ser Trp Val Arg Gln Ala Pro Gly Gln Gly Leu Glu Trp
        35                  40                  45

Met Gly Trp Ile Ser Ala Tyr Asn Gly Asn Thr Asn Tyr Ala Gln Lys
    50                  55                  60

Leu Gln Gly Arg Val Thr Met Thr Thr Asp Thr Ser Thr Asn Thr Ala
65                  70                  75                  80

Tyr Met Glu Leu Arg Ser Leu Arg Ser Asp Asp Thr Ala Val Tyr Tyr
                85                  90                  95

-continued

```
Cys Ala Arg Asp Ala Glu Tyr Gly Ser Gly Ser Gly Tyr Trp Gly Gln
            100                 105                 110
Gly Thr Leu Val Thr Val Ser Gly Gly Gly Ser Gly Gly Gly
        115                 120                 125
Gly Ser Gly Gly Gly Ser Ser Tyr Glu Leu Thr Gln Pro Pro Ser
    130                 135                 140
Val Ser Val Ser Pro Gly Gln Thr Ala Arg Ile Thr Cys Ser Gly Asp
145                 150                 155                 160
Ala Leu Pro Lys Gln Tyr Ala Tyr Trp Tyr Gln Gln Lys Pro Gly Gln
                165                 170                 175
Ala Pro Val Met Val Leu Tyr Lys Asp Thr Glu Arg Pro Ser Gly Ile
            180                 185                 190
Pro Glu Arg Phe Ser Gly Ser Ser Ser Gly Thr Lys Val Thr Leu Thr
        195                 200                 205
Ile Ser Gly Val Gln Ala Glu Asp Glu Ala Asp Tyr Tyr Cys Gln Ser
    210                 215                 220
Ala Asp Asn Ser Ile Thr Tyr Arg Val Phe Gly Gly Gly Thr Lys Val
225                 230                 235                 240
Thr Val Leu Ala Ala Gly Ser Asp Gln Glu Pro Lys Lys Leu Ala Ala
                245                 250                 255
Gly Ser Asp Gln Glu Pro Lys Ser Ser Asp Lys Thr His Thr Cys Pro
            260                 265                 270
Pro Cys Ser Ala Pro Glu Leu Leu Gly Gly Ser Ser Val Phe Leu Phe
        275                 280                 285
Pro Pro Lys Pro Lys Asp Thr Leu Met Ile Ser Arg Thr Pro Glu Val
    290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
            340                 345                 350
Val Leu His Gln Asp Trp Leu Asn Gly Lys Glu Tyr Lys Cys Lys Val
        355                 360                 365
Ser Asn Lys Ala Leu Pro Ala Pro Ile Glu Lys Thr Ile Ser Lys Ala
    370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
        435                 440                 445
Phe Phe Leu Tyr Ser Lys Leu Thr Val Asp Lys Ser Arg Trp Gln Gln
    450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Gly Ser Gly Asp
                485                 490                 495
Tyr Lys Asp Asp Asp Asp Lys Gly Ser Gly His His His His His His
            500                 505                 510
```

<210> SEQ ID NO 242
<211> LENGTH: 512
<212> TYPE: PRT
<213> ORGANISM: Artificial Sequence
<220> FEATURE:
<223> OTHER INFORMATION: Synthetic: 1353-G08, scFv-Fc

<400> SEQUENCE: 242

```
Met Glu Val Gln Leu Val Gln Ser Gly Ala Glu Val Lys Lys Pro Gly
1               5                   10                  15

Ala Ser Val Lys Val Ser Cys Lys Ala Ser Gly Tyr Arg Phe Thr Arg
            20                  25                  30

Tyr Gly Ile Ser Trp Val Arg Gln Ala Pro Gly Gln Gly Leu Glu Trp
        35                  40                  45

Met Gly Trp Val Ser Ala His Asn Gly Asn Thr Asn Tyr Ala Gln Lys
    50                  55                  60

Leu Gln Gly Arg Val Thr Met Thr Thr Asp Thr Ser Thr Asn Thr Ala
65                  70                  75                  80

Tyr Met Glu Leu Arg Ser Leu Arg Ser Asp Asp Thr Ala Val Tyr Tyr
                85                  90                  95

Cys Ala Arg Asp Ala Asp Tyr Gly Ser Gly Ser Gly Tyr Trp Gly Gln
            100                 105                 110

Gly Thr Leu Val Thr Val Ser Ser Gly Gly Gly Val Ser Gly Gly Gly
        115                 120                 125

Gly Ser Gly Gly Gly Gly Ser Ser Tyr Glu Leu Thr Gln Pro Pro Ser
    130                 135                 140

Val Ser Val Ser Pro Gly Gln Thr Ala Arg Ile Thr Cys Ser Gly Asp
145                 150                 155                 160

Ala Leu Pro Met Gln Tyr Gly Tyr Trp Tyr Gln Gln Lys Pro Gly Gln
                165                 170                 175

Ala Pro Val Met Val Ile Tyr Lys Asp Thr Glu Arg Pro Ser Gly Ile
            180                 185                 190

Pro Glu Arg Phe Ser Gly Ser Ser Ser Gly Thr Lys Val Thr Leu Thr
        195                 200                 205

Ile Ser Gly Val Gln Ala Glu Asp Glu Ala Asp Tyr Tyr Cys Gln Ser
    210                 215                 220

Ala Asp Asn Ser Ile Thr Tyr Arg Val Phe Gly Gly Gly Thr Lys Val
225                 230                 235                 240

Thr Val Leu Ala Ala Gly Ser Asp Gln Glu Pro Lys Lys Leu Ala Ala
                245                 250                 255

Gly Ser Asp Gln Glu Pro Lys Ser Ser Asp Lys Thr His Thr Cys Pro
            260                 265                 270

Pro Cys Ser Ala Pro Glu Leu Leu Gly Gly Ser Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365
```

```
Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Gly Ser Gly Asp
                485                 490                 495

Tyr Lys Asp Asp Asp Asp Lys Gly Ser Gly His His His His His His
            500                 505                 510
```

<210> SEQ ID NO 243
<211> LENGTH: 512
<212> TYPE: PRT
<213> ORGANISM: Artificial Sequence
<220> FEATURE:
<223> OTHER INFORMATION: Synthetic: 1353-G10, scFv-Fc

<400> SEQUENCE: 243

```
Met Glu Val Gln Leu Val Gln Ser Gly Ala Glu Val Lys Lys Pro Gly
1               5                   10                  15

Ala Ser Val Lys Val Ser Cys Lys Ala Ser Gly Tyr Arg Phe Pro His
            20                  25                  30

Tyr Gly Ile Ser Trp Val Arg Gln Ala Pro Gly Gln Gly Leu Glu Trp
        35                  40                  45

Met Gly Trp Ile Ser Ala Tyr Asn Gly Asn Thr Asn Tyr Ala Gln Lys
    50                  55                  60

Leu Gln Gly Arg Val Thr Met Thr Thr Asp Thr Ser Asn Thr Ala
65                  70                  75                  80

Tyr Met Glu Leu Arg Ser Leu Arg Ser Asp Asp Thr Ala Val Tyr Tyr
                85                  90                  95

Cys Ala Arg Asp Val Asp Tyr Gly Thr Gly Ser Gly Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Tyr Glu Leu Thr Gln Pro Pro Ser
    130                 135                 140

Val Ser Val Ser Pro Gly Gln Thr Ala Arg Ile Thr Cys Ser Gly Asp
145                 150                 155                 160

Ala Leu Pro Lys Gln Tyr Ala Tyr Trp Tyr Gln Gln Lys Pro Gly Gln
                165                 170                 175

Ala Pro Val Met Val Ile Tyr Lys Asp Thr Glu Arg Pro Ser Gly Ile
            180                 185                 190

Pro Glu Arg Phe Ser Gly Ser Ser Ser Gly Thr Lys Val Thr Leu Thr
        195                 200                 205

Ile Ser Gly Val Gln Ala Glu Asp Glu Ala Asp Tyr Tyr Cys Gln Ser
    210                 215                 220
```

Ala Asp Asn Ser Ile Thr Tyr Arg Val Phe Gly Gly Gly Thr Lys Val
225                 230                 235                 240

Thr Val Leu Ala Ala Gly Ser Asp Gln Glu Pro Lys Lys Leu Ala Ala
            245                 250                 255

Gly Ser Asp Gln Glu Pro Lys Ser Ser Asp Lys Thr His Thr Cys Pro
            260                 265                 270

Pro Cys Ser Ala Pro Glu Leu Leu Gly Gly Ser Ser Val Phe Leu Phe
            275                 280                 285

Pro Pro Lys Pro Lys Asp Thr Leu Met Ile Ser Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
                340                 345                 350

Val Leu His Gln Asp Trp Leu Asn Gly Lys Glu Tyr Lys Cys Lys Val
            355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Gly Ser Gly Asp
                485                 490                 495

Tyr Lys Asp Asp Asp Asp Lys Gly Ser Gly His His His His His His
            500                 505                 510

<210> SEQ ID NO 244
<211> LENGTH: 512
<212> TYPE: PRT
<213> ORGANISM: Artificial Sequence
<220> FEATURE:
<223> OTHER INFORMATION: Synthetic: 1353-H08, scFv-Fc

<400> SEQUENCE: 244

Met Glu Val Gln Leu Val Gln Ser Gly Ala Glu Val Lys Lys Pro Gly
1               5                   10                  15

Ala Ser Val Lys Val Ser Cys Lys Ala Ser Gly Tyr Arg Phe Thr Arg
            20                  25                  30

Gln Gly Ile Ser Trp Val Arg Gln Ala Pro Gly Gln Gly Leu Glu Trp
        35                  40                  45

Met Gly Trp Ile Ser Ala Tyr Asn Gly Asn Thr Lys Tyr Ala Gln Lys
    50                  55                  60

Leu Gln Gly Arg Val Thr Met Thr Thr Asp Thr Ser Thr Asn Thr Ala
65                  70                  75                  80

```
Tyr Met Glu Leu Arg Ser Leu Arg Ser Asp Thr Ala Val Tyr Tyr
             85                  90                  95
Cys Ala Arg Asp Val Asp Tyr Gly Ser Gly Ser Gly Tyr Trp Gly Gln
            100                 105                 110
Gly Thr Leu Val Thr Val Ser Ser Gly Gly Gly Gly Ser Gly Gly Gly
            115                 120                 125
Gly Ser Gly Gly Gly Gly Ser Ser Tyr Glu Leu Thr Gln Pro Pro Ser
            130                 135                 140
Val Ser Val Ser Pro Gly Gln Thr Ala Arg Ile Thr Cys Ser Gly Asp
145                 150                 155                 160
Ala Leu Pro Lys Gln Tyr Ala Tyr Trp Tyr Gln Gln Lys Pro Gly Gln
                165                 170                 175
Ala Pro Val Met Val Ile Tyr Lys Asp Thr Glu Arg Pro Ser Gly Ile
            180                 185                 190
Pro Glu Arg Phe Ser Gly Ser Ser Ser Gly Thr Lys Val Thr Leu Thr
            195                 200                 205
Ile Ser Gly Val Gln Ala Glu Asp Glu Ala Asp Tyr Tyr Cys Gln Ser
    210                 215                 220
Ala Asp Asn Ser Ile Thr Tyr Arg Val Phe Gly Gly Gly Thr Lys Val
225                 230                 235                 240
Thr Val Leu Ala Ala Gly Ser Asp Gln Glu Pro Lys Lys Leu Ala Ala
            245                 250                 255
Gly Ser Asp Gln Glu Pro Lys Ser Ser Asp Lys Thr His Thr Cys Pro
            260                 265                 270
Pro Cys Ser Ala Pro Glu Leu Leu Gly Gly Ser Ser Val Phe Leu Phe
            275                 280                 285
Pro Pro Lys Pro Lys Asp Thr Leu Met Ile Ser Arg Thr Pro Glu Val
            290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
            340                 345                 350
Val Leu His Gln Asp Trp Leu Asn Gly Lys Glu Tyr Lys Cys Lys Val
            355                 360                 365
Ser Asn Lys Ala Leu Pro Ala Pro Ile Glu Lys Thr Ile Ser Lys Ala
            370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
            435                 440                 445
Phe Phe Leu Tyr Ser Lys Leu Thr Val Asp Lys Ser Arg Trp Gln Gln
            450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Gly Ser Gly Asp
                485                 490                 495
Tyr Lys Asp Asp Asp Asp Lys Gly Ser Gly His His His His His His
```

<210> SEQ ID NO 245
<211> LENGTH: 512
<212> TYPE: PRT
<213> ORGANISM: Artificial Sequence
<220> FEATURE:
<223> OTHER INFORMATION: Synthetic: 1353-H09, scFv-Fc

<400> SEQUENCE: 245

Met Glu Val Gln Leu Val Gln Ser Gly Ala Glu Val Lys Lys Pro Gly
1               5                   10                  15

Ala Ser Val Lys Val Ser Cys Lys Ala Ser Gly Tyr Arg Phe Pro His
            20                  25                  30

Tyr Gly Ile Ser Trp Val Arg Gln Ala Pro Gly Gln Gly Leu Glu Trp
        35                  40                  45

Met Gly Trp Ile Ser Ala Tyr Asn Gly Asn Thr Asn Tyr Ala Gln Lys
    50                  55                  60

Leu Gln Gly Arg Val Thr Met Thr Thr Asp Thr Ser Thr Asn Thr Ala
65                  70                  75                  80

Tyr Met Glu Leu Arg Ser Leu Arg Ser Asp Asp Thr Ala Val Tyr Tyr
                85                  90                  95

Cys Ala Arg Asp Ala Glu Tyr Gly Ser Gly Ser Gly Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Tyr Glu Leu Thr Gln Pro Pro Ser
    130                 135                 140

Val Ser Val Ser Pro Gly Gln Thr Ala Arg Ile Thr Cys Ser Gly Asp
145                 150                 155                 160

Ala Leu Pro Lys Gln Tyr Ala Tyr Trp Tyr Gln Gln Lys Pro Gly Gln
                165                 170                 175

Ala Pro Val Met Val Ile Tyr Lys Asp Thr Glu Arg Pro Ser Gly Ile
            180                 185                 190

Pro Glu Arg Phe Ser Gly Ser Ser Ser Gly Thr Lys Val Thr Leu Thr
        195                 200                 205

Ile Ser Gly Val Gln Ala Glu Asp Glu Ala Asp Tyr Tyr Cys Gln Ser
    210                 215                 220

Ala Asp Asn Ser Ile Thr Tyr Arg Val Phe Gly Gly Gly Thr Lys Val
225                 230                 235                 240

Thr Val Leu Ala Ala Gly Ser Asp Gln Glu Pro Lys Ser Leu Ala Ala
                245                 250                 255

Gly Ser Asp Gln Glu Pro Lys Ser Ser Asp Lys Thr His Thr Cys Pro
            260                 265                 270

Pro Cys Ser Ala Pro Glu Leu Leu Gly Gly Ser Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val

```
                355                 360                 365
Ser Asn Lys Ala Leu Pro Ala Pro Ile Glu Lys Thr Ile Ser Lys Ala
            370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
                435                 440                 445
Phe Phe Leu Tyr Ser Lys Leu Thr Val Asp Lys Ser Arg Trp Gln Gln
            450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Gly Ser Gly Asp
                485                 490                 495
Tyr Lys Asp Asp Asp Asp Lys Gly Ser Gly His His His His His His
            500                 505                 510

<210> SEQ ID NO 246
<211> LENGTH: 119
<212> TYPE: PRT
<213> ORGANISM: Artificial Sequence
<220> FEATURE:
<223> OTHER INFORMATION: Synthetic: 10B4, VH

<400> SEQUENCE: 246

Gln Val Gln Leu Gln Gln Ser Gly Ala Glu Leu Met Lys Pro Gly Ala
1               5                   10                  15
Ser Val Lys Met Ser Cys Lys Thr Thr Gly Tyr Ile Phe Ser Ser Tyr
                20                  25                  30
Trp Ile Gly Trp Val Lys Gln Arg Pro Gly His Gly Leu Glu Trp Ile
            35                  40                  45
Gly Lys Ile Phe Pro Gly Ser Gly Ser Ala Asp Tyr Asn Glu Asn Phe
        50                  55                  60
Lys Gly Lys Ala Thr Phe Thr Val Asp Thr Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Ala Arg Gly Tyr Gly Asn Tyr Leu Tyr Phe Asp Val Trp Gly Ala Gly
                100                 105                 110
Thr Thr Val Thr Val Ser Ser
        115

<210> SEQ ID NO 247
<211> LENGTH: 119
<212> TYPE: PRT
<213> ORGANISM: Artificial Sequence
<220> FEATURE:
<223> OTHER INFORMATION: Synthetic: 1353-A09, VH

<400> SEQUENCE: 247

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Arg Phe Thr Trp Tyr
                20                  25                  30
```

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Glu Tyr Ser Ser Gly Ser Gly Tyr Trp Gly Gln Gly
                100                 105                 110

Thr Leu Val Thr Val Ser Ser
            115

<210> SEQ ID NO 248
<211> LENGTH: 119
<212> TYPE: PRT
<213> ORGANISM: Artificial Sequence
<220> FEATURE:
<223> OTHER INFORMATION: Synthetic: 1353-C07, VH

<400> SEQUENCE: 248

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Ser Thr Phe
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Asp Tyr Ser Ser Gly Ser Gly Tyr Trp Gly Gln Gly
                100                 105                 110

Thr Leu Val Thr Val Ser Ser
            115

<210> SEQ ID NO 249
<211> LENGTH: 119
<212> TYPE: PRT
<213> ORGANISM: Artificial Sequence
<220> FEATURE:
<223> OTHER INFORMATION: Synthetic: 1353-E07, VH

<400> SEQUENCE: 249

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Glu Thr Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Glu Tyr Ser Leu Gly Ser Gly Tyr Trp Gly Gln Gly
            100                 105                 110

Thr Leu Val Thr Val Ser Ser
        115

<210> SEQ ID NO 250
<211> LENGTH: 119
<212> TYPE: PRT
<213> ORGANISM: Artificial Sequence
<220> FEATURE:
<223> OTHER INFORMATION: Synthetic: 1353-F09, VH

<400> SEQUENCE: 250

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Arg Gln Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Thr Ala Val Tyr Tyr Cys
                85                  90                  95

Ala Arg Asp Ala Glu Tyr Gly Ser Gly Ser Gly Tyr Trp Gly Gln Gly
            100                 105                 110

Thr Leu Val Thr Val Ser Ser
        115

<210> SEQ ID NO 251
<211> LENGTH: 119
<212> TYPE: PRT
<213> ORGANISM: Artificial Sequence
<220> FEATURE:
<223> OTHER INFORMATION: Synthetic: 1353-G08, VH

<400> SEQUENCE: 251

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Arg Tyr
            20                  25                  30

Gly Ile Ser Trp Val Arg Gln Ala Pro Gly Gln Gly Leu Glu Trp Met
        35                  40                  45

Gly Trp Val Ser Ala His Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Thr Ala Val Tyr Tyr Cys
                85                  90                  95

Ala Arg Asp Ala Asp Tyr Gly Ser Gly Ser Gly Tyr Trp Gly Gln Gly
            100                 105                 110

Thr Leu Val Thr Val Ser Ser
        115

<210> SEQ ID NO 252
<211> LENGTH: 119
<212> TYPE: PRT

<213> ORGANISM: Artificial Sequence
<220> FEATURE:
<223> OTHER INFORMATION: Synthetic: 1353-G10, VH

<400> SEQUENCE: 252

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Arg Phe Pro His Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Asn Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Val Asp Tyr Gly Thr Gly Ser Gly Tyr Trp Gly Gln Gly
            100                 105                 110
Thr Leu Val Thr Val Ser Ser
        115

<210> SEQ ID NO 253
<211> LENGTH: 119
<212> TYPE: PRT
<213> ORGANISM: Artificial Sequence
<220> FEATURE:
<223> OTHER INFORMATION: Synthetic: 1353-H08, VH

<400> SEQUENCE: 253

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Arg Phe Thr Arg Gln
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Lys Tyr Ala Gln Lys Leu
    50                  55                  60
Gln Gly Arg Val Thr Met Thr Thr Asp Thr Ser Thr Asn Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Val Asp Tyr Gly Ser Gly Ser Gly Tyr Trp Gly Gln Gly
            100                 105                 110
Thr Leu Val Thr Val Ser Ser
        115

<210> SEQ ID NO 254
<211> LENGTH: 119
<212> TYPE: PRT
<213> ORGANISM: Artificial Sequence
<220> FEATURE:
<223> OTHER INFORMATION: Synthetic: 1353-H09, VH

<400> SEQUENCE: 254

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Arg Phe Pro His Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Glu Tyr Gly Ser Gly Ser Gly Tyr Trp Gly Gln Gly
                100                 105                 110

Thr Leu Val Thr Val Ser Ser
            115

<210> SEQ ID NO 255
<211> LENGTH: 115
<212> TYPE: PRT
<213> ORGANISM: Artificial Sequence
<220> FEATURE:
<223> OTHER INFORMATION: Synthetic: 1B10, VH

<400> SEQUENCE: 255

Asp Val Gln Leu Gln Glu Ser Gly Pro Gly Leu Val Lys Pro Ser Gln
1               5                   10                  15

Ser Leu Ser Leu Thr Cys Thr Val Thr Gly His Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Arg Thr Ser Tyr Asn Pro Ser Leu
    50                  55                  60

Thr Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Ala Leu Asp Tyr Trp Gly Gln Gly Thr Ser Val Thr
                100                 105                 110

Val Ser Ser
    115

<210> SEQ ID NO 256
<211> LENGTH: 120
<212> TYPE: PRT
<213> ORGANISM: Artificial Sequence
<220> FEATURE:
<223> OTHER INFORMATION: Synthetic: 1E9, VH

<400> SEQUENCE: 256

Glu Val Lys Leu Val Glu Ser Gly Gly Gly Leu Val Ser Pro Gly Gly
1               5                   10                  15

Ser Leu Lys Leu Ser Cys Ala Ala Ser Gly Phe Thr Phe Ser Thr Phe
            20                  25                  30

Gly Met Ser Trp Val Arg Gln Thr Pro Glu Lys Arg Leu Glu Trp Val
            35                  40                  45

Ala Thr Ile Ser Gly Gly Gly Ser Asp Thr Tyr Tyr Pro Asp Ser Val
    50                  55                  60

Gln Gly Arg Phe Ile Ile Ser Arg Tyr Asn Ala Lys Asn Asn Leu Tyr
65                  70                  75                  80

Leu Gln Met Asn Ser Leu Arg Pro Glu Asp Thr Ala Leu Tyr Tyr Cys 85                  90                  95

Ala Arg Gln Gly Tyr Asp Val Tyr Ser Trp Phe Ala Tyr Trp Gly Gln
            100                 105                 110

Gly Thr Leu Val Thr Val Ser Ala
        115                 120

<210> SEQ ID NO 257
<211> LENGTH: 118
<212> TYPE: PRT
<213> ORGANISM: Artificial Sequence
<220> FEATURE:
<223> OTHER INFORMATION: Synthetic: 4B10, VH

<400> SEQUENCE: 257

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Gly Met Ser Trp Val Arg Gln Thr Pro Glu Lys Arg Leu Gln Trp Val
        35                  40                  45

Ala Thr Ile Ser Gly Gly Gly Ser Asn Thr Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Gln Arg Asp Ser Ala Trp Phe Ala Ser Trp Gly Gln Gly Thr
            100                 105                 110

Leu Val Thr Val Ser Ala
        115

<210> SEQ ID NO 258
<211> LENGTH: 120
<212> TYPE: PRT
<213> ORGANISM: Artificial Sequence
<220> FEATURE:
<223> OTHER INFORMATION: Synthetic: h1E9-1, VH

<400> SEQUENCE: 258

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Gly Met Ser Trp Val Arg Gln Ala Pro Gly Lys Gly Leu Glu Trp Val
        35                  40                  45

Ser Thr Ile Ser Gly Gly Gly Ser Asp Thr Tyr Tyr Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Asp Val Tyr Ser Trp Phe Ala Tyr Trp Gly Gln
            100                 105                 110

Gly Thr Leu Val Thr Val Ser Ser
        115                 120

<210> SEQ ID NO 259
<211> LENGTH: 120

```
<212> TYPE: PRT
<213> ORGANISM: Artificial Sequence
<220> FEATURE:
<223> OTHER INFORMATION: Synthetic: h1E9-2, VH

<400> SEQUENCE: 259

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Gly Met Ser Trp Val Arg Gln Ala Pro Gly Lys Gly Leu Glu Trp Val
        35                  40                  45

Ser Thr Ile Ser Gly Gly Gly Ser Asp Thr Tyr Tyr Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Asp Val Tyr Ser Trp Phe Ala Tyr Trp Gly Gln
            100                 105                 110

Gly Thr Leu Val Thr Val Ser Ser
        115                 120

<210> SEQ ID NO 260
<211> LENGTH: 120
<212> TYPE: PRT
<213> ORGANISM: Artificial Sequence
<220> FEATURE:
<223> OTHER INFORMATION: Synthetic: h1E9-4, VH

<400> SEQUENCE: 260

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Gly Met Ser Trp Val Arg Gln Ala Pro Gly Lys Gly Leu Glu Trp Val
        35                  40                  45

Ala Thr Ile Ser Gly Gly Gly Ser Asp Thr Tyr Tyr Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Asp Val Tyr Ser Trp Phe Ala Tyr Trp Gly Gln
            100                 105                 110

Gly Thr Leu Val Thr Val Ser Ser
        115                 120

<210> SEQ ID NO 261
<211> LENGTH: 120
<212> TYPE: PRT
<213> ORGANISM: Artificial Sequence
<220> FEATURE:
<223> OTHER INFORMATION: Synthetic: h1E9-5, VH

<400> SEQUENCE: 261

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
```

-continued

```
                20                  25                  30
Gly Met Ser Trp Val Arg Gln Ala Pro Gly Lys Gly Leu Glu Trp Val
            35                  40                  45

Ala Thr Ile Ser Gly Gly Gly Ser Asp Thr Tyr Tyr Pro Asp Ser Val
        50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gln Gly Tyr Asp Val Tyr Ser Trp Phe Ala Tyr Trp Gly Gln
            100                 105                 110

Gly Thr Leu Val Thr Val Ser Ser
            115                 120

<210> SEQ ID NO 262
<211> LENGTH: 118
<212> TYPE: PRT
<213> ORGANISM: Artificial Sequence
<220> FEATURE:
<223> OTHER INFORMATION: Synthetic: h4B10-1, VH

<400> SEQUENCE: 262

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
            35                  40                  45

Ala Thr Ile Ser Gly Gly Gly Ser Asn Thr Tyr Tyr Ser Asp Ser Val
        50                  55                  60

Lys Gly Arg Phe Thr Ile Ser Arg Asp Asp Ser Lys Asn Thr Leu Tyr
 65                  70                  75                  80

Leu Gln Met Asn Ser Leu Lys Thr Glu Asp Thr Ala Val Tyr Tyr Cys
                85                  90                  95

Ala Arg Gln Arg Asp Ser Ala Trp Phe Ala Ser Trp Gly Gln Gly Thr
            100                 105                 110

Leu Val Thr Val Ser Ser
        115

<210> SEQ ID NO 263
<211> LENGTH: 118
<212> TYPE: PRT
<213> ORGANISM: Artificial Sequence
<220> FEATURE:
<223> OTHER INFORMATION: Synthetic: h4B10-2, VH

<400> SEQUENCE: 263

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
            35                  40                  45

Ala Thr Ile Ser Gly Gly Gly Ser Asn Thr Tyr Tyr Ser Asp Ser Val
        50                  55                  60

Lys Gly Arg Phe Thr Ile Ser Arg Asp Asp Ser Lys Asn Thr Leu Tyr
 65                  70                  75                  80
```

```
Leu Gln Met Asn Ser Leu Lys Thr Glu Asp Thr Ala Val Tyr Tyr Cys
                 85                  90                  95

Ala Arg Gln Arg Asp Ser Ala Trp Phe Ala Ser Trp Gly Gln Gly Thr
            100                 105                 110

Leu Val Thr Val Ser Ser
        115

<210> SEQ ID NO 264
<211> LENGTH: 118
<212> TYPE: PRT
<213> ORGANISM: Artificial Sequence
<220> FEATURE:
<223> OTHER INFORMATION: Synthetic: h4B10-3, VH

<400> SEQUENCE: 264

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Ser Asn Thr Tyr Tyr Ser Asp Ser Val
    50                  55                  60

Lys Gly Arg Phe Thr Ile Ser Arg Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Gln Arg Asp Ser Ala Trp Phe Ala Ser Trp Gly Gln Gly Thr
            100                 105                 110

Leu Val Thr Val Ser Ser
        115

<210> SEQ ID NO 265
<211> LENGTH: 128
<212> TYPE: PRT
<213> ORGANISM: Artificial Sequence
<220> FEATURE:
<223> OTHER INFORMATION: Synthetic: PD1-17, VH

<400> SEQUENCE: 265

Gln Val Gln Leu Gln Glu Ser Gly Pro Gly Val Val Lys Pro Ser Gly
1               5                   10                  15

Thr Leu Ser Leu Thr Cys Ala Ile Ser Gly Gly Ser Ile Gly Ser Gly
            20                  25                  30

Gly Ser Ile Arg Ser Thr Arg Trp Trp Ser Trp Val Arg Gln Ser Pro
        35                  40                  45

Gly Lys Gly Leu Glu Trp Ile Gly Glu Ile Tyr His Ser Gly Ser Thr
    50                  55                  60

Asn Tyr Asn Pro Ser Leu Lys Ser Arg Val Thr Ile Ser Leu Asp Lys
65                  70                  75                  80

Ser Arg Asn His Phe Ser Leu Arg Leu Asn Ser Val Thr Ala Ala Asp
                85                  90                  95

Thr Ala Val Tyr Tyr Cys Ala Arg Gln Asp Tyr Gly Asp Ser Gly Asp
            100                 105                 110

Trp Tyr Phe Asp Leu Trp Gly Lys Gly Thr Met Val Thr Val Ser Ser
        115                 120                 125

<210> SEQ ID NO 266
```

```
<211> LENGTH: 119
<212> TYPE: PRT
<213> ORGANISM: Artificial Sequence
<220> FEATURE:
<223> OTHER INFORMATION: Synthetic: PD1-28, VH

<400> SEQUENCE: 266
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Asp Tyr Ser Ser Gly Ser Gly Tyr Trp Gly Gln Gly
            100                 105                 110

Thr Leu Val Thr Val Ser Ser
        115

```
<210> SEQ ID NO 267
<211> LENGTH: 119
<212> TYPE: PRT
<213> ORGANISM: Artificial Sequence
<220> FEATURE:
<223> OTHER INFORMATION: Synthetic: PD1-33, VH

<400> SEQUENCE: 267
```

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Leu Thr Ser Tyr
            20                  25                  30

Tyr Ile His Trp Val Arg Gln Ala Pro Gly Gln Gly Leu Glu Trp Met
        35                  40                  45

Gly Ile Ile Asn Pro Arg Gly Ala Thr Ile Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Arg Asn Leu Lys Ser Glu Asp Thr Ala Leu Tyr Tyr Cys
                85                  90                  95

Ala Thr Ala Gly Ile Tyr Gly Phe Asp Phe Asp Tyr Trp Gly Arg Gly
            100                 105                 110

Thr Leu Val Thr Val Ser Ser
        115

```
<210> SEQ ID NO 268
<211> LENGTH: 127
<212> TYPE: PRT
<213> ORGANISM: Artificial Sequence
<220> FEATURE:
<223> OTHER INFORMATION: Synthetic: PD1-35, VH

<400> SEQUENCE: 268
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Ser Trp Ile Arg Gln His Pro Gly Lys Gly Leu Glu
            35                  40                  45

Trp Ile Gly Tyr Ile Tyr Tyr Asn Gly Asn Thr Tyr Tyr Asn Pro Ser
        50                  55                  60

Leu Arg Ser Leu Val Thr Ile Ser Val Asp Ala Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Ala Ser Asp Tyr Val Trp Gly Gly Tyr Tyr Met Asp
            100                 105                 110

Ala Phe Asp Ile Trp Gly Arg Gly Thr Leu Ile Thr Val Ser Ser
            115                 120                 125

<210> SEQ ID NO 269
<211> LENGTH: 121
<212> TYPE: PRT
<213> ORGANISM: Artificial Sequence
<220> FEATURE:
<223> OTHER INFORMATION: Synthetic: PD1-F2, VH

<400> SEQUENCE: 269

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Trp Cys Asp Arg Met Ser Trp Val Arg Gln Ala Pro Gly Lys Gly Leu
            35                  40                  45

Glu Trp Val Ser Ala Ile Ser Gly Ser Gly Gly Ser Thr Tyr Tyr Ala
        50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
            85                  90                  95

Tyr Tyr Cys Ala Lys Glu Asn Trp Gly Ser Tyr Phe Asp Leu Trp Gly
            100                 105                 110

Gln Gly Thr Thr Val Thr Val Ser Ser
            115                 120

<210> SEQ ID NO 270
<211> LENGTH: 108
<212> TYPE: PRT
<213> ORGANISM: Artificial Sequence
<220> FEATURE:
<223> OTHER INFORMATION: Synthetic: 10B4, VL

<400> SEQUENCE: 270

Asn Ile Val Met Thr Gln Thr Pro Lys Phe Leu Leu Val Ser Ala Gly
1               5                   10                  15

Asp Arg Ile Thr Ile Thr Cys Lys Ala Ser Gln Ser Val Ser Asp Asp
            20                  25                  30

Val Ala Trp Tyr Gln Gln Lys Pro Gly Gln Ser Pro Lys Leu Leu Ile
            35                  40                  45

Ser Tyr Ala Phe Lys Arg Tyr Ile Gly Val Pro Asp Arg Phe Thr Gly
        50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asn Tyr Asn Ser Pro Tyr
            85                  90                  95

Thr Phe Gly Gly Gly Thr Lys Leu Glu Leu Lys Arg
            100                 105

<210> SEQ ID NO 271
<211> LENGTH: 108
<212> TYPE: PRT
<213> ORGANISM: Artificial Sequence
<220> FEATURE:
<223> OTHER INFORMATION: Synthetic: 1353-A09, VL

<400> SEQUENCE: 271

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Thr Thr Gln Tyr Ala
            20                  25                  30

Tyr Trp Tyr Gln Gln Lys Pro Gly Gln Ala Pro Val Met Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105

<210> SEQ ID NO 272
<211> LENGTH: 108
<212> TYPE: PRT
<213> ORGANISM: Artificial Sequence
<220> FEATURE:
<223> OTHER INFORMATION: Synthetic: 1353-C07, VL

<400> SEQUENCE: 272

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Ser Glu Gln Tyr Ala
            20                  25                  30

Tyr Trp Tyr Gln Gln Lys Pro Gly Gln Ala Pro Val Met Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105

<210> SEQ ID NO 273
<211> LENGTH: 108
<212> TYPE: PRT
<213> ORGANISM: Artificial Sequence
<220> FEATURE:
<223> OTHER INFORMATION: Synthetic: 1353-E07, VL

<400> SEQUENCE: 273

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Met Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105

<210> SEQ ID NO 274
<211> LENGTH: 108
<212> TYPE: PRT
<213> ORGANISM: Artificial Sequence
<220> FEATURE:
<223> OTHER INFORMATION: Synthetic: 1353-F09, VL

<400> SEQUENCE: 274

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Met Val Leu Tyr
        35                  40                  45

Lys Asp Thr Glu Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105

<210> SEQ ID NO 275
<211> LENGTH: 108
<212> TYPE: PRT
<213> ORGANISM: Artificial Sequence
<220> FEATURE:
<223> OTHER INFORMATION: Synthetic: 1353-G08, VL

<400> SEQUENCE: 275

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Met Gln Tyr Gly
            20                  25                  30

Tyr Trp Tyr Gln Gln Lys Pro Gly Gln Ala Pro Val Met Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105

<210> SEQ ID NO 276
<211> LENGTH: 108
<212> TYPE: PRT
<213> ORGANISM: Artificial Sequence
<220> FEATURE:
<223> OTHER INFORMATION: Synthetic: 1353-G10, VL

<400> SEQUENCE: 276

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Met Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105

<210> SEQ ID NO 277
<211> LENGTH: 108
<212> TYPE: PRT
<213> ORGANISM: Artificial Sequence
<220> FEATURE:
<223> OTHER INFORMATION: Synthetic: 1353-H08, VL

<400> SEQUENCE: 277

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Met Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105

<210> SEQ ID NO 278
<211> LENGTH: 108
<212> TYPE: PRT
<213> ORGANISM: Artificial Sequence
<220> FEATURE:
<223> OTHER INFORMATION: Synthetic: 1353-H09, VL

<400> SEQUENCE: 278

Ser Tyr Glu Leu Thr Gln Pro Pro Ser Val Ser Val Ser Pro Gly Gln
1               5                   10                  15

```
Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Met Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105

<210> SEQ ID NO 279
<211> LENGTH: 106
<212> TYPE: PRT
<213> ORGANISM: Artificial Sequence
<220> FEATURE:
<223> OTHER INFORMATION: Synthetic: 1B10, VL

<400> SEQUENCE: 279

Gln Ile Val Leu Ser Gln Ser Pro Ala Ile Leu Ser Ala Ser Pro Gly
1               5                   10                  15

Glu Lys Val Thr Met Thr Cys Arg Thr Ser Ser Ser Val Asn Tyr Met
            20                  25                  30

His Trp Phe Gln Gln Lys Pro Gly Ser Ser Pro Lys Pro Trp Ile Tyr
        35                  40                  45

Ala Thr Ser Lys Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys Gln Gln Trp Ile Ser Asp Pro Trp Thr
                85                  90                  95

Phe Gly Gly Gly Thr Lys Leu Glu Ile Lys
            100                 105

<210> SEQ ID NO 280
<211> LENGTH: 111
<212> TYPE: PRT
<213> ORGANISM: Artificial Sequence
<220> FEATURE:
<223> OTHER INFORMATION: Synthetic: 1E9, VL

<400> SEQUENCE: 280

Asp Ile Ile Leu Thr Gln Ser Pro Ala Ser Leu Ala Val Ser Leu Gly
1               5                   10                  15

Gln Arg Ala Ala Ile Ser Cys Arg Ala Ser Glu Ser Val Asp Asn Ser
            20                  25                  30

Gly Ile Ser Phe Met Ser Trp Phe Gln Gln Lys Pro Gly Gln Pro Pro
        35                  40                  45

Lys Leu Leu Ile Tyr Thr Ala Ser Asn Gln Gly Ser Gly Val Pro Ala
    50                  55                  60

Arg Phe Ser Gly Ser Gly Ser Gly Thr Glu Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Arg
            100                 105                 110
```

<210> SEQ ID NO 281
<211> LENGTH: 111
<212> TYPE: PRT
<213> ORGANISM: Artificial Sequence
<220> FEATURE:
<223> OTHER INFORMATION: Synthetic: 4B10, VL

<400> SEQUENCE: 281

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Asn Val Asp Asp Tyr
            20                  25                  30

Gly Val Ser Phe Met Asn Trp Phe Gln Gln Lys Pro Gly Gln Pro Pro
        35                  40                  45

Lys Leu Leu Ile Tyr Pro Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 282
<211> LENGTH: 111
<212> TYPE: PRT
<213> ORGANISM: Artificial Sequence
<220> FEATURE:
<223> OTHER INFORMATION: Synthetic: h1E9-1, VL

<400> SEQUENCE: 282

Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Ser Val Asp Asn Ser
            20                  25                  30

Gly Ile Ser Phe Met Ser Trp Tyr Gln Gln Lys Pro Gly Lys Ala Pro
        35                  40                  45

Lys Leu Leu Ile Tyr Thr Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln Gln Ser Lys
                85                  90                  95

Glu Val Pro Trp Thr Phe Gly Gln Gly Thr Lys Val Glu Ile Lys
            100                 105                 110

<210> SEQ ID NO 283
<211> LENGTH: 111
<212> TYPE: PRT
<213> ORGANISM: Artificial Sequence
<220> FEATURE:
<223> OTHER INFORMATION: Synthetic: h1E9-2, VL

<400> SEQUENCE: 283

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Ser
            20                  25                  30

-continued

Gly Ile Ser Phe Met Ser Trp Tyr Gln Gln Lys Pro Gly Gln Ala Pro
            35                  40                  45

Arg Leu Leu Ile Tyr Thr Ala Ser Asn Gln Gly Ser Gly Ile Pro Ala
 50                      55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Lys
                 85                  90                  95

Glu Val Pro Trp Thr Phe Gly Gln Gly Thr Lys Val Glu Ile Lys
            100                 105                 110

<210> SEQ ID NO 284
<211> LENGTH: 111
<212> TYPE: PRT
<213> ORGANISM: Artificial Sequence
<220> FEATURE:
<223> OTHER INFORMATION: Synthetic: h1E9-4, VL

<400> SEQUENCE: 284

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Glu Ser Val Asp Asn Ser
             20                  25                  30

Gly Ile Ser Phe Met Ser Trp Tyr Gln Gln Lys Pro Gly Lys Ala Pro
            35                  40                  45

Lys Leu Leu Ile Tyr Thr Ala Ser Asn Gln Gly Ser Gly Val Pro Ser
 50                      55                  60

Arg Phe Ser Gly Ser Gly Ser Gly Thr Glu Phe Thr Leu Thr Ile Ser
 65                  70                  75                  80

Ser Leu Gln Pro Glu Asp Phe Ala Thr Tyr Tyr Cys Gln Gln Ser Lys
                 85                  90                  95

Glu Val Pro Trp Thr Phe Gly Gln Gly Thr Lys Val Glu Ile Lys
            100                 105                 110

<210> SEQ ID NO 285
<211> LENGTH: 111
<212> TYPE: PRT
<213> ORGANISM: Artificial Sequence
<220> FEATURE:
<223> OTHER INFORMATION: Synthetic: h1E9-5, VL

<400> SEQUENCE: 285

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Asp Asn Ser
             20                  25                  30

Gly Ile Ser Phe Met Ser Trp Tyr Gln Gln Lys Pro Gly Gln Ala Pro
            35                  40                  45

Arg Leu Leu Ile Tyr Thr Ala Ser Asn Gln Gly Ser Gly Ile Pro Ala
 50                      55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Lys
                 85                  90                  95

Glu Val Pro Trp Thr Phe Gly Gln Gly Thr Lys Val Glu Ile Lys
            100                 105                 110

<210> SEQ ID NO 286

<211> LENGTH: 111
<212> TYPE: PRT
<213> ORGANISM: Artificial Sequence
<220> FEATURE:
<223> OTHER INFORMATION: Synthetic: h4B10-1, VL

<400> SEQUENCE: 286

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Asp Asp Tyr
            20                  25                  30

Gly Val Ser Phe Met Asn Trp Tyr Gln Gln Lys Pro Gly Gln Ala Pro
        35                  40                  45

Arg Leu Leu Ile Tyr Pro Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Trp Thr Phe Gly Gln Gly Thr Lys Val Glu Ile Lys
            100                 105                 110
```

<210> SEQ ID NO 287
<211> LENGTH: 111
<212> TYPE: PRT
<213> ORGANISM: Artificial Sequence
<220> FEATURE:
<223> OTHER INFORMATION: Synthetic: h4B10-2, VL

<400> SEQUENCE: 287

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Asn Val Asp Asp Tyr
            20                  25                  30

Gly Val Ser Phe Met Asn Trp Tyr Gln Gln Lys Pro Gly Gln Ala Pro
        35                  40                  45

Arg Leu Leu Ile Tyr Pro Ala Ser Asn Gln Gly Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Val Glu Ile Lys
            100                 105                 110
```

<210> SEQ ID NO 288
<211> LENGTH: 111
<212> TYPE: PRT
<213> ORGANISM: Artificial Sequence
<220> FEATURE:
<223> OTHER INFORMATION: Synthetic: h4B10-3, VL

<400> SEQUENCE: 288

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Asn Val Asp Asp Tyr
            20                  25                  30

Gly Val Ser Phe Met Asn Trp Tyr Gln Gln Lys Pro Gly Gln Pro Pro
        35                  40                  45
```

```
Lys Leu Leu Ile Tyr Pro Ala Ser Asn Gln Gly Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Val Pro Trp Thr Phe Gly Gly Gly Thr Lys Leu Glu Ile Lys
                100                 105                 110

<210> SEQ ID NO 289
<211> LENGTH: 110
<212> TYPE: PRT
<213> ORGANISM: Artificial Sequence
<220> FEATURE:
<223> OTHER INFORMATION: Synthetic: PD1-17, VL

<400> SEQUENCE: 289

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                 20                  25                  30

Ser Val Gln Trp Tyr Gln Gln Arg Pro Gly Ser Ser Pro Thr Thr Val
             35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Val Ser Gly
 65                  70                  75                  80

Leu Lys Thr Glu Asp Glu Ala Asp Tyr Tyr Cys Gln Ser Ser Asp Ser
                 85                  90                  95

Ser Ala Val Val Phe Gly Ser Gly Thr Lys Leu Thr Val Leu
                100                 105                 110

<210> SEQ ID NO 290
<211> LENGTH: 108
<212> TYPE: PRT
<213> ORGANISM: Artificial Sequence
<220> FEATURE:
<223> OTHER INFORMATION: Synthetic: PD1-28, VL

<400> SEQUENCE: 290

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
                 20                  25                  30

Tyr Trp Tyr Gln Gln Lys Pro Gly Gln Ala Pro Val Met Val Ile Tyr
             35                  40                  45

Lys Asp Thr Glu Arg Pro Ser Gly Ile Pro Glu Arg Phe Ser Gly Ser
 50                  55                  60

Ser Ser Gly Thr Lys Val Thr Leu Thr Ile Ser Gly Val Gln Ala Glu
 65                  70                  75                  80

Asp Glu Ala Asp Tyr Tyr Cys Gln Ser Ala Asp Asn Ser Ile Thr Tyr
                 85                  90                  95

Arg Val Phe Gly Gly Gly Thr Lys Val Thr Val Leu
                100                 105

<210> SEQ ID NO 291
<211> LENGTH: 111
<212> TYPE: PRT
<213> ORGANISM: Artificial Sequence
```

<220> FEATURE:
<223> OTHER INFORMATION: Synthetic: PD1-33, VL

<400> SEQUENCE: 291

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Gly Tyr
            20                  25                  30

Asn Tyr Val Ser Trp Tyr Gln His His Pro Gly Lys Ala Pro Lys Leu
        35                  40                  45

Ile Ile Tyr Asp Val Thr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Leu Ala Glu Asp Glu Gly Asp Tyr Tyr Cys Ser Ser Tyr Thr Ile Val
                85                  90                  95

Thr Asn Phe Glu Val Leu Phe Gly Gly Gly Thr Lys Leu Thr Val
            100                 105                 110

<210> SEQ ID NO 292
<211> LENGTH: 110
<212> TYPE: PRT
<213> ORGANISM: Artificial Sequence
<220> FEATURE:
<223> OTHER INFORMATION: Synthetic: PD1-35, VL

<400> SEQUENCE: 292

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Ser Val Asn Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asn Glu Ala Asp Tyr Tyr Cys Ala Ala Trp Asp Asp Ser Leu
                85                  90                  95

Asn Gly Pro Val Phe Gly Arg Gly Thr Lys Val Thr Val Leu
            100                 105                 110

<210> SEQ ID NO 293
<211> LENGTH: 107
<212> TYPE: PRT
<213> ORGANISM: Artificial Sequence
<220> FEATURE:
<223> OTHER INFORMATION: Synthetic: PD1-F2, VL

<400> SEQUENCE: 293

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Trp
                 85                  90                  95

Thr Phe Gly Gln Gly Thr Lys Leu Glu Ile Lys
            100                 105
```

<210> SEQ ID NO 294
<211> LENGTH: 20
<212> TYPE: PRT
<213> ORGANISM: Artificial Sequence
<220> FEATURE:
<223> OTHER INFORMATION: Synthetic: FlagHis Tag

<400> SEQUENCE: 294

```
Gly Ser Gly Asp Tyr Lys Asp Asp Asp Asp Lys Gly Ser Gly His His
 1               5                   10                  15

His His His His
            20
```

<210> SEQ ID NO 295
<211> LENGTH: 252
<212> TYPE: PRT
<213> ORGANISM: Artificial Sequence
<220> FEATURE:
<223> OTHER INFORMATION: Synthetic: IgG1 Fc from scFv-Fc

<400> SEQUENCE: 295

```
Ala Ala Gly Ser Asp Gln Glu Pro Lys Ser Ser Asp Lys Thr His Thr
 1               5                   10                  15

Cys Pro Pro Cys Ser Ala Pro Glu Leu Leu Gly Gly Ser Ser Val Phe
                20                  25                  30

Leu Phe Pro Pro Lys Pro Lys Asp Thr Leu Met Ile Ser Arg Thr Pro
            35                  40                  45

Glu Val Thr Cys Val Val Val Asp Val Ser His Glu Asp Pro Glu Val
 50                  55                  60

Lys Phe Asn Trp Tyr Val Asp Gly Val Glu Val His Asn Ala Lys Thr
 65                  70                  75                  80

Lys Pro Arg Glu Glu Gln Tyr Asn Ser Thr Tyr Arg Val Val Ser Val
                 85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys Gly Ser
225                 230                 235                 240
```

Gly Asp Tyr Lys Asp Asp Asp Lys Gly Ser Gly
                245                 250

<210> SEQ ID NO 296
<211> LENGTH: 330
<212> TYPE: PRT
<213> ORGANISM: Artificial Sequence
<220> FEATURE:
<223> OTHER INFORMATION: Synthetic: HC Constant

<400> SEQUENCE: 296

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 297

```
<211> LENGTH: 107
<212> TYPE: PRT
<213> ORGANISM: Artificial Sequence
<220> FEATURE:
<223> OTHER INFORMATION: Synthetic: LC Constant

<400> SEQUENCE: 297

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 298
<211> LENGTH: 15
<212> TYPE: PRT
<213> ORGANISM: Artificial Sequence
<220> FEATURE:
<223> OTHER INFORMATION: Synthetic: Linker

<400> SEQUENCE: 298

Gly Gly Gly Gly Ser Gly Gly Gly Gly Ser Gly Gly Gly Gly Ser
1               5                   10                  15

<210> SEQ ID NO 299
<211> LENGTH: 288
<212> TYPE: PRT
<213> ORGANISM: Artificial Sequence
<220> FEATURE:
<223> OTHER INFORMATION: Synthetic: murine PD-1

<400> SEQUENCE: 299

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140
```

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Ala Trp Ala Leu Ala Val
            180                 185                 190

Phe Cys Ser Thr Ser Met Ser Glu Ala Arg Gly Ala Gly Ser Lys Asp
            195                 200                 205

Asp Thr Leu Lys Glu Glu Pro Ser Ala Ala Pro Val Pro Ser Val Ala
            210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
            245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
            275                 280                 285

<210> SEQ ID NO 300
<211> LENGTH: 288
<212> TYPE: PRT
<213> ORGANISM: Artificial Sequence
<220> FEATURE:
<223> OTHER INFORMATION: Synthetic: cyno PD-1

<400> SEQUENCE: 300

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
            85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Ala Trp Ala Leu Ala Val
            180                 185                 190

Phe Cys Ser Thr Ser Met Ser Glu Ala Arg Gly Ala Gly Ser Lys Asp
            195                 200                 205

Asp Thr Leu Lys Glu Glu Pro Ser Ala Ala Pro Val Pro Ser Val Ala
            210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
                260                 265                 270

Gly Pro Arg Pro Pro Arg His Glu Asp Gly His Cys Ser Trp Pro Leu
                275                 280                 285

<210> SEQ ID NO 301
<211> LENGTH: 9
<212> TYPE: PRT
<213> ORGANISM: Artificial Sequence
<220> FEATURE:
<223> OTHER INFORMATION: Synthetic: Linker

<400> SEQUENCE: 301

Ala Ala Gly Ser Asp Gln Glu Pro Lys
1               5

<210> SEQ ID NO 302
<211> LENGTH: 471
<212> TYPE: PRT
<213> ORGANISM: Artificial Sequence
<220> FEATURE:
<223> OTHER INFORMATION: Synthetic: h1E9-4 & h1E9-5, HC-FlagHis

<400> SEQUENCE: 302

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Thr
                20                  25                  30

Phe Gly Met Ser Trp Val Arg Gln Ala Pro Gly Lys Gly Leu Glu Trp
                35                  40                  45

Val Ala Thr Ile Ser Gly Gly Ser Asp Thr Tyr Tyr Pro Asp Ser
50                  55                  60

Val Gln Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gln Gly Tyr Asp Val Tyr Ser Trp Phe Ala Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
                210                 215                 220

Asp Lys Thr His Thr Cys Pro Pro Cys Pro Ala Pro Glu Leu Leu Gly
225                 230                 235                 240

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Ser Gly Asp Tyr Lys Asp Asp Asp Lys Gly Ser
    450                 455                 460

Gly His His His His His His
465                 470

<210> SEQ ID NO 303
<211> LENGTH: 219
<212> TYPE: PRT
<213> ORGANISM: Artificial Sequence
<220> FEATURE:
<223> OTHER INFORMATION: Synthetic: h1E9-5, LC

<400> SEQUENCE: 303

Met Glu Ile Val Leu Thr Gln Ser Pro Ala Thr Leu Ser Leu Ser Pro
1               5                   10                  15

Gly Glu Arg Ala Thr Leu Ser Cys Arg Ala Ser Glu Ser Val Asp Asn
                20                  25                  30

Ser Gly Ile Ser Phe Met Ser Trp Tyr Gln Gln Lys Pro Gly Gln Ala
            35                  40                  45

Pro Arg Leu Leu Ile Tyr Thr Ala Ser Asn Gln Gly Ser Gly Ile Pro
        50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Ser
                85                  90                  95

Lys Glu Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125
```

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 304
<211> LENGTH: 219
<212> TYPE: PRT
<213> ORGANISM: Artificial Sequence
<220> FEATURE:
<223> OTHER INFORMATION: Synthetic: h1E9-4, LC

<400> SEQUENCE: 304

Met Asp Ile Gln Leu Thr Gln Ser Pro Ser Phe Leu Ser Ala Ser Val
1               5                   10                  15

Gly Asp Arg Val Thr Ile Thr Cys Arg Ala Ser Glu Ser Val Asp Asn
            20                  25                  30

Ser Gly Ile Ser Phe Met Ser Trp Tyr Gln Gln Lys Pro Gly Lys Ala
        35                  40                  45

Pro Lys Leu Leu Ile Tyr Thr Ala Ser Asn Gln Gly Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Gln Gln Ser
                85                  90                  95

Lys Glu Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 305
<211> LENGTH: 507
<212> TYPE: PRT
<213> ORGANISM: Artificial Sequence
<220> FEATURE:
<223> OTHER INFORMATION: Synthetic: PD1-F2v-scFvFcFlagHis, scFv-Fc

<400> SEQUENCE: 305

```
Met Gly Ala His Ser Glu Val Gln Leu Val Gln Ser Gly Gly Val
1               5                   10                  15

Val Gln Pro Gly Arg Ser Leu Arg Leu Ser Cys Ala Ala Ser Gly Phe
            20                  25                  30

Thr Phe Ser Ser Tyr Trp Met Ser Trp Val Arg Gln Ala Pro Gly Lys
        35                  40                  45

Gly Leu Glu Trp Val Ser Ala Ile Ser Gly Ser Gly Gly Ser Thr Tyr
    50                  55                  60

Tyr Ala Asp Ser Val Lys Gly Arg Phe Thr Ile Ser Arg Asp Asn Ser
65                  70                  75                  80

Lys Asn Thr Leu Tyr Leu Gln Met Asn Ser Leu Arg Ala Glu Asp Thr
                85                  90                  95

Ala Val Tyr Tyr Cys Ala Lys Glu Asn Trp Gly Ser Tyr Phe Asp Leu
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Ser Gly Val His Ser Asp Ile
    130                 135                 140

Val Met Thr Gln Ser Pro Ser Thr Leu Ser Ala Ser Val Gly Asp Arg
145                 150                 155                 160

Val Thr Ile Thr Cys Arg Ala Ser Gln Gly Ile Ser Ser Trp Leu Ala
                165                 170                 175

Trp Tyr Gln Gln Lys Pro Gly Arg Ala Pro Lys Val Leu Ile Tyr Lys
            180                 185                 190

Ala Ser Thr Leu Glu Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Tyr Ser Thr Pro Trp Thr Phe
225                 230                 235                 240

Gly Gln Gly Thr Lys Leu Glu Ile Lys Ala Ala Gly Ser Asp Gln Glu
                245                 250                 255

Pro Lys Ser Ser Asp Lys Thr His Thr Cys Pro Pro Cys Ser Ala Pro
            260                 265                 270

Glu Leu Leu Gly Gly Ser Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415
```

```
Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
450                 455                 460

Cys Ser Val Met His Glu Ala Leu His Asn His Tyr Thr Gln Lys Ser
465                 470                 475                 480

Leu Ser Leu Ser Pro Gly Lys Gly Ser Gly Asp Tyr Lys Asp Asp Asp
            485                 490                 495

Asp Lys Gly Ser Gly His His His His His
            500                 505

<210> SEQ ID NO 306
<211> LENGTH: 118
<212> TYPE: PRT
<213> ORGANISM: Artificial Sequence
<220> FEATURE:
<223> OTHER INFORMATION: Synthetic: PD1-F2v, VH

<400> SEQUENCE: 306

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Trp Gly Ser Tyr Phe Asp Leu Trp Gly Gln Gly Thr
            100                 105                 110

Thr Val Thr Val Ser Ser
        115

<210> SEQ ID NO 307
<211> LENGTH: 452
<212> TYPE: PRT
<213> ORGANISM: Artificial Sequence
<220> FEATURE:
<223> OTHER INFORMATION: Synthetic: PD1-F2v, HC

<400> SEQUENCE: 307

Gly Ala His Ser Glu Val Gln Leu Val Gln Ser Gly Gly Gly Val Val
1               5                   10                  15

Gln Pro Gly Arg Ser Leu Arg Leu Ser Cys Ala Ala Ser Gly Phe Thr
            20                  25                  30

Phe Ser Ser Tyr Trp Met Ser Trp Val Arg Gln Ala Pro Gly Lys Gly
        35                  40                  45

Leu Glu Trp Val Ser Ala Ile Ser Gly Ser Gly Gly Ser Thr Tyr Tyr
    50                  55                  60

Ala Asp Ser Val Lys Gly Arg Phe Thr Ile Ser Arg Asp Asn Ser Lys
65                  70                  75                  80

Asn Thr Leu Tyr Leu Gln Met Asn Ser Leu Arg Ala Glu Asp Thr Ala
```

85                  90                  95
Val Tyr Tyr Cys Ala Lys Glu Asn Trp Gly Ser Tyr Phe Asp Leu Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 308
<211> LENGTH: 220
<212> TYPE: PRT
<213> ORGANISM: Artificial Sequence
<220> FEATURE:
<223> OTHER INFORMATION: Synthetic: PD1-F2v, LC

<400> SEQUENCE: 308

Gly Val His Ser Asp Ile Val Met Thr Gln Ser Pro Ser Thr Leu Ser
1               5                   10                  15

Ala Ser Val Gly Asp Arg Val Thr Ile Thr Cys Arg Ala Ser Gln Gly
            20                  25                  30

Ile Ser Ser Trp Leu Ala Trp Tyr Gln Gln Lys Pro Gly Arg Ala Pro
        35                  40                  45

Lys Val Leu Ile Tyr Lys Ala Ser Thr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Ser Thr Pro Trp Thr Phe Gly Gln Gly Thr Lys Leu Glu Ile Lys Arg
            100                 105                 110

His Met Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 309
<211> LENGTH: 10
<212> TYPE: PRT
<213> ORGANISM: Artificial Sequence
<220> FEATURE:
<223> OTHER INFORMATION: Synthetic: 1353-E07-R5, CDR-H3

<400> SEQUENCE: 309

Asp Ala Glu Tyr Arg Leu Gly Ser Gly Tyr
1               5                   10

<210> SEQ ID NO 310
<211> LENGTH: 10
<212> TYPE: PRT
<213> ORGANISM: Artificial Sequence
<220> FEATURE:
<223> OTHER INFORMATION: Synthetic: 1353-A09-R5, CDR-H3

<400> SEQUENCE: 310

Asp Ser Glu Tyr Arg Ser Gly Ser Gly Tyr
1               5                   10

<210> SEQ ID NO 311
<211> LENGTH: 10
<212> TYPE: PRT
<213> ORGANISM: Artificial Sequence
<220> FEATURE:
<223> OTHER INFORMATION: Synthetic: 1353-F09-R5, CDR-H3

<400> SEQUENCE: 311

Asp Ala Glu Tyr Arg Ser Gly Ser Gly Tyr
1               5                   10

<210> SEQ ID NO 312
<211> LENGTH: 10
<212> TYPE: PRT
<213> ORGANISM: Artificial Sequence
<220> FEATURE:
<223> OTHER INFORMATION: Synthetic: 1353-G08-R5, CDR-H3

<400> SEQUENCE: 312

Asp Ala Asp Tyr Arg Ser Gly Ser Gly Tyr
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Synthetic: 1353-G10-R5, CDR-H3

<400> SEQUENCE: 313

Asp Val Asp Tyr Arg Thr Gly Ser Gly Tyr
1               5                   10

<210> SEQ ID NO 314
<211> LENGTH: 10
<212> TYPE: PRT
<213> ORGANISM: Artificial Sequence
<220> FEATURE:
<223> OTHER INFORMATION: Synthetic: 1353-C07-R5, CDR-H3

<400> SEQUENCE: 314

Asp Val Asp Tyr Arg Ser Gly Ser Gly Tyr
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Synthetic: 1353-H08-R5, CDR-H3

<400> SEQUENCE: 315

Asp Val Asp Tyr Arg Ser Gly Ser Gly Tyr
1               5                   10

<210> SEQ ID NO 316
<211> LENGTH: 119
<212> TYPE: PRT
<213> ORGANISM: Artificial Sequence
<220> FEATURE:
<223> OTHER INFORMATION: Synthetic: 1353-E07-R5, VH

<400> SEQUENCE: 316

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Glu Thr Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr 65                  70                  75                  80
Met Glu Leu Arg Ser Leu Arg Ser Asp Asp Thr Ala Val Tyr Tyr Cys
                    85                  90                  95

Ala Arg Asp Ala Glu Tyr Arg Leu Gly Ser Gly Tyr Trp Gly Gln Gly
            100                 105                 110

Thr Leu Val Thr Val Ser Ser
        115

<210> SEQ ID NO 317
<211> LENGTH: 119
<212> TYPE: PRT
<213> ORGANISM: Artificial Sequence
<220> FEATURE:
<223> OTHER INFORMATION: Synthetic: 1353-A09-R5, VH

<400> SEQUENCE: 317

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Trp Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Glu Tyr Arg Ser Gly Ser Gly Tyr Trp Gly Gln Gly
            100                 105                 110

Thr Leu Val Thr Val Ser Ser
        115

<210> SEQ ID NO 318
<211> LENGTH: 119
<212> TYPE: PRT
<213> ORGANISM: Artificial Sequence
<220> FEATURE:
<223> OTHER INFORMATION: Synthetic: 1353-F09-R5, VH

<400> SEQUENCE: 318

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Arg Gln Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Glu Tyr Arg Ser Gly Ser Gly Tyr Trp Gly Gln Gly
            100                 105                 110

Thr Leu Val Thr Val Ser Ser
        115

<210> SEQ ID NO 319
<211> LENGTH: 119
<212> TYPE: PRT
<213> ORGANISM: Artificial Sequence
<220> FEATURE:
<223> OTHER INFORMATION: Synthetic: 1353-G08-R5, VH

<400> SEQUENCE: 319

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Arg Tyr
            20                  25                  30

Gly Ile Ser Trp Val Arg Gln Ala Pro Gly Gln Gly Leu Glu Trp Met
        35                  40                  45

Gly Trp Val Ser Ala His Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Asp Tyr Arg Ser Gly Ser Gly Tyr Trp Gly Gln Gly
            100                 105                 110

Thr Leu Val Thr Val Ser Ser
        115
```

<210> SEQ ID NO 320
<211> LENGTH: 119
<212> TYPE: PRT
<213> ORGANISM: Artificial Sequence
<220> FEATURE:
<223> OTHER INFORMATION: Synthetic: 1353-G10-R5, VH

<400> SEQUENCE: 320

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Pro His Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Asp Tyr Arg Thr Gly Ser Gly Tyr Trp Gly Gln Gly
            100                 105                 110

Thr Leu Val Thr Val Ser Ser
        115
```

<210> SEQ ID NO 321
<211> LENGTH: 119
<212> TYPE: PRT
<213> ORGANISM: Artificial Sequence
<220> FEATURE:
<223> OTHER INFORMATION: Synthetic: 1353-C07-R5, VH

<400> SEQUENCE: 321

```
Glu Val Gln Leu Val Gln Ser Gly Ala Glu Val Lys Lys Pro Gly Ala
```

-continued

Ser Val Lys Val Ser Cys Lys Ala Ser Gly Tyr Arg Phe Ser Thr Phe
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Val Asp Tyr Arg Ser Gly Ser Gly Tyr Trp Gly Gln Gly
                100                 105                 110

Thr Leu Val Thr Val Ser Ser
            115

<210> SEQ ID NO 322
<211> LENGTH: 119
<212> TYPE: PRT
<213> ORGANISM: Artificial Sequence
<220> FEATURE:
<223> OTHER INFORMATION: Synthetic: 1353-H08-R5, VH

<400> SEQUENCE: 322

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Arg Phe Thr Arg Gln
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Lys Tyr Ala Gln Lys Leu
     50                  55                  60

Gln Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Val Asp Tyr Arg Ser Gly Ser Gly Tyr Trp Gly Gln Gly
                100                 105                 110

Thr Leu Val Thr Val Ser Ser
            115

<210> SEQ ID NO 323
<211> LENGTH: 119
<212> TYPE: PRT
<213> ORGANISM: Artificial Sequence
<220> FEATURE:
<223> OTHER INFORMATION: Synthetic: 1353-H09-R5, VH

<400> SEQUENCE: 323

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Arg Phe Pro His Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
     50                  55                  60

```
Gln Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Ala Glu Tyr Arg Ser Gly Ser Gly Tyr Trp Gly Gln Gly
            100                 105                 110

Thr Leu Val Thr Val Ser Ser
            115
```

<210> SEQ ID NO 324
<211> LENGTH: 471
<212> TYPE: PRT
<213> ORGANISM: Artificial Sequence
<220> FEATURE:
<223> OTHER INFORMATION: Synthetic: H1E9-HC3, HC-FlagHis

<400> SEQUENCE: 324

```
Met Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser Thr
                 20                  25                  30

Phe Gly Met Ser Trp Val Arg Gln Ala Pro Gly Lys Gly Leu Glu Trp
             35                  40                  45

Val Ala Thr Ile Ser Gly Gly Gly Ser Asp Thr Tyr Tyr Pro Asp Ser
 50                  55                  60

Val Lys Gly Arg Phe Thr Ile Ser Arg Asp Asn Ala Lys Asn Ser Leu
 65                  70                  75                  80

Tyr Leu Gln Met Asn Ser Leu Arg Ala Glu Asp Thr Ala Val Tyr Tyr
                 85                  90                  95

Cys Ala Arg Gln Gly Tyr Asp Val Tyr Ser Trp Phe Ala Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Gly Ser Gly Asp Tyr Lys Asp Asp Asp Lys Gly Ser
450                 455                 460

Gly His His His His His His
465                 470

<210> SEQ ID NO 325
<211> LENGTH: 471
<212> TYPE: PRT
<213> ORGANISM: Artificial Sequence
<220> FEATURE:
<223> OTHER INFORMATION: Synthetic: H1E9-HC2, HC-FlagHis

<400> SEQUENCE: 325

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser Thr
            20                  25                  30

Phe Gly Met Ser Trp Val Arg Gln Ala Pro Gly Lys Gly Leu Glu Trp
        35                  40                  45

Val Ala Thr Ile Ser Gly Gly Gly Ser Asp Thr Tyr Tyr Pro Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gln Gly Tyr Asp Val Tyr Ser Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

```
Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Ser Gly Asp Tyr Lys Asp Asp Asp Asp Lys Gly Ser
450                 455                 460

Gly His His His His His His
465                 470

<210> SEQ ID NO 326
<211> LENGTH: 471
<212> TYPE: PRT
<213> ORGANISM: Artificial Sequence
<220> FEATURE:
<223> OTHER INFORMATION: Synthetic: H1E9-HC1, HC-FlagHis

<400> SEQUENCE: 326

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Thr
            20                  25                  30

Phe Gly Met Ser Trp Val Arg Gln Ala Pro Gly Lys Gly Leu Glu Trp
        35                  40                  45

Val Ala Thr Ile Ser Gly Gly Ser Asp Thr Tyr Tyr Pro Asp Ser
    50                  55                  60

Val Lys Gly Arg Phe Thr Ile Ser Arg Asp Asn Ser Lys Asn Thr Leu
65                  70                  75                  80
```

Tyr Leu Gln Met Asn Ser Leu Arg Ala Glu Asp Thr Ala Val Tyr Tyr
                85                  90                  95

Cys Ala Arg Gln Gly Tyr Asp Val Tyr Ser Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Ser Gly Asp Tyr Lys Asp Asp Asp Lys Gly Ser
450                 455                 460

Gly His His His His His His
465                 470

<210> SEQ ID NO 327
<211> LENGTH: 219
<212> TYPE: PRT

<213> ORGANISM: Artificial Sequence
<220> FEATURE:
<223> OTHER INFORMATION: Synthetic: H1E9-LC4, LC

<400> SEQUENCE: 327

```
Met Asp Ile Val Leu Thr Gln Ser Pro Asp Ser Leu Ala Val Ser Leu
1               5                   10                  15

Gly Glu Arg Ala Thr Ile Asn Cys Arg Ala Ser Glu Ser Val Asp Asn
            20                  25                  30

Ser Gly Ile Ser Phe Met Ser Trp Tyr Gln Gln Lys Pro Gly Gln Pro
        35                  40                  45

Pro Lys Leu Leu Ile Tyr Thr Ala Ser Asn Gln Gly Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Ser
                85                  90                  95

Lys Glu Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 328
<211> LENGTH: 219
<212> TYPE: PRT
<213> ORGANISM: Artificial Sequence
<220> FEATURE:
<223> OTHER INFORMATION: Synthetic: H1E9-LC3, LC

<400> SEQUENCE: 328

```
Met Glu Ile Val Leu Thr Gln Ser Pro Gly Thr Leu Ser Leu Ser Pro
1               5                   10                  15

Gly Glu Arg Ala Thr Leu Ser Cys Arg Ala Ser Glu Ser Val Asp Asn
            20                  25                  30

Ser Gly Ile Ser Phe Met Ser Trp Tyr Gln Gln Lys Pro Gly Gln Ala
        35                  40                  45

Pro Arg Leu Leu Ile Tyr Thr Ala Ser Asn Gln Gly Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Gln Gln Ser
                85                  90                  95

Lys Glu Val Pro Trp Thr Phe Gly Gln Gly Thr Lys Val Glu Ile Lys
            100                 105                 110
```

```
Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 329
<211> LENGTH: 219
<212> TYPE: PRT
<213> ORGANISM: Artificial Sequence
<220> FEATURE:
<223> OTHER INFORMATION: Synthetic: H1E9-LC2, LC

<400> SEQUENCE: 329

```
Met Asp Ile Val Leu Thr Gln Ser Pro Leu Ser Leu Pro Val Thr Pro
1               5                   10                  15

Gly Glu Pro Ala Ser Ile Ser Cys Arg Ala Ser Glu Ser Val Asp Asn
            20                  25                  30

Ser Gly Ile Ser Phe Met Ser Trp Tyr Leu Gln Lys Pro Gly Gln Ser
        35                  40                  45

Pro Gln Leu Leu Ile Tyr Thr Ala Ser Asn Gln Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Ser
                85                  90                  95

Lys Glu Val Pro Trp Thr Phe Gly Gln Gly Thr Lys Val Glu Ile Lys
            100                 105                 110

Arg Thr Val Ala Ala Pro Ser Val Phe Ile Phe Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 330
<211> LENGTH: 219
<212> TYPE: PRT
<213> ORGANISM: Artificial Sequence
<220> FEATURE:

```
<223> OTHER INFORMATION: Synthetic: H1E9-LC1, LC

<400> SEQUENCE: 330

Met Asp Ile Gln Leu Thr Gln Ser Pro Ser Ser Leu Ser Ala Ser Val
1               5                   10                  15

Gly Asp Arg Val Thr Ile Thr Cys Arg Ala Ser Glu Ser Val Asp Asn
            20                  25                  30

Ser Gly Ile Ser Phe Met Ser Trp Tyr Gln Gln Lys Pro Gly Lys Ala
        35                  40                  45

Pro Lys Leu Leu Ile Tyr Thr Ala Ser Asn Gln Gly Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Gln Gln Ser
                85                  90                  95

Lys Glu Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 331
<211> LENGTH: 17
<212> TYPE: PRT
<213> ORGANISM: Artificial Sequence
<220> FEATURE:
<223> OTHER INFORMATION: Synthetic: CDR-H2

<400> SEQUENCE: 331

Thr Ile Ser Gly Gly Gly Ser Asp Thr Tyr Tyr Pro Asp Ser Val Gln
1               5                   10                  15

Gly
```

ANTI-PD-1 ANTIBODIES, COMPOSITIONS COMPRISING ANTI-PD-1 ANTIBODIES AND METHODS OF USING ANTI-PD-1 ANTIBODIES

FIELD

Provided herein are antibodies with binding specificity for PD-1 and compositions comprising the antibodies, including pharmaceutical compositions, diagnostic compositions and kits. Also provided are methods of using anti-PD-1 antibodies for therapeutic and diagnostic purposes.

BACKGROUND

Programmed cell death protein 1 (PD-1, also known as CD279) is a cell surface protein molecule that belongs to the immunoglobulin superfamily. It is expressed on T and B lymphocytes and macrophages, and plays a role in cell fate and differentiation. See Ishida et al., *EMBO J.*, 1992, 11:3887-3895, incorporated by reference in its entirety. Activation of PD-1 is thought to negatively regulate the immune response. See Blank et al., *Cancer Immunol. Immunother.*, 2007, 56:739-745; and Freeman et al., *J. Exp. Med.*, 2000, 192:1027-1034, each of which is incorporated by reference in its entirety.

PD-1 has two known ligands, PD-L1 and PD-L2, which are both members of the B7 family. See Freeman et al., supra; and Latchman et al., *Nat. Immunol.*, 2001, 2:261-268, each of which is incorporated by reference in its entirety. The interaction between PD-1 and these ligands is thought to play a role in a variety of diseases, including cancer (see Ribas and Tumeh, *Clin. Cancer Res.*, 2014, Jun. 26, PMID: 24970841 [Epub ahead of print]), autoimmune disease (see Dai et al., *Cell Immunol.*, 2014, 290:72-79), and infection (see Day et al., *Nature*, 2006, 443:350-354). Each of the references cited in the preceding sentence is incorporated by reference in its entirety. In particular, the engagement of PD-1 by one of its ligands is thought to inhibit T-cell effector functions in an antigen-specific manner.

In view of the role of PD-1 in multiple disease processes, there is a need for improved methods of modulating the interaction of PD-1 with its ligands and the downstream signaling processes activated by PD-1. Moreover, given the role of PD-1 in several diseases, there is also a need for therapeutics that specifically target cells and tissues that express PD-1.

SUMMARY

Provided herein are antibodies that selectively bind PD-1. In some embodiments, the antibodies bind human PD-1. In some embodiments, the antibodies also bind homologs of human PD-1. In some aspects, the homolog is a cynomolgus monkey homolog. In some aspects, the homolog is a murine homolog. In some embodiments, the antibodies bind to human PD-1, a cynomolgus monkey homolog, and a murine homolog.

In some embodiments, the antibodies comprise at least one CDR sequence defined by a consensus sequence provided in this disclosure. In some embodiments, the antibodies comprise an illustrative CDR, $V_H$, or $V_L$ sequence provided in this disclosure, or a variant thereof. In some aspects, the variant is a variant with one or more conservative amino acid substitutions.

Also provided are compositions and kits comprising the antibodies. In some embodiments, the compositions are pharmaceutical compositions. Any suitable pharmaceutical composition may be used. In some embodiments, the pharmaceutical composition is a composition for parenteral administration.

This disclosure also provides methods of using the anti-PD-1 antibodies provided herein. In some embodiments, the method is a method of treatment. In some embodiments, the method is a diagnostic method. In some embodiments, the method is an analytical method. In some embodiments, the method is a method of purifying and/or quantifying PD-1.

In some embodiments, the antibodies are used to treat a disease or condition. In some aspects, the disease or condition is selected from a cancer, autoimmune disease, and infection.

BRIEF DESCRIPTION OF THE DRAWINGS

FIG. 3 provides a chart of interferon gamma (IFN-g) secretion in a cytomegalovirus (CMV) recall assay, as described in Example 16.

FIG. 4 provides a chart of interferon gamma (IFN-g) secretion in a mixed lymphocyte response (MLR) assay, as described in Example 17.

FIG. 5 provides a chart of mouse survival in a model of graft versus host disease, as described in Example 18.

DETAILED DESCRIPTION

1. Definitions

Figure 1:
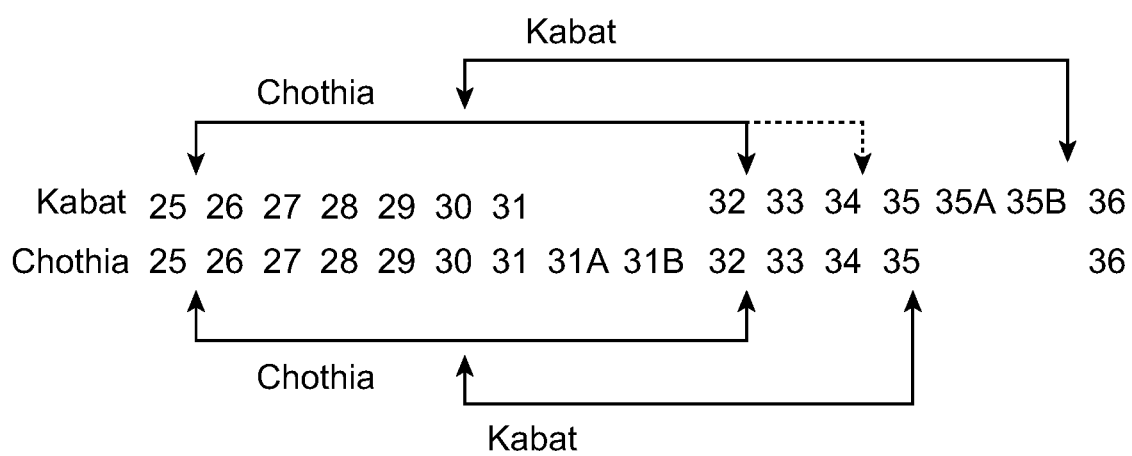
FIG. 1 provides a comparison of the Kabat and Chothia numbering systems for CDR-H1. Adapted from Martin A.C.R. (2010). Protein Sequence and Structure Analysis of Antibody Variable Domains. In R. Kontermann & S. Dübel (Eds.), *Antibody Engineering vol. 2* (pp. 33-51). Springer-Verlag, Berlin Heidelberg.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value ±one standard deviation of that value.

The term "combinations thereof" includes every possible combination of elements to which the term refers to. For example, a sentence stating that "if $\alpha_2$ is A, then $\alpha_3$ is not D; $\alpha_5$ is not S; or $\alpha_6$ is not S; or combinations thereof" includes the following combinations when $\alpha_2$ is A: (1) $\alpha_3$ is not D; (2) $\alpha_5$ is not S; (3) $\alpha_6$ is not S; (4) $\alpha_3$ is not D; $\alpha_5$ is not S; and $\alpha_6$ is not S; (5) $\alpha_3$ is not D and $\alpha_5$ is not S; (6) $\alpha_3$ is not D and $\alpha_6$ is not S; and (7) $\alpha_5$ is not S and $\alpha_6$ is not S.

The terms "PD-1" and "PD-1 antigen" are used interchangeably herein. Unless specified otherwise, the terms include any variants, isoforms and species homologs of human PD-1 that are naturally expressed by cells, or that are expressed by cells transfected with a PD-1 gene. PD-1 proteins include full-length PD-1 (e.g., human PD-1; GI: 167857792; SEQ ID NO: 1; extracellular domain: Pro21-Gln167), as well as alternative splice variants of PD-1, such as PD-1Δex2, PD-1Δex3, PD-1Δex2,3, and PD-1Δex2,3,4. See Nielsen et al., *Cellular Immunology*, 2005, 235:109-116, incorporated by reference in its entirety. In some embodiments, PD-1 proteins include murine PD-1 (e.g., SEQ ID NO: 299; extracellular domain: Leu25-Gln167). In some embodiments, PD-1 proteins include cynomolgus PD-1 (e.g., SEQ ID NO: 300; extracellular domain: Pro21-Gln167).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer. A "PD-1 antibody," "anti-PD-1 antibody," "PD-1 Ab," "PD-1-specific antibody" or "anti-PD-1 Ab" is an antibody, as described herein, which binds specifically to the antigen PD-1. In some embodiments, the antibody binds the extracellular domain of PD-1.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and confer antigen specificity and binding affinity to the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes. FIG. 1 provides a comparison of the Kabat and Chothia numbering schemes for CDR-H1. See Martin (2010), supra.

Unless otherwise specified, the numbering scheme used for identification of a particular CDR herein is the Kabat/Chothia numbering scheme. Where the residues encompassed by these two numbering schemes diverge, the numbering scheme is specified as either Kabat or Chothia.

TABLE 1

Residues in CDRs according to Kabat and Chothia numbering schemes.

| CDR | Kabat | Chothia |
| --- | --- | --- |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by papain digestion of a full-length antibody.

"F(ab')$_2$" fragments contain two Fab' fragments joined, near the hinge region, by disulfide bonds. F(ab')$_2$ fragments may be generated, for example, by pepsin digestion of an intact antibody. The F(ab') fragments can be dissociated, for example, by treatment with ß-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Antibodies from *Escherichia coli*. In Rosenberg M. & Moore G. P. (Eds.), *The Pharmacology of Monoclonal Antibodies* vol. 113 (pp. 269-315). Springer-Verlag, N.Y., incorporated by reference in its entirety. "scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain is an IgG1 Fc domain (e.g., SEQ ID NO: 295). In some embodiments, the linker is $(G_4S)_3$ (see SEQ ID NO: 298).

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is provided as a solution comprising at least 85%, 90%, 95%, 98%, 99% to 100% by weight of an antibody, the remainder of the weight comprising the weight of other solutes dissolved in the solvent.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Affinity can be determined, for example, using surface plasmon resonance (SPR) technology, such as a Biacore® instrument.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that is similar to the target, such as an excess of non-labeled target. In that case, specific binding is indicated if the binding of the labeled target to a probe is competitively inhibited by the excess non-labeled target.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "$K_A$" ($M^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896, each of which is incorporated by reference in its entirety.

When used herein in the context of two or more antibodies, the term "competes with" or "cross-competes with" indicates that the two or more antibodies compete for binding to an antigen (e.g., PD-1). In one exemplary assay, PD-1 is coated on a plate and allowed to bind a first antibody, after which a second, labeled antibody is added. If the presence of the first antibody reduces binding of the second antibody, then the antibodies compete. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to PD-1 variants with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, or CLUSTAL OMEGA software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of one or more amino acids with one or more chemically or functionally similar amino acids. Conservative substitution tables providing similar amino acids are well known in the art. Polypeptide sequences having such substitutions are known as "conservatively modified variants." Such conservatively modified variants are in addition to and do not exclude polymorphic variants, interspecies homologs, and alleles. By way of example, the following groups of amino acids are considered conservative substitutions for one another.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, N, Q, R, S, P, and T |
| Flexible Residues | Q, T, K, S, G, P, D, E, and R |
| Group 1 | A, S, and T |
| Group 2 | D and E |
| Group 3 | N and Q |
| Group 4 | R and K |
| Group 5 | I, L, and M |
| Group 6 | F, Y, and W |
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder.

As used herein, the term "subject" means a mammalian subject. Exemplary subjects include, but are not limited to humans, monkeys, dogs, cats, mice, rats, cows, horses, camels, avians, goats and sheep. In certain embodiments, the subject is a human. In some embodiments, the subject has cancer, an autoimmune disease or condition, and/or an infection that can be treated with an antibody provided herein. In some embodiments, the subject is a human that is suspected to have cancer, an autoimmune disease or condition, and/or an infection.

2. Antibodies

Provided herein are antibodies that selectively bind human PD-1. In some aspects, the antibody selectively binds to the extracellular domain of human PD-1. In some aspects, the antibody selectively binds to one or more of full-length human PD-1, PD-1Δex2, PD-1Δex3, PD-1Δex2,3, and PD-1Δex2,3,4. See Nielsen et al., *Cellular Immunology*, 2005, 235:109-116, incorporated by reference in its entirety.

In some embodiments, the antibody binds to homologs of human PD-1. In some aspects, the antibody binds to a homolog of human PD-1 from a species selected from monkeys, mice, dogs, cats, rats, cows, horses, goats and sheep. In some aspects, the homolog is a cynomolgus monkey homolog. In some aspects, the homolog is a murine homolog.

In some embodiments, the antibody has one or more CDRs having particular lengths, in terms of the number of amino acid residues. In some embodiments, the Chothia CDR-H1 of the antibody is 6, 7, 8, or 9 residues in length. In some embodiments, the Kabat CDR-H1 of the antibody is 4, 5, 6, or 7 residues in length. In some embodiments, the Chothia CDR-H2 of the antibody is 5, 6, or 7 residues in length. In some embodiments, the Kabat CDR-H2 of the antibody is 15, 16, 17, or 18 residues in length. In some embodiments, the Kabat/Chothia CDR-H3 of the antibody is 5, 6, 7, 8, 9, 10, 11, or 12 residues in length.

In some aspects, the Kabat/Chothia CDR-L1 of the antibody is 9, 10, 11, 12, 13, 14, 15, or 16 residues in length. In some aspects, the Kabat/Chothia CDR-L2 of the antibody is 6, 7, or 8 residues in length. In some aspects, the Kabat/Chothia CDR-L3 of the antibody is 8, 9, 10, 11, or 12 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

In some embodiments, the antibody inhibits the binding of PD-1 to its ligands. In some aspects, the antibody inhibits the binding of PD-1 to PD-L1. In some aspects, the antibody inhibits the binding of PD-1 to PD-L2. In some aspects, the antibody inhibits the binding of PD-1 to PD-L1 and PD-L2.

The antibodies provided herein may be useful for the treatment of a variety of diseases and conditions, including cancers, autoimmune diseases, and infections.

2.1. CDR-H3 Sequences

In some embodiments, the antibody comprises a CDR-H3 sequence comprising, consisting of, or consisting essentially of a sequence selected from SEQ ID NOs: 113-131 and 309-315. In some aspects, the antibody comprises a CDR-H3 sequence comprising, consisting of, or consisting essentially of SEQ ID NO: 113. In some aspects, the antibody comprises a CDR-H3 sequence comprising, consisting of, or consisting essentially of SEQ ID NO: 114. In some aspects, the antibody comprises a CDR-H3 sequence comprising, consisting of, or consisting essentially of SEQ ID NO: 115. In some aspects, the antibody comprises a CDR-H3 sequence comprising, consisting of, or consisting essentially of SEQ ID NO: 116. In some aspects, the antibody comprises a CDR-H3 sequence comprising, consisting of, or consisting essentially of SEQ ID NO: 117. In some aspects, the antibody comprises a CDR-H3 sequence comprising, consisting of, or consisting essentially of SEQ ID NO: 118. In some aspects, the antibody comprises a CDR-H3 sequence comprising, consisting of, or consisting essentially of SEQ ID NO: 119. In some aspects, the antibody comprises a CDR-H3 sequence comprising, consisting of, or consisting essentially of SEQ ID NO: 120. In some aspects, the antibody comprises a CDR-H3 sequence comprising, consisting of, or consisting essentially of SEQ ID NO: 121. In some aspects, the antibody comprises a CDR-H3 sequence comprising, consisting of, or consisting essentially of SEQ ID NO: 122. In some aspects, the antibody comprises a CDR-H3 sequence comprising, consisting of, or consisting essentially of SEQ ID NO: 123. In some aspects, the antibody comprises a CDR-H3 sequence comprising, consisting of, or consisting essentially of SEQ ID NO: 124. In some aspects, the antibody comprises a CDR-H3 sequence comprising, consisting of, or consisting essentially of SEQ ID NO: 125. In some aspects, the antibody comprises a CDR-H3 sequence comprising, consisting of, or consisting essentially of SEQ ID NO: 126. In some aspects, the antibody comprises a CDR-H3 sequence comprising, consisting of, or consisting essentially of SEQ ID NO: 127. In some aspects, the antibody comprises a CDR-H3 sequence comprising, consisting of, or consisting essentially of SEQ ID NO: 128. In some aspects, the antibody comprises a CDR-H3 sequence comprising, consisting of, or consisting essentially of SEQ ID NO: 129. In some aspects, the antibody comprises a CDR-H3 sequence comprising, consisting of, or consisting essentially of SEQ ID NO: 130. In some aspects, the antibody comprises a CDR-H3 sequence comprising, consisting of, or consisting essentially of SEQ ID NO: 131. In some aspects, the antibody comprises a CDR-H3 sequence comprising, consisting of, or consisting essentially of SEQ ID NO: 309. In some aspects, the antibody comprises a CDR-H3 sequence comprising, consisting of, or consisting essentially of SEQ ID NO: 310. In some aspects, the antibody comprises a CDR-H3 sequence comprising, consisting of, or consisting essentially of SEQ ID NO: 311. In some aspects, the antibody comprises a CDR-H3 sequence comprising, consisting of, or consisting essentially of SEQ ID NO: 312. In some aspects, the antibody comprises a CDR-H3 sequence comprising, consisting of, or consisting essentially of SEQ ID NO: 313. In some aspects, the antibody comprises a CDR-H3 sequence comprising, consisting of, or consisting essentially of SEQ ID NO: 314. In some aspects, the antibody comprises a CDR-H3 sequence comprising, consisting of, or consisting essentially of SEQ ID NO: 315.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-H3 sequence does not comprise, consist of, or consist essentially of a sequence selected from SEQ ID NOs: 132-136. In some aspects, the CDR-H3 sequence does not comprise, consist of, or consist essentially of SEQ ID NO: 132. In some aspects, the CDR-H3 sequence does not comprise, consist of, or consist essentially of SEQ ID NO: 133. In some aspects, the CDR-H3 sequence does not comprise, consist of, or consist essentially of SEQ ID NO: 134. In some aspects, the CDR-H3 sequence does not comprise, consist of, or consist essentially of SEQ ID NO: 135. In some aspects, the CDR-H3 sequence does not comprise, consist of, or consist essentially of SEQ ID NO: 136.

2.2. $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof.

2.2.1. $V_H$ Sequences Comprising Illustrative Kabat CDRs

In some embodiments, the antibody comprises a $V_H$ sequence comprising one or more Kabat CDR-H sequences comprising, consisting of, or consisting essentially of one or more illustrative Kabat CDR-H sequences provided in this disclosure, and variants thereof.

2.2.1.1. Kabat CDR-H3

In some embodiments, the antibody comprises a $V_H$ sequence comprising a Kabat CDR-H3 sequence comprising, consisting of, or consisting essentially of a sequence selected from SEQ ID NOs: 113-131 and 309-315. In some aspects, the antibody comprises a $V_H$ sequence comprising a Kabat CDR-H3 sequence comprising, consisting of, or consisting essentially of SEQ ID NO: 113. In some aspects, the antibody comprises a $V_H$ sequence comprising a Kabat CDR-H3 sequence comprising, consisting of, or consisting essentially of SEQ ID NO: 114. In some aspects, the antibody comprises a $V_H$ sequence comprising a Kabat CDR-H3 sequence comprising, consisting of, or consisting essentially of SEQ ID NO: 115. In some aspects, the antibody comprises a $V_H$ sequence comprising a Kabat CDR-H3 sequence comprising, consisting of, or consisting essentially of SEQ ID NO: 116. In some aspects, the antibody comprises a $V_H$ sequence comprising a Kabat CDR-H3 sequence comprising, consisting of, or consisting essentially of SEQ ID NO: 117. In some aspects, the antibody comprises a $V_H$ sequence comprising a Kabat CDR-H3 sequence comprising, consisting of, or consisting essentially of SEQ ID NO: 118. In some aspects, the antibody comprises a $V_H$ sequence comprising a Kabat CDR-H3 sequence comprising, consisting of, or consisting essentially of SEQ ID NO: 119. In some aspects, the antibody comprises a $V_H$ sequence comprising a Kabat CDR-H3 sequence comprising, consisting of, or consisting essentially of SEQ ID NO: 120. In some aspects, the antibody comprises a $V_H$ sequence comprising a Kabat CDR-H3 sequence comprising, consisting of, or consisting essentially of SEQ ID NO: 121. In some aspects, the antibody comprises a $V_H$ sequence comprising a Kabat CDR-H3 sequence comprising, consisting of, or consisting essentially of SEQ ID NO: 122. In some aspects, the antibody comprises a $V_H$ sequence comprising a Kabat CDR-H3 sequence comprising, consisting of, or consisting essentially of SEQ ID NO: 123. In some aspects, the antibody comprises a $V_H$ sequence comprising a Kabat CDR-H3 sequence comprising, consisting of, or consisting essentially of SEQ ID NO: 124. In some aspects, the antibody comprises a $V_H$ sequence comprising a Kabat CDR-H3 sequence comprising, consisting of, or consisting essentially of SEQ ID NO: 125. In some aspects, the antibody comprises a $V_H$ sequence comprising a Kabat CDR-H3 sequence comprising, consisting of, or consisting essentially of SEQ ID NO: 126. In some aspects, the antibody comprises a $V_H$ sequence comprising a Kabat CDR-H3 sequence comprising, consisting of, or consisting essentially of SEQ ID NO: 127. In some aspects, the antibody comprises a $V_H$ sequence comprising a Kabat CDR-H3 sequence comprising, consisting of, or consisting essentially of SEQ ID NO: 128. In some aspects, the antibody comprises a $V_H$ sequence comprising a Kabat CDR-H3 sequence comprising, consisting of, or consisting essentially of SEQ ID NO: 129. In some aspects, the antibody comprises a $V_H$ sequence comprising a Kabat CDR-H3 sequence comprising, consisting of, or consisting essentially of SEQ ID NO: 130. In some aspects, the antibody comprises a $V_H$ sequence comprising a Kabat CDR-H3 sequence comprising, consisting of, or consisting essentially of SEQ ID NO: 131. In some aspects, the antibody comprises a $V_H$ sequence comprising a Kabat CDR-H3 sequence comprising, consisting of, or consisting essentially of SEQ ID NO: 309. In some aspects, the antibody comprises a $V_H$ sequence comprising a Kabat CDR-H3 sequence comprising, consisting of, or consisting essentially of SEQ ID NO: 310. In some aspects, the antibody comprises a $V_H$ sequence comprising a Kabat CDR-H3 sequence comprising, consisting of, or consisting essentially of SEQ ID NO: 311. In some aspects, the antibody comprises a $V_H$ sequence comprising a Kabat CDR-H3 sequence comprising, consisting of, or consisting essentially of SEQ ID NO: 312. In some aspects, the antibody comprises a $V_H$ sequence comprising a Kabat CDR-H3 sequence comprising, consisting of, or consisting essentially of SEQ ID NO: 313. In some aspects, the antibody comprises a $V_H$ sequence comprising a Kabat CDR-H3 sequence comprising, consisting of, or consisting essentially of SEQ ID NO: 314. In some aspects, the antibody comprises a $V_H$ sequence comprising a Kabat CDR-H3 sequence comprising, consisting of, or consisting essentially of SEQ ID NO: 315.

2.2.1.2. Kabat CDR-H2

In some embodiments, the antibody comprises a $V_H$ sequence comprising a Kabat CDR-H2 sequence comprising, consisting of, or consisting essentially of a sequence selected from SEQ ID NOs: 84-102 or 331. In some aspects, the antibody comprises a $V_H$ sequence comprising a Kabat CDR-H2 sequence comprising, consisting of, or consisting essentially of SEQ ID NO: 84. In some aspects, the antibody comprises a $V_H$ sequence comprising a Kabat CDR-H2 sequence comprising, consisting of, or consisting essentially of SEQ ID NO: 85. In some aspects, the antibody comprises a $V_H$ sequence comprising a Kabat CDR-H2 sequence comprising, consisting of, or consisting essentially of SEQ ID NO: 86. In some aspects, the antibody comprises a $V_H$ sequence comprising a Kabat CDR-H2 sequence comprising, consisting of, or consisting essentially of SEQ ID NO: 87. In some aspects, the antibody comprises a $V_H$ sequence comprising a Kabat CDR-H2 sequence comprising, consisting of, or consisting essentially of SEQ ID NO: 88. In some aspects, the antibody comprises a $V_H$ sequence comprising a Kabat CDR-H2 sequence comprising, consisting of, or consisting essentially of SEQ ID NO: 89. In some aspects, the antibody comprises a $V_H$ sequence comprising a Kabat CDR-H2 sequence comprising, consisting of, or consisting essentially of SEQ ID NO: 90. In some aspects, the antibody comprises a $V_H$ sequence comprising a Kabat CDR-H2 sequence comprising, consisting of, or consisting essentially of SEQ ID NO: 91. In some aspects, the antibody comprises a $V_H$ sequence comprising a Kabat CDR-H2 sequence comprising, consisting of, or consisting essentially of SEQ ID NO: 92. In some aspects, the antibody comprises a $V_H$ sequence comprising a Kabat CDR-H2 sequence comprising, consisting of, or consisting essentially of SEQ ID NO: 93. In some aspects, the antibody comprises a $V_H$ sequence comprising a Kabat CDR-H2 sequence comprising, consisting of, or consisting essentially of SEQ ID NO: 94. In some aspects, the antibody comprises a $V_H$ sequence comprising a Kabat CDR-H2 sequence comprising, consisting of, or consisting essentially of SEQ ID NO: 95. In some aspects, the antibody comprises a $V_H$ sequence comprising a Kabat CDR-H2 sequence comprising, consisting of, or consisting essentially of SEQ ID NO: 96. In some aspects, the antibody comprises a $V_H$ sequence comprising a Kabat CDR-H2 sequence comprising, consisting of, or consisting essentially of SEQ ID NO: 97. In some aspects, the antibody comprises a $V_H$ sequence comprising a Kabat CDR-H2 sequence comprising, consisting of, or consisting essentially of SEQ ID NO: 98. In some aspects, the antibody comprises a $V_H$ sequence comprising a Kabat CDR-H2 sequence comprising, consisting of, or consisting essentially of SEQ ID NO: 99. In some aspects, the antibody comprises a $V_H$ sequence comprising a Kabat CDR-H2 sequence comprising, consisting of, or consisting essentially of SEQ ID NO: 100. In some aspects, the antibody comprises a $V_H$ sequence comprising a Kabat CDR-H2 sequence comprising, consisting of, or consisting essentially of SEQ ID NO: 101. In some aspects, the antibody comprises a $V_H$ sequence comprising a Kabat CDR-H2 sequence comprising, consisting of, or consisting essentially of SEQ ID NO: 102. In some aspects, the antibody comprises a $V_H$ sequence comprising a Kabat CDR-H2 sequence comprising, consisting of, or consisting essentially of SEQ ID NO: 331.

2.2.1.3. Kabat CDR-H1

In some embodiments, the antibody comprises a $V_H$ sequence comprising a Kabat CDR-H1 sequence comprising, consisting of, or consisting essentially of a sequence selected from SEQ ID NOs: 31-49. In some aspects, the antibody comprises a $V_H$ sequence comprising a Kabat CDR-H1 sequence comprising, consisting of, or consisting essentially of SEQ ID NO: 31. In some aspects, the antibody comprises a $V_H$ sequence comprising a Kabat CDR-H1 sequence comprising, consisting of, or consisting essentially of SEQ ID NO: 32. In some aspects, the antibody comprises a $V_H$ sequence comprising a Kabat CDR-H1 sequence comprising, consisting of, or consisting essentially of SEQ ID NO: 33. In some aspects, the antibody comprises a $V_H$ sequence comprising a Kabat CDR-H1 sequence comprising, consisting of, or consisting essentially of SEQ ID NO: 34 In some aspects, the antibody comprises a $V_H$ sequence comprising a Kabat CDR-H1 sequence comprising, consisting of, or consisting essentially of SEQ ID NO: 35. In some aspects, the antibody comprises a $V_H$ sequence comprising a Kabat CDR-H1 sequence comprising, consisting of, or consisting essentially of SEQ ID NO: 36. In some aspects, the antibody comprises a $V_H$ sequence comprising a Kabat CDR-H1 sequence comprising, consisting of, or consisting essentially of SEQ ID NO: 37. In some aspects, the antibody comprises a $V_H$ sequence comprising a Kabat CDR-H1 sequence comprising, consisting of, or consisting essentially of SEQ ID NO: 38. In some aspects, the antibody comprises a $V_H$ sequence comprising a Kabat CDR-H1 sequence comprising, consisting of, or consisting essentially of SEQ ID NO: 39. In some aspects, the antibody comprises a $V_H$ sequence comprising a Kabat CDR-H1 sequence comprising, consisting of, or consisting essentially of SEQ ID NO: 40. In some aspects, the antibody comprises a $V_H$ sequence comprising a Kabat CDR-H1 sequence comprising, consisting of, or consisting essentially of SEQ ID NO: 41. In some aspects, the antibody comprises a $V_H$ sequence comprising a Kabat CDR-H1 sequence comprising, consisting of, or consisting essentially of SEQ ID NO: 42. In some aspects, the antibody comprises a $V_H$ sequence comprising a Kabat CDR-H1 sequence comprising, consisting of, or consisting essentially of SEQ ID NO: 43. In some aspects, the antibody comprises a $V_H$ sequence comprising a Kabat CDR-H1 sequence comprising, consisting of, or consisting essentially of SEQ ID NO: 44. In some aspects, the antibody comprises a $V_H$ sequence comprising a Kabat CDR-H1 sequence comprising, consisting of, or consisting essentially of SEQ ID NO: 45. In some aspects, the antibody comprises a $V_H$ sequence comprising a Kabat CDR-H1 sequence comprising, consisting of, or consisting essentially of SEQ ID NO: 46. In some aspects, the antibody comprises a $V_H$ sequence comprising a Kabat CDR-H1 sequence comprising, consisting of, or consisting essentially of SEQ ID NO: 47. In some aspects, the antibody comprises a $V_H$ sequence comprising a Kabat CDR-H1 sequence comprising, consisting of, or consisting essentially of SEQ ID NO: 48. In some aspects, the antibody comprises a $V_H$ sequence comprising a Kabat CDR-H1 sequence comprising, consisting of, or consisting essentially of SEQ ID NO: 49.

2.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOs: 113-131 and 309-315, and a Kabat CDR-H2 sequence comprising, consisting of, or consisting essentially of a sequence selected from SEQ ID NOs: 84-102 or 331. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOs: 246-264 and 316-322.

2.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOs: 113-131 and 309-315, and a Kabat CDR-H1 sequence comprising, consisting of, or consisting essentially of a sequence selected from SEQ ID NOs: 31-49. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 246-264 and 316-322.

2.2.1.6. Kabat CDR-H1+Kabat CDR-H2

In some embodiments, the antibody comprises a $V_H$ sequence comprising a Kabat CDR-H1 sequence comprising, consisting of, or consisting essentially of a sequence selected from SEQ ID NOs: 31-49 and a Kabat CDR-H2 sequence comprising, consisting of, or consisting essentially of a sequence selected from SEQ ID NOs: 84-102 or 331. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 246-264.

2.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 31-49, a Kabat CDR-H2 sequence comprising, consisting of, or consisting essentially of a sequence selected from SEQ ID NOs: 84-102 or 331, and a Kabat CDR-H3 sequence comprising, consisting of, or consisting essentially of a sequence selected from SEQ ID NOs: 113-131 and 309-315. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 246-264 and 316-322.

2.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, or 95% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, or 95% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, or 95% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

2.2.1.9. Excluded $V_H$ Sequences Comprising Kabat CDRs

In some embodiments, the $V_H$ sequences provided herein do not comprise certain Kabat CDR-H3, CDR-H2, and/or CDR-H1 sequences.

In some aspects, the Kabat CDR-H3 sequence does not comprise, consist of, or consist essentially of a sequence selected from SEQ ID NOs: 108-112 or 132-136. In some aspects, the Kabat CDR-H3 sequence does not comprise, consist of, or consist essentially of SEQ ID NO: 108. In some aspects, the Kabat CDR-H3 sequence does not comprise, consist of, or consist essentially of SEQ ID NO: 109. In some aspects, the Kabat CDR-H3 sequence does not comprise, consist of, or consist essentially of SEQ ID NO: 110. In some aspects, the Kabat CDR-H3 sequence does not comprise, consist of, or consist essentially of SEQ ID NO: 111. In some aspects, the Kabat CDR-H3 sequence does not comprise, consist of, or consist essentially of SEQ ID NO: 112. In some aspects, the Kabat CDR-H3 sequence does not comprise, consist of, or consist essentially of SEQ ID NO: 132. In some aspects, the Kabat CDR-H3 sequence does not comprise, consist of, or consist essentially of SEQ ID NO: 133. In some aspects, the Kabat CDR-H3 sequence does not comprise, consist of, or consist essentially of SEQ ID NO: 134. In some aspects, the Kabat CDR-H3 sequence does not comprise, consist of, or consist essentially of SEQ ID NO: 135. In some aspects, the Kabat CDR-H3 sequence does not comprise, consist of, or consist essentially of SEQ ID NO: 136.

In some aspects, the Kabat CDR-H2 sequence does not comprise, consist of, or consist essentially of a sequence selected from SEQ ID NOs: 55-59 or 103-107. In some aspects, the Kabat CDR-H2 sequence does not comprise, consist of, or consist essentially of SEQ ID NO: 55. In some aspects, the Kabat CDR-H2 sequence does not comprise, consist of, or consist essentially of SEQ ID NO: 56. In some aspects, the Kabat CDR-H2 sequence does not comprise, consist of, or consist essentially of SEQ ID NO: 57. In some aspects, the Kabat CDR-H2 sequence does not comprise, consist of, or consist essentially of SEQ ID NO: 58. In some aspects, the Kabat CDR-H2 sequence does not comprise, consist of, or consist essentially of SEQ ID NO: 59. In some aspects, the Kabat CDR-H2 sequence does not comprise, consist of, or consist essentially of SEQ ID NO: 103. In some aspects, the Kabat CDR-H2 sequence does not comprise, consist of, or consist essentially of SEQ ID NO: 104. In some aspects, the Kabat CDR-H2 sequence does not comprise, consist of, or consist essentially of SEQ ID NO: 105. In some aspects, the Kabat CDR-H2 sequence does not comprise, consist of, or consist essentially of SEQ ID NO: 106. In some aspects, the Kabat CDR-H2 sequence does not comprise, consist of, or consist essentially of SEQ ID NO: 107.

In some aspects, the Kabat CDR-H1 sequence does not comprise, consist of, or consist essentially of a sequence selected from SEQ ID NOs: 2-6 or 50-54. In some aspects, the Kabat CDR-H1 sequence does not comprise, consist of, or consist essentially of SEQ ID NO: 2. In some aspects, the Kabat CDR-H1 sequence does not comprise, consist of, or consist essentially of SEQ ID NO: 3. In some aspects, the Kabat CDR-H1 sequence does not comprise, consist of, or consist essentially of SEQ ID NO: 4. In some aspects, the Kabat CDR-H1 sequence does not comprise, consist of, or consist essentially of SEQ ID NO: 5. In some aspects, the Kabat CDR-H1 sequence does not comprise, consist of, or consist essentially of SEQ ID NO: 6. In some aspects, the Kabat CDR-H1 sequence does not comprise, consist of, or consist essentially of SEQ ID NO: 50. In some aspects, the Kabat CDR-H1 sequence does not comprise, consist of, or consist essentially of SEQ ID NO: 51. In some aspects, the Kabat CDR-H1 sequence does not comprise, consist of, or consist essentially of SEQ ID NO: 52. In some aspects, the Kabat CDR-H1 sequence does not comprise, consist of, or consist essentially of SEQ ID NO: 53. In some aspects, the Kabat CDR-H1 sequence does not comprise, consist of, or consist essentially of SEQ ID NO: 54.

2.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

2.2.2.1. Chothia CDR-H3

In some embodiments, the antibody comprises a $V_H$ sequence comprising a Chothia CDR-H3 sequence comprising, consisting of, or consisting essentially of a sequence selected from SEQ ID NOs: 113-131 and 309-315. In some aspects, the antibody comprises a $V_H$ sequence comprising a Chothia CDR-H3 sequence comprising, consisting of, or consisting essentially of SEQ ID NO: 113. In some aspects, the antibody comprises a $V_H$ sequence comprising a Chothia CDR-H3 sequence comprising, consisting of, or consisting essentially of SEQ ID NO: 114. In some aspects, the antibody comprises a $V_H$ sequence comprising a Chothia CDR-H3 sequence comprising, consisting of, or consisting essentially of SEQ ID NO: 115. In some aspects, the antibody comprises a $V_H$ sequence comprising a Chothia CDR-H3 sequence comprising, consisting of, or consisting essentially of SEQ ID NO: 116. In some aspects, the antibody comprises a $V_H$ sequence comprising a Chothia CDR-H3 sequence comprising, consisting of, or consisting essentially of SEQ ID NO: 117. In some aspects, the antibody comprises a $V_H$ sequence comprising a Chothia CDR-H3 sequence comprising, consisting of, or consisting essentially of SEQ ID NO: 118. In some aspects, the antibody comprises a $V_H$ sequence comprising a Chothia CDR-H3 sequence comprising, consisting of, or consisting essentially of SEQ ID NO: 119. In some aspects, the antibody comprises a $V_H$ sequence comprising a Chothia CDR-H3 sequence comprising, consisting of, or consisting essentially of SEQ ID NO: 120. In some aspects, the antibody comprises a $V_H$ sequence comprising a Chothia CDR-H3 sequence comprising, consisting of, or consisting essentially of SEQ ID NO: 121. In some aspects, the antibody comprises a $V_H$ sequence comprising a Chothia CDR-H3 sequence comprising, consisting of, or consisting essentially of SEQ ID NO: 122. In some aspects, the antibody comprises a $V_H$ sequence comprising a Chothia CDR-H3 sequence comprising, consisting of, or consisting essentially of SEQ ID NO: 123. In some aspects, the antibody comprises a $V_H$ sequence comprising a Chothia CDR-H3 sequence comprising, consisting of, or consisting essentially of SEQ ID NO: 124. In some aspects, the antibody comprises a $V_H$ sequence comprising a Chothia CDR-H3 sequence comprising, consisting of, or consisting essentially of SEQ ID NO: 125. In some aspects, the antibody comprises a $V_H$ sequence comprising a Chothia CDR-H3 sequence comprising, consisting of, or consisting essentially of SEQ ID NO: 126. In some aspects, the antibody comprises a $V_H$ sequence comprising a Chothia CDR-H3 sequence comprising, consisting of, or consisting essentially of SEQ ID NO: 127. In some aspects, the antibody comprises a $V_H$ sequence comprising a Chothia CDR-H3 sequence comprising, consisting of, or consisting essentially of SEQ ID NO: 128. In some aspects, the antibody comprises a $V_H$ sequence comprising a Chothia CDR-H3 sequence comprising, consisting of, or consisting essentially of SEQ ID NO: 129. In some aspects, the antibody comprises a $V_H$ sequence comprising a Chothia CDR-H3 sequence comprising, consisting of, or consisting essentially of SEQ ID NO: 130. In some aspects, the antibody comprises a $V_H$ sequence comprising a Chothia CDR-H3 sequence comprising, consisting of, or consisting essentially of SEQ ID NO: 131. In some aspects, the antibody comprises a $V_H$ sequence comprising a Chothia CDR-H3 sequence comprising, consisting of, or consisting essentially of SEQ ID NO: 309. In some aspects, the antibody comprises a $V_H$ sequence comprising a Chothia CDR-H3 sequence comprising, consisting of, or consisting essentially of SEQ ID NO: 310. In some aspects, the antibody comprises a $V_H$ sequence comprising a Chothia CDR-H3 sequence comprising, consisting of, or consisting essentially of SEQ ID NO: 311. In some aspects, the antibody comprises a $V_H$ sequence comprising a Chothia CDR-H3 sequence comprising, consisting of, or consisting essentially of SEQ ID NO: 312. In some aspects, the antibody comprises a $V_H$ sequence comprising a Chothia CDR-H3 sequence comprising, consisting of, or consisting essentially of SEQ ID NO: 313. In some aspects, the antibody comprises a $V_H$ sequence comprising a Chothia CDR-H3 sequence comprising, consisting of, or consisting essentially of SEQ ID NO: 314. In some aspects, the antibody comprises a $V_H$ sequence comprising a Chothia CDR-H3 sequence comprising, consisting of, or consisting essentially of SEQ ID NO: 315.

2.2.2.2. Chothia CDR-H2

In some embodiments, the antibody comprises a $V_H$ sequence comprising a Chothia CDR-H2 sequence comprising, consisting of, or consisting essentially of a sequence selected from SEQ ID NOs: 60-78. In some aspects, the antibody comprises a $V_H$ sequence comprising a Chothia CDR-H2 sequence comprising, consisting of, or consisting essentially of SEQ ID NO: 60. In some aspects, the antibody comprises a $V_H$ sequence comprising a Chothia CDR-H2 sequence comprising, consisting of, or consisting essentially of SEQ ID NO: 61. In some aspects, the antibody comprises a $V_H$ sequence comprising a Chothia CDR-H2 sequence comprising, consisting of, or consisting essentially of SEQ ID NO: 62. In some aspects, the antibody comprises a $V_H$ sequence comprising a Chothia CDR-H2 sequence comprising, consisting of, or consisting essentially of SEQ ID NO: 63. In some aspects, the antibody comprises a $V_H$ sequence comprising a Chothia CDR-H2 sequence comprising, consisting of, or consisting essentially of SEQ ID NO: 64. In some aspects, the antibody comprises a $V_H$ sequence comprising a Chothia CDR-H2 sequence comprising, consisting of, or consisting essentially of SEQ ID NO: 65. In some aspects, the antibody comprises a $V_H$ sequence comprising a Chothia CDR-H2 sequence comprising, consisting of, or consisting essentially of SEQ ID NO: 66. In some aspects, the antibody comprises a $V_H$ sequence comprising a Chothia CDR-H2 sequence comprising, consisting of, or consisting essentially of SEQ ID NO: 67. In some aspects, the antibody comprises a $V_H$ sequence comprising a Chothia CDR-H2 sequence comprising, consisting of, or consisting essentially of SEQ ID NO: 68. In some aspects, the antibody comprises a $V_H$ sequence comprising a Chothia CDR-H2 sequence comprising, consisting of, or consisting essentially of SEQ ID NO: 69. In some aspects, the antibody comprises a $V_H$ sequence comprising a Chothia CDR-H2 sequence comprising, consisting of, or consisting essentially of SEQ ID NO: 70. In some aspects, the antibody comprises a $V_H$ sequence comprising a Chothia CDR-H2 sequence comprising, consisting of, or consisting essentially of SEQ ID NO: 71. In some aspects, the antibody comprises a $V_H$ sequence comprising a Chothia CDR-H2 sequence comprising, consisting of, or consisting essentially of SEQ ID NO: 72. In some aspects, the antibody comprises a $V_H$ sequence comprising a Chothia CDR-H2 sequence comprising, consisting of, or consisting essentially of SEQ ID NO: 73. In some aspects, the antibody comprises a $V_H$ sequence comprising a Chothia CDR-H2 sequence comprising, consisting of, or consisting essentially of SEQ ID NO: 74. In some aspects, the antibody comprises a $V_H$ sequence comprising a Chothia CDR-H2 sequence comprising, consisting of, or consisting essentially of SEQ ID NO: 75. In some aspects, the antibody comprises a $V_H$ sequence comprising a Chothia CDR-H2 sequence comprising, consisting of, or consisting essentially of SEQ ID NO: 76. In some aspects, the antibody comprises a $V_H$ sequence comprising a Chothia CDR-H2 sequence comprising, consisting of, or consisting essentially of SEQ ID NO: 77. In some aspects, the antibody comprises a $V_H$ sequence comprising a Chothia CDR-H2 sequence comprising, consisting of, or consisting essentially of SEQ ID NO: 78.

2.2.2.3. Chothia CDR-H1

In some embodiments, the antibody comprises a $V_H$ sequence comprising a Chothia CDR-H1 sequence comprising, consisting of, or consisting essentially of a sequence selected from SEQ ID NOs: 7-25. In some aspects, the antibody comprises a $V_H$ sequence comprising a Chothia CDR-H1 sequence comprising, consisting of, or consisting essentially of SEQ ID NO: 7. In some aspects, the antibody comprises a $V_H$ sequence comprising a Chothia CDR-H1 sequence comprising, consisting of, or consisting essentially of SEQ ID NO: 8. In some aspects, the antibody comprises a $V_H$ sequence comprising a Chothia CDR-H1 sequence comprising, consisting of, or consisting essentially of SEQ ID NO: 9. In some aspects, the antibody comprises a $V_H$ sequence comprising a Chothia CDR-H1 sequence comprising, consisting of, or consisting essentially of SEQ ID NO: 10 In some aspects, the antibody comprises a $V_H$ sequence comprising a Chothia CDR-H1 sequence comprising, consisting of, or consisting essentially of SEQ ID NO: 11. In some aspects, the antibody comprises a $V_H$ sequence comprising a Chothia CDR-H1 sequence comprising, consisting of, or consisting essentially of SEQ ID NO: 12. In some aspects, the antibody comprises a $V_H$ sequence comprising a Chothia CDR-H1 sequence comprising, consisting of, or consisting essentially of SEQ ID NO: 13. In some aspects, the antibody comprises a $V_H$ sequence comprising a Chothia CDR-H1 sequence comprising, consisting of, or consisting essentially of SEQ ID NO: 14. In some aspects, the antibody comprises a $V_H$ sequence comprising a Chothia CDR-H1 sequence comprising, consisting of, or consisting essentially of SEQ ID NO: 15. In some aspects, the antibody comprises a $V_H$ sequence comprising a Chothia CDR-H1 sequence comprising, consisting of, or consisting essentially of SEQ ID NO: 16. In some aspects, the antibody comprises a $V_H$ sequence comprising a Chothia CDR-H1 sequence comprising, consisting of, or consisting essentially of SEQ ID NO: 17. In some aspects, the antibody comprises a $V_H$ sequence comprising a Chothia CDR-H1 sequence comprising, consisting of, or consisting essentially of SEQ ID NO: 18. In some aspects, the antibody comprises a $V_H$ sequence comprising a Chothia CDR-H1 sequence comprising, consisting of, or consisting essentially of SEQ ID NO: 19. In some aspects, the antibody comprises a $V_H$ sequence comprising a Chothia CDR-H1 sequence comprising, consisting of, or consisting essentially of SEQ ID NO: 20. In some aspects, the antibody comprises a $V_H$ sequence comprising a Chothia CDR-H1 sequence comprising, consisting of, or consisting essentially of SEQ ID NO: 21. In some aspects, the antibody comprises a $V_H$ sequence comprising a Chothia CDR-H1 sequence comprising, consisting of, or consisting essentially of SEQ ID NO: 22. In some aspects, the antibody comprises a $V_H$ sequence comprising a Chothia CDR-H1 sequence comprising, consisting of, or consisting essentially of SEQ ID NO: 23. In some aspects, the antibody comprises a $V_H$ sequence comprising a Chothia CDR-H1 sequence comprising, consisting of, or consisting essentially of SEQ ID NO: 24. In some aspects, the antibody comprises a $V_H$ sequence comprising a Chothia CDR-H1 sequence comprising, consisting of, or consisting essentially of SEQ ID NO: 25.

2.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOs: 113-131 and 309-315, and a Chothia CDR-H2 sequence comprising, consisting of, or consisting essentially of a sequence selected from SEQ ID NOs: 60-78. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOs: 246-264 and 316-322.

2.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOs: 113-131 and 309-315, and a Chothia CDR-H1 sequence comprising, consisting of, or consisting essentially of a sequence selected from SEQ ID NOs: 7-25. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOs: 246-264 and 316-322.

2.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOs: 7-25 and a Chothia CDR-H2 sequence comprising, consisting of, or consisting essentially of a sequence selected from SEQ ID NOs: 60-78. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOs: 246-264.

2.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 7-25, a Chothia CDR-H2 sequence comprising, consisting of, or consisting essentially of a sequence selected from SEQ ID NOs: 60-78, and a Chothia CDR-H3 sequence comprising, consisting of, or consisting essentially of a sequence selected from SEQ ID NOs: 113-131 and 309-315. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 246-264 and 316-322.

2.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, or 95% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, or 95% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, or 95% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

2.2.2.9. Excluded $V_H$ Sequences Comprising Chothia CDRs

In some embodiments, the $V_H$ sequences provided herein do not comprise certain Chothia CDR-H3, CDR-H2, and/or CDR-H1 sequences.

In some aspects, the Chothia CDR-H3 sequence does not comprise, consist of, or consist essentially of a sequence selected from SEQ ID NOs: 108-112 or 132-136. In some aspects, the Chothia CDR-H3 sequence does not comprise, consist of, or consist essentially of SEQ ID NO: 108. In some aspects, the Chothia CDR-H3 sequence does not comprise, consist of, or consist essentially of SEQ ID NO: 109. In some aspects, the Chothia CDR-H3 sequence does not comprise, consist of, or consist essentially of SEQ ID NO: 110. In some aspects, the Chothia CDR-H3 sequence does not comprise, consist of, or consist essentially of SEQ ID NO: 111. In some aspects, the Chothia CDR-H3 sequence does not comprise, consist of, or consist essentially of SEQ ID NO: 112. In some aspects, the Chothia CDR-H3 sequence does not comprise, consist of, or consist essentially of SEQ ID NO: 132. In some aspects, the Chothia CDR-H3 sequence does not comprise, consist of, or consist essentially of SEQ ID NO: 133. In some aspects, the Chothia CDR-H3 sequence does not comprise, consist of, or consist essentially of SEQ ID NO: 134. In some aspects, the Chothia CDR-H3 sequence does not comprise, consist of, or consist essentially of SEQ ID NO: 135. In some aspects, the Chothia CDR-H3 sequence does not comprise, consist of, or consist essentially of SEQ ID NO: 136.

In some aspects, the Chothia CDR-H2 sequence does not comprise, consist of, or consist essentially of a sequence selected from SEQ ID NOs: 79-83. In some aspects, the Chothia CDR-H2 sequence does not comprise, consist of, or consist essentially of SEQ ID NO: 79. In some aspects, the Chothia CDR-H2 sequence does not comprise, consist of, or consist essentially of SEQ ID NO: 80. In some aspects, the Chothia CDR-H2 sequence does not comprise, consist of, or consist essentially of SEQ ID NO: 81. In some aspects, the Chothia CDR-H2 sequence does not comprise, consist of, or consist essentially of SEQ ID NO: 82. In some aspects, the Chothia CDR-H2 sequence does not comprise, consist of, or consist essentially of SEQ ID NO: 83.

In some aspects, the Chothia CDR-H1 sequence does not comprise, consist of, or consist essentially of a sequence selected from SEQ ID NOs: 26-30. In some aspects, the Chothia CDR-H1 sequence does not comprise, consist of, or consist essentially of SEQ ID NO: 26. In some aspects, the Chothia CDR-H1 sequence does not comprise, consist of, or consist essentially of SEQ ID NO: 27. In some aspects, the Chothia CDR-H1 sequence does not comprise, consist of, or consist essentially of SEQ ID NO: 28. In some aspects, the Chothia CDR-H1 sequence does not comprise, consist of, or consist essentially of SEQ ID NO: 29. In some aspects, the Chothia CDR-H1 sequence does not comprise, consist of, or consist essentially of SEQ ID NO: 30.

2.3. $V_H$ Sequences

In some embodiments, the antibody comprises a $V_H$ sequence comprising, consisting of, or consisting essentially of a sequence selected from SEQ ID NOs: 246-264 and 316-322. In some aspects, the antibody comprises a $V_H$ sequence comprising, consisting of, or consisting essentially of SEQ ID NO: 246. In some aspects, the antibody comprises a $V_H$ sequence comprising, consisting of, or consisting essentially of SEQ ID NO: 247. In some aspects, the antibody comprises a $V_H$ sequence comprising, consisting of, or consisting essentially of SEQ ID NO: 248. In some aspects, the antibody comprises a V$_H$ sequence comprising, consisting of, or consisting essentially of SEQ ID NO: 249. In some aspects, the antibody comprises a V$_H$ sequence comprising, consisting of, or consisting essentially of SEQ ID NO: 250. In some aspects, the antibody comprises a V$_H$ sequence comprising, consisting of, or consisting essentially of SEQ ID NO: 251. In some aspects, the antibody comprises a V$_H$ sequence comprising, consisting of, or consisting essentially of SEQ ID NO: 252. In some aspects, the antibody comprises a V$_H$ sequence comprising, consisting of, or consisting essentially of SEQ ID NO: 253. In some aspects, the antibody comprises a V$_H$ sequence comprising, consisting of, or consisting essentially of SEQ ID NO: 254. In some aspects, the antibody comprises a V$_H$ sequence comprising, consisting of, or consisting essentially of SEQ ID NO: 255 (with or without a serine prepended to the sequence). In some aspects, the antibody comprises a V$_H$ sequence comprising, consisting of, or consisting essentially of SEQ ID NO: 256. In some aspects, the antibody comprises a V$_H$ sequence comprising, consisting of, or consisting essentially of SEQ ID NO: 257. In some aspects, the antibody comprises a V$_H$ sequence comprising, consisting of, or consisting essentially of SEQ ID NO: 258. In some aspects, the antibody comprises a V$_H$ sequence comprising, consisting of, or consisting essentially of SEQ ID NO: 259. In some aspects, the antibody comprises a V$_H$ sequence comprising, consisting of, or consisting essentially of SEQ ID NO: 260. In some aspects, the antibody comprises a V$_H$ sequence comprising, consisting of, or consisting essentially of SEQ ID NO: 261. In some aspects, the antibody comprises a V$_H$ sequence comprising, consisting of, or consisting essentially of SEQ ID NO: 262. In some aspects, the antibody comprises a V$_H$ sequence comprising, consisting of, or consisting essentially of SEQ ID NO: 263. In some aspects, the antibody comprises a V$_H$ sequence comprising, consisting of, or consisting essentially of SEQ ID NO: 264. In some aspects, the antibody comprises a V$_H$ sequence comprising, consisting of, or consisting essentially of SEQ ID NO: 316. In some aspects, the antibody comprises a V$_H$ sequence comprising, consisting of, or consisting essentially of SEQ ID NO: 317. In some aspects, the antibody comprises a V$_H$ sequence comprising, consisting of, or consisting essentially of SEQ ID NO: 318. In some aspects, the antibody comprises a V$_H$ sequence comprising, consisting of, or consisting essentially of SEQ ID NO: 319. In some aspects, the antibody comprises a V$_H$ sequence comprising, consisting of, or consisting essentially of SEQ ID NO: 320. In some aspects, the antibody comprises a V$_H$ sequence comprising, consisting of, or consisting essentially of SEQ ID NO: 321. In some aspects, the antibody comprises a V$_H$ sequence comprising, consisting of, or consisting essentially of SEQ ID NO: 322.

2.3.1. Variants of V$_H$ Sequences

In some embodiments, the V$_H$ sequences provided herein comprise, consist of, or consist essentially of a variant of an illustrative V$_H$ sequence provided in this disclosure.

In some aspects, the V$_H$ sequence comprises, consists of, or consists essentially of a variant of an illustrative V$_H$ sequence provided in this disclosure. In some aspects, the V$_H$ sequence comprises, consists of, or consists essentially of a sequence having at least 85%, 90%, 95%, 96%, 97%, 98%, 99%, or 99.5% identity with any of the illustrative V$_H$ sequences provided in this disclosure.

In some embodiments, the V$_H$ sequence comprises, consists of, or consists essentially of any of the illustrative V$_H$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.3.2. Excluded V$_H$ Sequences

In some embodiments, the V$_H$ sequences provided herein do not comprise certain V$_H$ sequences.

In some aspects, the V$_H$ sequence does not comprise, consist of, or consist essentially of a sequence selected from SEQ ID NOs: 265-269. In some aspects, the V$_H$ sequence does not comprise, consist of, or consist essentially of SEQ ID NO: 265. In some aspects, the V$_H$ sequence does not comprise, consist of, or consist essentially of SEQ ID NO: 266. In some aspects, the V$_H$ sequence does not comprise, consist of, or consist essentially of SEQ ID NO: 267. In some aspects, the V$_H$ sequence does not comprise, consist of, or consist essentially of SEQ ID NO: 268. In some aspects, the V$_H$ sequence does not comprise, consist of, or consist essentially of SEQ ID NO: 269.

2.4. CDR-L3 Sequences

In some embodiments, the antibody comprises a CDR-L3 sequence comprising, consisting of, or consisting essentially of a sequence selected from SEQ ID NOs: 200-218. In some aspects, the antibody comprises a CDR-L3 sequence comprising, consisting of, or consisting essentially of SEQ ID NO: 200. In some aspects, the antibody comprises a CDR-L3 sequence comprising, consisting of, or consisting essentially of SEQ ID NO: 201. In some aspects, the antibody comprises a CDR-L3 sequence comprising, consisting of, or consisting essentially of SEQ ID NO: 202. In some aspects, the antibody comprises a CDR-L3 sequence comprising, consisting of, or consisting essentially of SEQ ID NO: 203. In some aspects, the antibody comprises a CDR-L3 sequence comprising, consisting of, or consisting essentially of SEQ ID NO: 204. In some aspects, the antibody comprises a CDR-L3 sequence comprising, consisting of, or consisting essentially of SEQ ID NO: 205. In some aspects, the antibody comprises a CDR-L3 sequence comprising, consisting of, or consisting essentially of SEQ ID NO: 206. In some aspects, the antibody comprises a CDR-L3 sequence comprising, consisting of, or consisting essentially of SEQ ID NO: 207. In some aspects, the antibody comprises a CDR-L3 sequence comprising, consisting of, or consisting essentially of SEQ ID NO: 208. In some aspects, the antibody comprises a CDR-L3 sequence comprising, consisting of, or consisting essentially of SEQ ID NO: 209. In some aspects, the antibody comprises a CDR-L3 sequence comprising, consisting of, or consisting essentially of SEQ ID NO: 210. In some aspects, the antibody comprises a CDR-L3 sequence comprising, consisting of, or consisting essentially of SEQ ID NO: 211. In some aspects, the antibody comprises a CDR-L3 sequence comprising, consisting of, or consisting essentially of SEQ ID NO: 212. In some aspects, the antibody comprises a CDR-L3 sequence comprising, consisting of, or consisting essentially of SEQ ID NO: 213. In some aspects, the antibody comprises a CDR-L3 sequence comprising, consisting of, or consisting essentially of SEQ ID NO: 214. In some aspects, the antibody comprises a CDR-L3 sequence comprising, consisting of, or consisting essentially of SEQ ID NO: 215. In some aspects, the antibody comprises a CDR-L3 sequence comprising, consisting of, or consisting essentially of SEQ ID NO: 216. In some aspects, the antibody comprises a CDR-L3 sequence comprising, consisting of, or consisting essentially of SEQ ID NO: 217. In some aspects, the antibody comprises a CDR-L3 sequence comprising, consisting of, or consisting essentially of SEQ ID NO: 218.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L3 sequence does not comprise, consist of, or consist essentially of a sequence selected from SEQ ID NOs: 195-199 or 219-223. In some aspects the CDR-L3 sequence does not comprise, consist of, or consist essentially of SEQ ID NO: 195. In some aspects the CDR-L3 sequence does not comprise, consist of, or consist essentially of SEQ ID NO: 196. In some aspects the CDR-L3 sequence does not comprise, consist of, or consist essentially of SEQ ID NO: 197. In some aspects the CDR-L3 sequence does not comprise, consist of, or consist essentially of SEQ ID NO: 198. In some aspects the CDR-L3 sequence does not comprise, consist of, or consist essentially of SEQ ID NO: 199. In some aspects the CDR-L3 sequence does not comprise, consist of, or consist essentially of SEQ ID NO: 219. In some aspects the CDR-L3 sequence does not comprise, consist of, or consist essentially of SEQ ID NO: 220. In some aspects the CDR-L3 sequence does not comprise, consist of, or consist essentially of SEQ ID NO: 221. In some aspects the CDR-L3 sequence does not comprise, consist of, or consist essentially of SEQ ID NO: 222. In some aspects the CDR-L3 sequence does not comprise, consist of, or consist essentially of SEQ ID NO: 223.

2.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

2.5.1. CDR-L3

In some embodiments, the antibody comprises a $V_L$ sequence comprising a CDR-L3 sequence comprising, consisting of, or consisting essentially of a sequence selected from SEQ ID NOs: 200-218. In some aspects, the antibody comprises a $V_L$ sequence comprising a CDR-L3 sequence comprising, consisting of, or consisting essentially of SEQ ID NO: 200. In some aspects, the antibody comprises a $V_L$ sequence comprising a CDR-L3 sequence comprising, consisting of, or consisting essentially of SEQ ID NO: 201. In some aspects, the antibody comprises a $V_L$ sequence comprising a CDR-L3 sequence comprising, consisting of, or consisting essentially of SEQ ID NO: 202. In some aspects, the antibody comprises a $V_L$ sequence comprising a CDR-L3 sequence comprising, consisting of, or consisting essentially of SEQ ID NO: 203. In some aspects, the antibody comprises a $V_L$ sequence comprising a CDR-L3 sequence comprising, consisting of, or consisting essentially of SEQ ID NO: 204. In some aspects, the antibody comprises a $V_L$ sequence comprising a CDR-L3 sequence comprising, consisting of, or consisting essentially of SEQ ID NO: 205. In some aspects, the antibody comprises a $V_L$ sequence comprising a CDR-L3 sequence comprising, consisting of, or consisting essentially of SEQ ID NO: 206. In some aspects, the antibody comprises a $V_L$ sequence comprising a CDR-L3 sequence comprising, consisting of, or consisting essentially of SEQ ID NO: 207. In some aspects, the antibody comprises a $V_L$ sequence comprising a CDR-L3 sequence comprising, consisting of, or consisting essentially of SEQ ID NO: 208. In some aspects, the antibody comprises a $V_L$ sequence comprising a CDR-L3 sequence comprising, consisting of, or consisting essentially of SEQ ID NO: 209. In some aspects, the antibody comprises a $V_L$ sequence comprising a CDR-L3 sequence comprising, consisting of, or consisting essentially of SEQ ID NO: 210. In some aspects, the antibody comprises a $V_L$ sequence comprising a CDR-L3 sequence comprising, consisting of, or consisting essentially of SEQ ID NO: 211. In some aspects, the antibody comprises a $V_L$ sequence comprising a CDR-L3 sequence comprising, consisting of, or consisting essentially of SEQ ID NO: 212. In some aspects, the antibody comprises a $V_L$ sequence comprising a CDR-L3 sequence comprising, consisting of, or consisting essentially of SEQ ID NO: 213. In some aspects, the antibody comprises a $V_L$ sequence comprising a CDR-L3 sequence comprising, consisting of, or consisting essentially of SEQ ID NO: 214. In some aspects, the antibody comprises a $V_L$ sequence comprising a CDR-L3 sequence comprising, consisting of, or consisting essentially of SEQ ID NO: 215. In some aspects, the antibody comprises a $V_L$ sequence comprising a CDR-L3 sequence comprising, consisting of, or consisting essentially of SEQ ID NO: 216. In some aspects, the antibody comprises a $V_L$ sequence comprising a CDR-L3 sequence comprising, consisting of, or consisting essentially of SEQ ID NO: 217. In some aspects, the antibody comprises a $V_L$ sequence comprising a CDR-L3 sequence comprising, consisting of, or consisting essentially of SEQ ID NO: 218.

2.5.2. CDR-L2

In some embodiments, the antibody comprises a $V_L$ sequence comprising a CDR-L2 sequence comprising, consisting of, or consisting essentially of a sequence selected from SEQ ID NOs: 171-189. In some aspects, the antibody comprises a $V_L$ sequence comprising a CDR-L2 sequence comprising, consisting of, or consisting essentially of SEQ ID NO: 171. In some aspects, the antibody comprises a $V_L$ sequence comprising a CDR-L2 sequence comprising, consisting of, or consisting essentially of SEQ ID NO: 172. In some aspects, the antibody comprises a $V_L$ sequence comprising a CDR-L2 sequence comprising, consisting of, or consisting essentially of SEQ ID NO: 173. In some aspects, the antibody comprises a $V_L$ sequence comprising a CDR-L2 sequence comprising, consisting of, or consisting essentially of SEQ ID NO: 174. In some aspects, the antibody comprises a $V_L$ sequence comprising a CDR-L2 sequence comprising, consisting of, or consisting essentially of SEQ ID NO: 175. In some aspects, the antibody comprises a $V_L$ sequence comprising a CDR-L2 sequence comprising, consisting of, or consisting essentially of SEQ ID NO: 176. In some aspects, the antibody comprises a $V_L$ sequence comprising a CDR-L2 sequence comprising, consisting of, or consisting essentially of SEQ ID NO: 177. In some aspects, the antibody comprises a $V_L$ sequence comprising a CDR-L2 sequence comprising, consisting of, or consisting essentially of SEQ ID NO: 178. In some aspects, the antibody comprises a $V_L$ sequence comprising a CDR-L2 sequence comprising, consisting of, or consisting essentially of SEQ ID NO: 179. In some aspects, the antibody comprises a $V_L$ sequence comprising a CDR-L2 sequence comprising, consisting of, or consisting essentially of SEQ ID NO: 180. In some aspects, the antibody comprises a $V_L$ sequence comprising a CDR-L2 sequence comprising, consisting of, or consisting essentially of SEQ ID NO: 181. In some aspects, the antibody comprises a $V_L$ sequence comprising a CDR-L2 sequence comprising, consisting of, or consisting essentially of SEQ ID NO: 182. In some aspects, the antibody comprises a $V_L$ sequence comprising a CDR-L2 sequence comprising, consisting of, or consisting essentially of SEQ ID NO: 183. In some aspects, the antibody comprises a $V_L$ sequence comprising a CDR-L2 sequence comprising, consisting of, or consisting essentially of SEQ ID NO: 184. In some aspects, the antibody comprises a $V_L$ sequence comprising a CDR-L2 sequence comprising, consisting of, or consisting essentially of SEQ ID NO: 185. In some aspects, the antibody comprises a $V_L$ sequence comprising a CDR-L2 sequence comprising, consisting of, or consisting essentially of SEQ ID NO: 186. In some aspects, the antibody comprises a $V_L$ sequence comprising a CDR-L2 sequence comprising, consisting of, or consisting essentially of SEQ ID NO: 187. In some aspects, the antibody comprises a $V_L$ sequence comprising a CDR-L2 sequence comprising, consisting of, or consisting essentially of SEQ ID NO: 188. In some aspects, the antibody comprises a $V_L$ sequence comprising a CDR-L2 sequence comprising, consisting of, or consisting essentially of SEQ ID NO: 189.

2.5.3. CDR-L1

In some embodiments, the antibody comprises a $V_L$ sequence comprising a CDR-L1 sequence comprising, consisting of, or consisting essentially of a sequence selected from SEQ ID NOs: 142-160. In some aspects, the antibody comprises a $V_L$ sequence comprising a CDR-L1 sequence comprising, consisting of, or consisting essentially of SEQ ID NO: 142. In some aspects, the antibody comprises a $V_L$ sequence comprising a CDR-L1 sequence comprising, consisting of, or consisting essentially of SEQ ID NO: 143. In some aspects, the antibody comprises a $V_L$ sequence comprising a CDR-L1 sequence comprising, consisting of, or consisting essentially of SEQ ID NO: 144. In some aspects, the antibody comprises a $V_L$ sequence comprising a CDR-L1 sequence comprising, consisting of, or consisting essentially of SEQ ID NO: 145. In some aspects, the antibody comprises a $V_L$ sequence comprising a CDR-L1 sequence comprising, consisting of, or consisting essentially of SEQ ID NO: 146. In some aspects, the antibody comprises a $V_L$ sequence comprising a CDR-L1 sequence comprising, consisting of, or consisting essentially of SEQ ID NO: 147. In some aspects, the antibody comprises a $V_L$ sequence comprising a CDR-L1 sequence comprising, consisting of, or consisting essentially of SEQ ID NO: 148. In some aspects, the antibody comprises a $V_L$ sequence comprising a CDR-L1 sequence comprising, consisting of, or consisting essentially of SEQ ID NO: 149. In some aspects, the antibody comprises a $V_L$ sequence comprising a CDR-L1 sequence comprising, consisting of, or consisting essentially of SEQ ID NO: 150. In some aspects, the antibody comprises a $V_L$ sequence comprising a CDR-L1 sequence comprising, consisting of, or consisting essentially of SEQ ID NO: 151. In some aspects, the antibody comprises a $V_L$ sequence comprising a CDR-L1 sequence comprising, consisting of, or consisting essentially of SEQ ID NO: 152. In some aspects, the antibody comprises a $V_L$ sequence comprising a CDR-L1 sequence comprising, consisting of, or consisting essentially of SEQ ID NO: 153. In some aspects, the antibody comprises a $V_L$ sequence comprising a CDR-L1 sequence comprising, consisting of, or consisting essentially of SEQ ID NO: 154. In some aspects, the antibody comprises a $V_L$ sequence comprising a CDR-L1 sequence comprising, consisting of, or consisting essentially of SEQ ID NO: 155. In some aspects, the antibody comprises a $V_L$ sequence comprising a CDR-L1 sequence comprising, consisting of, or consisting essentially of SEQ ID NO: 156. In some aspects, the antibody comprises a $V_L$ sequence comprising a CDR-L1 sequence comprising, consisting of, or consisting essentially of SEQ ID NO: 157. In some aspects, the antibody comprises a $V_L$ sequence comprising a CDR-L1 sequence comprising, consisting of, or consisting essentially of SEQ ID NO: 158. In some aspects, the antibody comprises a $V_L$ sequence comprising a CDR-L1 sequence comprising, consisting of, or consisting essentially of SEQ ID NO: 159. In some aspects, the antibody comprises a $V_L$ sequence comprising a CDR-L1 sequence comprising, consisting of, or consisting essentially of SEQ ID NO: 160.

2.5.4. CDR-L3+CDR-L2

In some embodiments, the antibody comprises a $V_L$ sequence comprising a CDR-L3 sequence comprising, consisting of, or consisting essentially of a sequence selected from SEQ ID NOs: 200-218 and a CDR-L2 sequence comprising, consisting of, or consisting essentially of a sequence selected from SEQ ID NOs: 171-189. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs: 270-288.

2.5.5. CDR-L3+CDR-L1

In some embodiments, the antibody comprises a $V_L$ sequence comprising a CDR-L3 sequence comprising, consisting of, or consisting essentially of a sequence selected from SEQ ID NOs: 200-218 and a CDR-L1 sequence comprising, consisting of, or consisting essentially of a sequence selected from SEQ ID NOs: 142-160. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs: 270-288.

2.5.6. CDR-L1+CDR-L2

In some embodiments, the antibody comprises a $V_L$ sequence comprising a CDR-L1 sequence comprising, consisting of, or consisting essentially of a sequence selected from SEQ ID NOs: 142-160 and a CDR-L2 sequence comprising, consisting of, or consisting essentially of a sequence selected from SEQ ID NOs: 171-189. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs: 270-288.

2.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOs: 142-160, a CDR-L2 sequence comprising, consisting of, or consisting essentially of a sequence selected from SEQ ID NOs: 171-189, and a CDR-L3 sequence comprising, consisting of, or consisting essentially of a sequence selected from SEQ ID NOs: 200-218. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs: 270-288.

2.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.5.9. Excluded $V_L$ Sequences Comprising CDR-Ls

In some embodiments, the $V_L$ sequences provided herein do not comprise certain CDR-L3, CDR-L2, and/or CDR-L1 sequences.

In some aspects, the CDR-L3 sequence does not comprise, consist of, or consist essentially of a sequence selected from SEQ ID NOs: 195-199 or 219-223. In some aspects, the CDR-L3 sequence does not comprise, consist of, or consist essentially of SEQ ID NOs: 195. In some aspects, the CDR-L3 sequence does not comprise, consist of, or consist essentially of SEQ ID NOs: 196. In some aspects, the CDR-L3 sequence does not comprise, consist of, or consist essentially of SEQ ID NOs: 197. In some aspects, the CDR-L3 sequence does not comprise, consist of, or consist essentially of SEQ ID NOs: 198. In some aspects, the CDR-L3 sequence does not comprise, consist of, or consist essentially of SEQ ID NOs: 199. In some aspects, the CDR-L3 sequence does not comprise, consist of, or consist essentially of SEQ ID NOs: 219. In some aspects, the CDR-L3 sequence does not comprise, consist of, or consist essentially of SEQ ID NOs: 220. In some aspects, the CDR-L3 sequence does not comprise, consist of, or consist essentially of SEQ ID NOs: 221. In some aspects, the CDR-L3 sequence does not comprise, consist of, or consist essentially of SEQ ID NOs: 222. In some aspects, the CDR-L3 sequence does not comprise, consist of, or consist essentially of SEQ ID NOs: 223.

In some aspects, the CDR-L2 sequence does not comprise, consist of, or consist essentially of a sequence selected from SEQ ID NOs: 166-170 or 190-194. In some aspects, the CDR-L2 sequence does not comprise, consist of, or consist essentially of SEQ ID NO: 190. In some aspects, the CDR-L2 sequence does not comprise, consist of, or consist essentially of SEQ ID NO: 166. In some aspects, the CDR-L2 sequence does not comprise, consist of, or consist essentially of SEQ ID NO: 167. In some aspects, the CDR-L2 sequence does not comprise, consist of, or consist essentially of SEQ ID NO: 168. In some aspects, the CDR-L2 sequence does not comprise, consist of, or consist essentially of SEQ ID NO: 169. In some aspects, the CDR-L2 sequence does not comprise, consist of, or consist essentially of SEQ ID NO: 170. In some aspects, the CDR-L2 sequence does not comprise, consist of, or consist essentially of SEQ ID NO: 191. In some aspects, the CDR-L2 sequence does not comprise, consist of, or consist essentially of SEQ ID NO: 192. In some aspects, the CDR-L2 sequence does not comprise, consist of, or consist essentially of SEQ ID NO: 193. In some aspects, the CDR-L2 sequence does not comprise, consist of, or consist essentially of SEQ ID NO: 194.

In some aspects, the CDR-L1 sequence does not comprise, consist of, or consist essentially of a sequence selected from SEQ ID NOs: 137-141 or 161-165. In some aspects, the CDR-L1 sequence does not comprise, consist of, or consist essentially of SEQ ID NO: 137. In some aspects, the CDR-L1 sequence does not comprise, consist of, or consist essentially of SEQ ID NO: 138. In some aspects, the CDR-L1 sequence does not comprise, consist of, or consist essentially of SEQ ID NO: 139. In some aspects, the CDR-L1 sequence does not comprise, consist of, or consist essentially of SEQ ID NO: 140. In some aspects, the CDR-L1 sequence does not comprise, consist of, or consist essentially of SEQ ID NO: 141. In some aspects, the CDR-L1 sequence does not comprise, consist of, or consist essentially of SEQ ID NO: 161. In some aspects, the CDR-L1 sequence does not comprise, consist of, or consist essentially of SEQ ID NO: 162. In some aspects, the CDR-L1 sequence does not comprise, consist of, or consist essentially of SEQ ID NO: 163. In some aspects, the CDR-L1 sequence does not comprise, consist of, or consist essentially of SEQ ID NO: 164. In some aspects, the CDR-L1 sequence does not comprise, consist of, or consist essentially of SEQ ID NO: 165.

2.6. $V_L$ Sequences

In some embodiments, the antibody comprises a $V_L$ sequence comprising, consisting of, or consisting essentially of a sequence selected from SEQ ID NOs: 270-288. In some aspects, the antibody comprises a $V_L$ sequence comprising, consisting of, or consisting essentially of SEQ ID NO: 270. In some aspects, the antibody comprises a $V_L$ sequence comprising, consisting of, or consisting essentially of SEQ ID NO: 281. In some aspects, the antibody comprises a $V_L$ sequence comprising, consisting of, or consisting essentially of SEQ ID NO: 282. In some aspects, the antibody comprises a $V_L$ sequence comprising, consisting of, or consisting essentially of SEQ ID NO: 283. In some aspects, the antibody comprises a $V_L$ sequence comprising, consisting of, or consisting essentially of SEQ ID NO: 284. In some aspects, the antibody comprises a $V_L$ sequence comprising, consisting of, or consisting essentially of SEQ ID NO: 285. In some aspects, the antibody comprises a $V_L$ sequence comprising, consisting of, or consisting essentially of SEQ ID NO: 286. In some aspects, the antibody comprises a $V_L$ sequence comprising, consisting of, or consisting essentially of SEQ ID NO: 287. In some aspects, the antibody comprises a $V_L$ sequence comprising, consisting of, or consisting essentially of SEQ ID NO: 288.

2.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure.

In some embodiments, the $V_L$ sequence comprises, consists of, or consists essentially of any of the illustrative $V_L$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.6.2. Excluded $V_L$ Sequences

In some embodiments, the $V_L$ sequences provided herein do not comprise certain $V_L$ sequences.

In some aspects, the $V_L$ sequence does not comprise, consist of, or consist essentially of a sequence selected from SEQ ID NOs: 289-293. In some aspects, the $V_L$ sequence does not comprise, consist of, or consist essentially of SEQ ID NO: 289. In some aspects, the $V_L$ sequence does not comprise, consist of, or consist essentially of SEQ ID NO: 290. In some aspects, the $V_L$ sequence does not comprise, consist of, or consist essentially of SEQ ID NO: 291. In some aspects, the $V_L$ sequence does not comprise, consist of, or consist essentially of SEQ ID NO: 292. In some aspects, the $V_L$ sequence does not comprise, consist of, or consist essentially of SEQ ID NO: 293.

2.7. Pairs 2.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of SEQ ID NOs: 113-131 and 309-315, and the CDR-L3 sequence is a CDR-L3 sequence comprising, consisting of, or consisting essentially of SEQ ID NOs: 200-218.

In some aspects, the CDR-H3 sequence is SEQ ID NO: 113, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 114, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 115, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 116, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 117, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 118, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 119, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 120, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 121, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 122, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 123, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 124, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 125, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 126, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 127, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 128, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 129, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 130, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 131, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 309, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 310, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 311, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 312, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 313, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 314, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

In some aspects, the CDR-H3 sequence is SEQ ID NO: 315, and the CDR-L3 sequence is selected from SEQ ID NOs: 200-218. In some aspects, the CDR-L3 sequence is SEQ ID NO: 200. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218.

2.7.1.1. Variants of CDR-H3-CDR-L3 Pairs

In some embodiments, the CDR-H3-CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.7.1.2. Excluded CDR-H3-CDR-L3 Pairs

In some embodiments, the CDR-H3-CDR-L3 pairs provided herein do not comprise certain CDR-H3-CDR-L3 pairs.

In some aspects, the CDR-H3 sequence is not selected from SEQ ID NOs: 108-112 or 132-136, and the CDR-L3 sequence is not selected from SEQ ID NOs: 195-199 or 219-223.

In some aspects, the CDR-H3 sequence is not SEQ ID NO: 108, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 109, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 110, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 111, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 112, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 132, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 133, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 134, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 135, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

In some aspects, the CDR-H3 sequence is not SEQ ID NO: 136, and the CDR-L3 sequence is not selected from SEQ ID NOs: 195-199 or 219-223. In some aspects, the CDR-L3 sequence is not SEQ ID NO: 195. In some aspects, the CDR-L3 sequence is not SEQ ID NO: 196. In some aspects, the CDR-L3 sequence is not SEQ ID NO: 197. In some aspects, the CDR-L3 sequence is not SEQ ID NO: 198. In some aspects, the CDR-L3 sequence is not SEQ ID NO: 199. In some aspects, the CDR-L3 sequence is not SEQ ID NO: 219. In some aspects, the CDR-L3 sequence is not SEQ ID NO: 220. In some aspects, the CDR-L3 sequence is not SEQ ID NO: 221. In some aspects, the CDR-L3 sequence is not SEQ ID NO: 222. In some aspects, the CDR-L3 sequence is not SEQ ID NO: 223.

2.7.2. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOs: 246-264 and 316-322, and the $V_L$ sequence is a $V_L$ sequence comprising, consisting of, or consisting essentially of SEQ ID NOs: 270-288.

In some aspects, the $V_H$ sequence is SEQ ID NO: 246, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 247, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 248, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 249, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 250, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 251, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 252, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 253, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 254, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 255 (with or without a serine prepended to the sequence), and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 256, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 257, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 258, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 259, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 260, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 261, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 262, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 263, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 264, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 316, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 317, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 318, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 319, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 320, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 321, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 322, and the $V_L$ sequence is selected from SEQ ID NOs: 270-288. In some aspects, the $V_L$ sequence is SEQ ID NO: 270. In some aspects, the $V_L$ sequence is SEQ ID NO: 271. In some aspects, the $V_L$ sequence is SEQ ID NO: 272. In some aspects, the $V_L$ sequence is SEQ ID NO: 273. In some aspects, the $V_L$ sequence is SEQ ID NO: 274. In some aspects, the $V_L$ sequence is SEQ ID NO: 275. In some aspects, the $V_L$ sequence is SEQ ID NO: 276. In some aspects, the $V_L$ sequence is SEQ ID NO: 277. In some aspects, the $V_L$ sequence is SEQ ID NO: 278. In some aspects, the $V_L$ sequence is SEQ ID NO: 279. In some aspects, the $V_L$ sequence is SEQ ID NO: 280. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

2.7.2.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure.

In some embodiments, the $V_H$ sequence comprises, consists of, or consists essentially of any of the illustrative $V_H$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure.

In some embodiments, the $V_L$ sequence comprises, consists of, or consists essentially of any of the illustrative $V_L$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7.2.2. Excluded $V_H$-$V_L$ Pairs

In some embodiments, the $V_H$-$V_L$ pairs provided herein do not comprise certain $V_H$-$V_L$ pairs.

In some aspects, the $V_H$ sequence is not selected from SEQ ID NOs: 265-269, and the $V_L$ sequence is not selected from SEQ ID NOs: 289-293.

In some aspects, the $V_H$ sequence is not SEQ ID NO: 265, and the $V_L$ sequence is not selected from SEQ ID NO: 289-293. In some aspects, the $V_L$ sequence is not SEQ ID NO: 289. In some aspects, the $V_L$ sequence is not SEQ ID NO: 290. In some aspects, the $V_L$ sequence is not SEQ ID NO: 291. In some aspects, the $V_L$ sequence is not SEQ ID NO: 292. In some aspects, the $V_L$ sequence is not SEQ ID NO: 293.

In some aspects, the $V_H$ sequence is not SEQ ID NO: 266, and the $V_L$ sequence is not selected from SEQ ID NO: 289-293. In some aspects, the $V_L$ sequence is not SEQ ID NO: 289. In some aspects, the $V_L$ sequence is not SEQ ID NO: 290. In some aspects, the $V_L$ sequence is not SEQ ID NO: 291. In some aspects, the $V_L$ sequence is not SEQ ID NO: 292. In some aspects, the $V_L$ sequence is not SEQ ID NO: 293.

In some aspects, the $V_H$ sequence is not SEQ ID NO: 267, and the $V_L$ sequence is not selected from SEQ ID NO: 289-293. In some aspects, the $V_L$ sequence is not SEQ ID NO: 289. In some aspects, the $V_L$ sequence is not SEQ ID NO: 290. In some aspects, the $V_L$ sequence is not SEQ ID NO: 291. In some aspects, the $V_L$ sequence is not SEQ ID NO: 292. In some aspects, the $V_L$ sequence is not SEQ ID NO: 293.

In some aspects, the $V_H$ sequence is not SEQ ID NO: 268, and the $V_L$ sequence is not selected from SEQ ID NO: 289-293. In some aspects, the $V_L$ sequence is not SEQ ID NO: 289. In some aspects, the $V_L$ sequence is not SEQ ID NO: 290. In some aspects, the $V_L$ sequence is not SEQ ID NO: 291. In some aspects, the $V_L$ sequence is not SEQ ID NO: 292. In some aspects, the $V_L$ sequence is not SEQ ID NO: 293.

In some aspects, the $V_H$ sequence is not SEQ ID NO: 269, and the $V_L$ sequence is not selected from SEQ ID NO: 289-293. In some aspects, the $V_L$ sequence is not SEQ ID NO: 289. In some aspects, the $V_L$ sequence is not SEQ ID NO: 290. In some aspects, the $V_L$ sequence is not SEQ ID NO: 291. In some aspects, the $V_L$ sequence is not SEQ ID NO: 292. In some aspects, the $V_L$ sequence is not SEQ ID NO: 293.

2.8. Consensus Sequences

In some embodiments, provided herein are anti-PD-1 antibodies comprising one or more sequences defined by consensus sequences. Each consensus sequence is based, at least in part, on one or more alignments of two or more useful anti-PD-1 CDR sequences provided in this disclosure. Based on such alignments, a person of skill in the art would recognize that different amino acid residues may useful in certain positions of the CDRs. Accordingly, each consensus sequence encompasses two or more useful anti-PD-1 CDR sequences.

2.8.1. CDR-H3 Consensus Sequences

In some embodiments, the antibody comprises a CDR-H3 sequence defined by the consensus sequence D-$\alpha_2$-$\alpha_3$-Y-$\alpha_5$-$\alpha_6$-G-S-G-Y, where $\alpha_2$ is A, V, or S; $\alpha_3$ is D or E; $\alpha_5$ is S or G; and $\alpha_6$ is S, L, or T. In some embodiments, $\alpha_5$ is S, G, or R. Sequencing of individual clones isolated from the output of the antibody selection process revealed that R occurred at nearly the same frequency as G.

In some aspects, if $\alpha_2$ is A, then $\alpha_3$ is not D; $\alpha_5$ is not S; or $\alpha_6$ is not S; or combinations thereof.

In some aspects, $\alpha_2$ is V or S; $\alpha_3$ is E; $\alpha_5$ is G; or $\alpha_6$ is L or T; or combinations thereof.

In some aspects, $\alpha_2$ is not A; $\alpha_3$ is not D; $\alpha_5$ is not S; or $\alpha_6$ is not S; or combinations thereof.

In some embodiments, the antibody comprises a CDR-H3 sequence defined by the consensus sequence $\beta_1$-G-Y-$\beta_4$-$\beta_5$-Y-$\beta_7$-$\beta_8$-F-$\beta_{10}$-$\beta_{11}$, where $\beta_1$ is not present or Q; $\beta_4$ is G or D; $\beta_5$ is N or V; $\beta_7$ is L or S; $\beta_8$ is Y or W; $\beta_{10}$ is D or A; and $\beta_{11}$ is V or Y.

2.8.2. Chothia CDR-H1 Consensus Sequences

In some embodiments, the antibody comprises a Chothia CDR-H1 sequence defined by the consensus sequence G-$\varepsilon_2$-$\varepsilon_3$-$\varepsilon_4$-$\varepsilon_5$-$\varepsilon_6$-$\varepsilon_7$, where $\varepsilon_2$ is Y or F; $\varepsilon_3$ is T, R or I; ß$_4$ is F or L; $\varepsilon_5$ is S, E, T, P, or R; $\varepsilon_6$ is T, S, H, Q, R, or W; and $\varepsilon_7$ is F, Y, or Q.

In some aspects, if $\varepsilon_5$ is T, then $\varepsilon_6$ is not S.

In some aspects, $\varepsilon_5$ is S, E, P, or R; or $\varepsilon_6$ is T, H, Q, R, or W; or combinations thereof.

In some aspects, $\varepsilon_2$ is not Y; $\varepsilon_3$ is not T or R; $\varepsilon_5$ is not T; $\varepsilon_6$ is not S; or $\varepsilon_7$ is not Y; or combinations thereof. 2.8.3. Kabat CDR-H2 Consensus Sequences In some embodiments, the antibody comprises a Kabat CDR-H2 sequence defined by the consensus sequence W-$\gamma_2$-S-A-$\gamma_5$-N-G-N-T-$\gamma_{10}$-Y-A-Q-K-L-Q-G, where $\gamma2$ is I or V; $\gamma5$ is Y or H; and $\gamma10$ is K or N.

In some aspects, $\gamma2$ is not I; $\gamma5$ is not Y; or $\gamma10$ is not N; or combinations thereof.

In some embodiments, the antibody comprises a Kabat CDR-H2 sequence defined by the consensus sequence $\delta_1$-I-S-G-$\delta_5$-G-$\delta_7$-$\delta_8$-T-Y-Y-$\delta_{12}$-D-S-V-$\delta_{16}$-G, where $\delta_1$ is T or A; $\delta_5$ is S or G; $\delta_7$ is S or G; $\delta_8$ is S, D or N; $\delta_{12}$ is A, P or S; and $\delta_{16}$ is K or Q.

In some aspects, if $\delta_1$ is A, then $\delta_5$ is not S; $\delta_7$ is not G; $\delta_8$ is not S; $\delta_{12}$ is not A; or $\delta_{16}$ is not K; or combinations thereof.

In some aspects, $\delta_1$ is T; $\delta_5$ is G; $\delta_7$ is S; $\delta_8$ is D or N; or $\delta_{12}$ is P or S; or combinations thereof.

In some aspects, $\delta_1$ is not A; $\delta_5$ is not S; $\delta_7$ is not G; $\delta_8$ is not S; $\delta_{12}$ is not A; or $\delta_{16}$ is not K; or combinations thereof.

2.8.4. Kabat CDR-H1 Consensus Sequences

In some embodiments, the antibody comprises a Kabat CDR-H1 sequence defined by the consensus sequence $\Theta_1$-$\Theta_2$-G-$\Theta_4$-S, where $\Theta_1$ is T, R, W, Q, H, or S; $\Theta_2$ is Y, F, or Q; and $\Theta_4$ is M or I.

In some aspects, $\Theta_1$ is T, R, W, Q, or H; $\Theta_2$ is F or Q; or $\Theta_4$ is M; or combinations thereof.

In some aspects, $\Theta_1$ is not S; $\Theta_2$ is not Y; or $\Theta_4$ is not I; or combinations thereof.

2.8.5. CDR-L3 Consensus Sequences

In some embodiments, the antibody comprises a CDR-L3 sequence defined by the consensus sequence Q-Q-$\pi_3$-$\pi_4$-$\pi_5$-$\pi_6$-P-$\pi_8$-T, where $\pi_3$ is N, S, or W; $\pi_4$ is Y, K, or I; $\pi_5$ is N, E, or S; $\pi_6$ is S, V, D, or T; and $\pi_8$ is Y or W.

In some aspects, if $\pi_4$ is Y, then $\pi_3$ is not S; $\pi_5$ is not S; $\pi_6$ is not T; or $\pi_8$ is not W; or combinations thereof.

In some aspects, $\pi_3$ is N or W; $\pi_4$ is K or I; $\pi_5$ is N or E; $\pi_6$ is S, V, or D; or $\pi_8$ is Y; or combinations thereof.

In some aspects, $\pi_3$ is not S; $\pi_4$ is not Y; $\pi_5$ is not S; $\pi_6$ is not T; or $\pi_8$ is not W; or combinations thereof.

2.8.6. CDR-L1 Consensus Sequences

In some embodiments, the antibody comprises a CDR-L1 sequence defined by the consensus sequence S-G-D-A-L-$\mu_6$-$\mu_7$-Q-Y-$\mu_{10}$-Y, where $\mu_6$ is P, T, or S; $\mu_7$ is M, T, E, or K; and $\mu_{10}$ is G or A.

In some aspects, if $\mu_6$ is P, then $\mu_7$ is not K, $\mu_{10}$ is not A, or combinations thereof.

In some aspects, $\mu_6$ is T or S; $\mu_7$ is M, T, or E; or $\mu_{10}$ is G; or combinations thereof.

In some aspects, $\mu_6$ is not P; $\mu_7$ is not K; or $\mu_{10}$ is not A; or combinations thereof.

In some embodiments, the antibody comprises a CDR-L1 sequence defined by the consensus sequence R-A-S-E-$\Sigma_5$-V-D-$\Sigma_8$-$\Sigma_9$-G-$\Sigma_{11}$-S-F-M-$\Sigma_{15}$, where $\Sigma_5$ is S or N; $\Sigma_8$ is N or D; $\Sigma_9$ is S or Y; $\Sigma_{11}$ is I or V; and $\Sigma_{15}$ is S or N.

3. Germline

In some embodiments, the antibody that specifically binds PD-1 is an antibody comprising a variable region that is encoded by a particular germline gene, or a variant thereof. The illustrative antibodies provided herein comprise variable regions that are encoded by the heavy chain variable region germline genes VH1-18, VH3-21, VH3-7, and VH3-15, or variants thereof; and the light chain variable region germline genes V$\lambda$3-25, V$\kappa$1-9, V$\kappa$3-11, V$\kappa$3-20, and V$\kappa$4-1, or variants thereof. One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the VH1 or VH3 family, or a variant thereof. In some embodiments, a CDR-L sequence provided herein may be combined with a variable region encoded by a variable region germline gene selected from the V$\lambda$3, V$\kappa$1, V$\kappa$3, and V$\kappa$4 families, or a variant thereof.

4. Affinity

In some embodiments, the affinity of the antibody for PD-1, as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-10}$ M. In some embodiments, the affinity of the antibody is between about $10^{-9}$ M and $10^{-11}$ M. In some embodiments, the affinity of the antibody is between about $10^{-10}$ M and $10^{-11}$ M.

In some embodiments, the affinity of the antibody for human PD-1 is between about $3.85 \times 10^{-8}$ M and $2.52 \times 10^{-10}$ M. In some embodiment, the affinity of the antibody for human PD-1 is about $2.55 \times 10^{-8}$ M, about $1.52 \times 10^{-8}$ M, about $9.52 \times 10^{-9}$ M, about $1.09 \times 10^{-8}$ M, about $4.50 \times 10^{-9}$ M, about $1.90 \times 10^{-9}$ M, about $4.76 \times 10^{-9}$ M, about $4.5 \times 10^{-9}$ M, about $1.04 \times 10^{-8}$ M, about $9.90 \times 10^{-9}$ M, about $9.13 \times 10^{-10}$ M, about $2.52 \times 10^{-10}$ M, about $2.58 \times 10^{-9}$ M, about $3.85 \times 10^{-8}$ M, about $3.66 \times 10^{-9}$ M, about $3.15 \times 10^{-9}$ M, about $5.14 \times 10^{-9}$ M, about $2.47 \times 10^{-9}$ M, about $2.79 \times 10^{-9}$ M, about $1.20 \times 10^{-9}$ M, or about $1.28 \times 10^{-8}$ M In some embodiments, the affinity of the antibody for human PD-1 expressed on the surface of a cell is between about 3.2 and about 0.2 nM. In some embodiment, the affinity of the antibody for human PD-1 expressed on the surface of a cell is about 0.2 nM, about 0.4 nM, about 0.9 nM, about 1 nM, about 0.3 nM, about 0.7 nM, about 0.2 nM, about 0.8 nM, about 3.2 nM, about 2.9 nM, about 1.39 nM, or about 1.34 nM.

In some embodiments, the affinity of the antibody for murine PD-1 is between about $6.09 \times 10^{-8}$ M and $9.08 \times 10^{-9}$ M. In some embodiment, the affinity of the antibody for murine PD-1 is about $6.09 \times 10^{-8}$ M, about $6.22 \times 10^{-8}$ M, or about $9.08 \times 10^{-9}$ M.

In some embodiments, the affinity of the antibody for cynomolgus PD-1 is between about $2.43 \times 10^{-8}$ M and $1.95 \times 10^{-10}$ M. In some embodiment, the affinity of the antibody for cynomolgus PD-1 is about $2.43 \times 10^{-8}$ M, about $1.55 \times 10^{-8}$ M, about $2.22 \times 10^{-8}$ M, about $2.56 \times 10^{-9}$ M, about $2.54 \times 10^{-9}$ M, about $5.61 \times 10^{-10}$ M, or about $1.95 \times 10^{-10}$ M.

In some embodiments the antibody has a $k_a$ of at least about $10^4$ M$^-$×sec$^{-1}$. In some embodiments the antibody has a $k_a$ of at least about $10^5$ M$^{-1}$×sec$^{-1}$. In some embodiments the antibody has a $k_a$ of at least about $10^6$ M$^{-1}$×sec$^{-1}$. In some embodiments the antibody has a $k_a$ of between about $10^4$ M$^{-1}$×sec$^{-1}$ and about $10^5$ M$^{-1}$×sec$^{-1}$. In some embodiments the antibody has a $k_a$ of between about $10^5$ M$^{-1}$×sec$^{-1}$ and about $10^6$ M$^{-1}$×sec$^{-1}$.

In some embodiments the antibody has a $k_a$ when associating with human PD-1 of between about $4.74 \times 10^4$ M$^1$×sec$^1$ and about $1.23 \times 10^6$ M$^1$×sec$^1$. In some embodiments the antibody has a $k_a$ when associating with human PD-1 of about $4.88 \times 10^5$ M$^{-1}$×sec$^{-1}$, about $1.23 \times 10^6$ M$^{-1}$×sec$^{-1}$, about $7.37 \times 10^5$ M$^{-1}$×sec$^{-1}$, about $6.87 \times 10^5$ M$^{-1}$×sec$^{-1}$, about $5.63 \times 10^5$ M$^{-1}$×sec$^{-1}$, about $5.16 \times 10^5$ M$^{-1}$×sec$^{-1}$, about $2.48 \times 10^5$ M$^{-1}$×sec$^{-1}$, about $7.98 \times 10^5$ M$^{-1}$×sec$^{-1}$, about $1.82 \times 10^5$ M$^{-1}$×sec$^{-1}$, about $4.74 \times 10^4$ M$^{-1}$×sec$^{-1}$, about $1.85 \times 10^5$ M$^1$×sec$^1$, about $2.00 \times 10^5$ M$^1$×sec$^1$, about $8.12 \times 10^4$ M$^1$×sec$^1$, about $1.21 \times 10^6$ M$^1$×sec$^1$, about $1.16 \times 10^6$ M$^{-1}$×sec$^{-1}$, about $5.13 \times 10^5$ M$^{-1}$×sec$^{-1}$, or about $1.86 \times 10^5$ M$^{-1}$×sec$^{-1}$.

In some embodiments the antibody has a $k_d$ of about $10^{-5}$ sec$^{-1}$ or less. In some embodiments the antibody has a $k_d$ of about $10^{-4}$ sec$^{-1}$ or less. In some embodiments the antibody has a $k_d$ of about $10^{-3}$ sec$^{-1}$ or less. In some embodiments the antibody has a $k_d$ of between about $10^{-2}$ sec$^{-1}$ and about $10^{-5}$ sec$^{-1}$. In some embodiments the antibody has a $k_d$ of between about $10^{-2}$ sec$^{-1}$ and about $10^{-4}$ sec$^{-1}$. In some embodiments the antibody has a $k_d$ of between about $10^{-3}$ sec$^{-1}$ and about $10^{-5}$ sec$^{-1}$.

In some embodiments the antibody has a $k_d$ when dissociating from human PD-1 of between about $1.87 \times 10^{-2}$ sec$^{-1}$ and about $4.17 \times 10^{-4}$ sec$^{-1}$. In some embodiments the antibody has a $k_d$ when dissociating from human PD-1 of about $1.24 \times 10^{-2}$ sec$^{-1}$, about $1.87 \times 10^{-2}$ sec$^{-1}$, about $7.01 \times 10^{-3}$ sec$^{-1}$, about $7.74 \times 10^{-3}$ sec$^{-1}$, about $2.54 \times 10^{-3}$ sec$^{-1}$, about $9.80 \times 10^{-4}$ sec$^{-1}$, about $1.18 \times 10^{-3}$ sec$^{-1}$, about $3.59 \times 10^{-3}$ sec$^{-1}$, about $4.68 \times 10^{-4}$ sec$^{-1}$, about $1.82 \times 10^{-3}$ sec$^{-1}$, about $6.79 \times 10^{-4}$ sec$^{-1}$, about $6.28 \times 10^{-4}$ sec$^{-1}$, about $4.17 \times 10^{-4}$ sec$^{-1}$, about $2.99 \times 10^{-3}$ sec$^{-1}$, about $3.24 \times 10^{-3}$ sec$^{-1}$, about $6.17 \times 10^{-4}$ sec$^{-1}$, or about $2.39 \times 10^{-3}$ sec$^{-1}$.

In some aspects, the $K_D$, $k_a$, and $k_d$ are determined at 25° C. In some embodiments, the $K_D$, $k_a$, and $k_d$ are determined by surface plasmon resonance. In some embodiments, the $K_D$, $k_a$, and $k_d$ are determined according to the methods described in Examples 4 and 6.

5. Inhibition of PD-L1 and PD-L2 Binding

In some embodiments, the antibody inhibits binding of one or more of PD-L1 and PD-L2 to PD-1.

In some embodiments, the antibody inhibits binding of PD-L1 to PD-1 with an IC$_{50}$ of about 1 to about 7 nM. In some aspects, the antibody inhibits binding of PD-L1 to PD-1 with an IC$_{50}$ of about 1.99, about 2.53, about 5.86, or about 5.96 nM.

In some embodiments, the antibody inhibits binding of PD-L2 to PD-1 with an IC$_{50}$ of about 0.01 to about 1 nM. In some aspects, the antibody inhibits binding of PD-L2 to PD-1 with an IC$_{50}$ of about 0.01, about 0.18, about 0.56, or about 0.58 nM.

In some aspects, the antibody inhibits binding of PD-L1 to PD-1 with an IC$_{50}$ of about 5.96 nM, and inhibits binding of PD-L2 to PD-1 with an IC$_{50}$ of about 0.56 nM. In some aspects, the antibody inhibits binding of PD-L1 to PD-1 with an IC$_{50}$ of about 5.86 nM, and inhibits binding of PD-L2 to PD-1 with an IC$_{50}$ of about 0.58 nM. In some aspects, the antibody inhibits binding of PD-L1 to PD-1 with an IC$_{50}$ of about 1.99 nM, and inhibits binding of PD-L2 to PD-1 with an IC$_{50}$ of about 0.01 nM. In some aspects, the antibody inhibits binding of PD-L1 to PD-1 with an IC$_{50}$ of about 2.53 nM, and inhibits binding of PD-L2 to PD-1 with an IC$_{50}$ of about 0.18 nM.

6. PD-1 Assays

In some embodiments, the anti-PD-1 antibodies induce the secretion of interferon gamma when added to a peripheral blood mononuclear cell (PBMC) two-way mixed lymphocyte reaction (MLR) assay, as described in Examples 8 and 16.

In some embodiments, the anti-PD-1 antibodies induce the secretion of interferon gamma when added to a PBMC cytomegalovirus recall assay, as described in Example 16.

In some embodiments, the anti-PD-1 antibodies accelerate the onset of graft versus host disease, as shown in Example 18.

7. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

8. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

An alteration in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.,* 1991, 9:457-492.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.,* 1986, 83:7059-7063; Hellstrom et al., *Proc. Natl. Acad. Sci. U.S.A.,* 1985, 82:1499-1502; and Bruggemann et al., *J. Exp. Med.,* 1987, 166:1351-1361. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.,* 1998, 95:652-656.

C1q binding assays may also be carried out to confirm that the antibody is unable to bind C1q and hence lacks CDC activity. Examples of C1q binding assays include those described in WO 2006/029879 and WO 2005/100402.

Complement activation assays include those described, for example, in Gazzano-Santoro et al., *J. Immunol. Methods,* 1996, 202:163-171; Cragg et al., *Blood,* 2003, 101: 1045-1052; and Cragg and Glennie, *Blood,* 2004, 103:2738-2743.

FcRn binding and in vivo clearance (half-life determination) can also be measured, for example, using the methods described in Petkova et al., *Intl. Immunol.,* 2006, 18:1759-1769.

9. Preparation of Antibodies

9.1. Antigen Preparation

The PD-1 antigen to be used for production of antibodies may be intact PD-1 or a fragment of PD-1. The intact PD-1, or fragment of PD-1, may be in the form of an isolated protein or expressed by a cell. Other forms of PD-1 useful for generating antibodies will be apparent to those skilled in the art.

9.2. Monoclonal Antibodies

Monoclonal antibodies may be obtained, for example, using the hybridoma method first described by Kohler et al., *Nature,* 1975, 256:495-497, and/or by recombinant DNA methods (see e.g., U.S. Pat. No. 4,816,567). Monoclonal antibodies may also be obtained, for example, using phage or yeast-based libraries. See e.g., U.S. Pat. Nos. 8,258,082 and 8,691,730.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3rd ed. (1986) Academic Press, San Diego, Calif.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.,* 1984, 133:3001.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

9.3. Humanized Antibodies

Humanized antibodies may be generated by replacing most, or all, of the structural portions of a monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature,* 1991, 349:293-299; Rader et al., *Proc. Nat. Acad. Sci. U.S.A.,* 1998, 95:8910-8915; Steinberger et al., *J. Biol. Chem.,* 2000, 275:36073-36078; Queen et al., *Proc. Natl. Acad. Sci. U.S.A.,* 1989, 86:10029-10033; and U.S. Pat. Nos. 5,585,089, 5,693,761, 5,693,762, and 6,180,370.

9.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.,* 1993, 90:2551; Jakobovits et al., *Nature,* 1993, 362:255-258; Bruggermann et al., *Year in Immuno.,* 1993, 7:33; and U.S. Pat. Nos. 5,591,669, 5,589,369 and 5,545,807. Human antibodies can also be derived from phage-display libraries (see e.g., Hoogenboom et al., *J. Mol. Biol.,* 1991, 227:381-388; Marks et al., *J. Mol. Biol.,* 1991, 222:581-597; and U.S. Pat. Nos. 5,565,332 and 5,573,905). Human antibodies may also be generated by in vitro activated B cells (see e.g., U.S. Pat. Nos. 5,567,610 and 5,229,275). Human antibodies may also be derived from yeast-based libraries (see e.g., U.S. Pat. No. 8,691,730).

10. Vectors, Host Cells, and Recombinant Methods

The invention also provides isolated nucleic acids encoding anti-PD-1 antibodies, vectors and host cells comprising the nucleic acids, and recombinant techniques for the production of the antibodies.

For recombinant production of the antibody, the nucleic acid encoding it may be isolated and inserted into a replicable vector for further cloning (i.e., amplification of the DNA) or expression. In some aspects, the nucleic acid may be produced by homologous recombination, for example as described in U.S. Pat. No. 5,204,244.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615.

Illustrative examples of suitable host cells are provided below. these host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter*, *Erwinia*, *Klebsiella*, *Proteus*, *Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-PD-1 antibody-encoding vectors. Saccharomyces cerevisiae, or common baker's yeast, is a commonly used lower eukaryotic host microorganism. However, a number of other genera, species, and strains are available and useful, such as *Schizosaccharomyces pombe*, *Kluyveromyces* (*K. lactis*, *K. fragilis*, *K bulgaricus K. wickeramii*, *K. waltii*, *K. drosophilarum*, *K. thermotolerans*, and *K. marxianus*), *Yarrowia*, *Pichia pastoris*, *Candida* (*C. albicans*), *Trichoderma reesia*, *Neurospora crassa*, *Schwanniomyces* (*S. occidentalis*), and filamentous fungi such as, for example *Penicillium*, *Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-PD-1 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469, or WO 90/03430 and WO 87/00195 may be used.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology*, 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 1983, 62:1-13). Protein G is useful for all mouse isotypes and for human γ3 (Guss et al., *EMBO J.*, 1986, 5:1567-1575).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

11. Pharmaceutical Compositions and Methods of Administration

Any of the antibodies provided herein can be provided in any appropriate pharmaceutical composition and be administered by any suitable route of administration. Suitable routes of administration include, but are not limited to, the inhalation, intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes. In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

Further encompassed herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

11.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art.

Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

11.2. Dosage and Unit Dosage Forms

In human therapeutics, the doctor will determine the posology which he considers most appropriate according to a preventive or curative treatment and according to the age, weight, condition and other factors specific to the subject to be treated.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

12. Therapeutic Applications

For therapeutic applications, the antibodies of the invention are administered to a mammal, generally a human, in a pharmaceutically acceptable dosage form such as those known in the art and those discussed above. For example, the antibodies of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies also are suitably administered by peritumoral, intralesional, or perilesional routes, to exert local as well as systemic therapeutic effects. The intraperitoneal route may be particularly useful, for example, in the treatment of ovarian tumors.

The antibodies provided herein may be useful for the treatment of any disease or condition involving PD-1, such as cancer, autoimmune disease, and infection.

Any suitable cancer may be treated with the antibodies provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

Any suitable autoimmune disease may be treated with the antibodies provided herein. Illustrative suitable autoimmune diseases, or diseases with an autoimmune component, include, for example, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, Celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis (GPA) (formerly called Wegener's Granulomatosis), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease (chronic), Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with Streptococcus), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, rimary sclerosing cholangitis, psoriasis, psoriatic arthritis, idiopathic pulmonary fibrosis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, ulcerative colitis, undifferentiated connective tissue disease (UCTD), uveitis, vasculitis, vesiculobullous dermatosis, vitiligo, and Wegener's granulomatosis (now termed Granulomatosis with Polyangiitis (GPA).

Any suitable infection may be treated with the antibodies provided herein. Illustrative suitable infections include, for example, hepatitis A virus, hepatitis B virus, hepatitis C virus (HCV), human immunodeficiency virus (HIV), and other viral infections.

13. Diagnostic Applications

In some embodiments, the antibodies provided herein are used in diagnostic applications. For example, an ant-PD-1 antibody may be useful in assays for PD-1 protein. In some aspects the antibody can be used to detect the expression of PD-1 in various cells and tissues. These assays may be useful, for example, evaluating cancer and autoimmune disease.

In some diagnostic applications, the antibody may be labeled with a detectable moiety. Suitable detectable moieties include, but are not limited to radioisotopes, fluorescent labels, and enzyme-substrate labels. In another embodiment of the invention, the anti-PD-1 antibody need not be labeled, and the presence thereof can be detected using a labeled antibody which specifically binds to the anti-PD-1 antibody.

14. Affinity Purification Reagents

The antibodies of the invention may be used as affinity purification agents. In this process, the antibodies may be immobilized on a solid phase such a resin or filter paper, using methods well known in the art. The immobilized antibody is contacted with a sample containing the PD-1 protein (or fragment thereof) to be purified, and thereafter the support is washed with a suitable solvent that will remove substantially all the material in the sample except the PD-1 protein, which is bound to the immobilized antibody. Finally, the support is washed with another suitable solvent, such as glycine buffer, pH 5.0, that will release the PD-1 protein from the antibody.

15. Kits

In some embodiments, an anti-PD-1 antibody provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-PD-1 antibody. In some embodiments, the anti-PD-1 antibody is provided in the form of a pharmaceutical composition.

EXAMPLES

Example 1: Generation and Primary Screening of Anti-PD-1 Antibodies

Antibody Fab or scFv libraries were constructed using a standard overlap extension PCR protocol with mutagenic primers targeting CDRs. See Heckman and Pease, *Nat. Protoc.*, 2007, 2:924-932, incorporated by reference in its entirety. Selections for novel antibodies were performed using standard ribosome display protocols. See Dreir and Plückthun, *Methods Mol. Biol.*, 2011, Clifton, N.J., 687:283-306, incorporated by reference in its entirety. Specifically, scFv-based selection formats were performed according to published protocols. See Hanes and Plückthun, *Proc. Natl. Acad. Sci. U.S.A.*, 1997, 94:4937-4942, incorporated by reference in its entirety. After multiple rounds of selection, the DNA from RT-PCR output was cloned into an optimized vector for cell-free expression using standard molecular biology techniques. See Yin et al., *mAbs*, 2012, 4:217-225, incorporated by reference in its entirety. All constructs were HIS- and FLAG-tagged to streamline purification and testing during screening.

Libraries of antibody variants isolated by the selections were transformed into *E. coli* and grown on agar plates with antibiotic (kanamycin). Individual colonies were picked and grown in liquid broth (TB+kanamycin), and used as a template for DNA amplification via rolling circle amplification (RCA). The variants were then expressed in a cell-free protein synthesis reaction as described in Zawada et al. (*Biotechnol. Bioeng.*, 2011, 108:1570-1578, incorporated by reference in its entirety).

Briefly, cell-free extracts were treated with 50 μM iodoacetamide for 30 minutes at room temperature (RT; 20° C.) and added to a premix containing cell-free reaction components (see Groff et al., *mAbs*, 2014, 6:671-678, incorporated by reference in its entirety) and 10% (v/v) RCA DNA template (approximately 10 μg/mL DNA) for variants of interest. Cell free reactions, at a final volume of 60 μL, were incubated at 30° C. for 12 h on a shaker at 650 rpm in 96-well plates. Four hundred to one-thousand-five-hundred colonies were screened, depending on the predicted diversity of the libraries used in the different selection campaigns. Following synthesis, each reaction was diluted 1:50 into PBST (PBS at pH 7.4 with 0.2% Tween–20+0.2% BSA) and the variants expressed in each reaction were tested for functional activity via ELISA-based binding to recombinant human PD-1 (ACROBiosystems, Inc., Catalog No. PD1-H5221 or SINO Biological Inc. Catalog No. 10377-H08H).

Standard ELISA-based methods were employed. Specifically, 384-well plates were coated with 2 μg/mL recombinant PD-1 diluted in bicarbonate buffer, and then blocked with BSA. Antibody variants of interest were allowed to bind to the PD-1-coated plates, and detected with secondary antibodies (e.g., HRP-conjugated anti-human Fc or anti-FLAG) and then detected with chemiluminescent substrate (Pierce ELISA SuperSignal™ Substrate). Plates were analyzed on a Molecular Devices SpectraMax® M5 plate reader. Top hits were selected based on ELISA signal or signal/noise ratio and sequenced. Based on functional activity and sequence analysis, a subset of variants was selected for further scale-up and characterization.

Example 2: Secondary Screening of Antibody Variants

The top leads from the initial round of screening were cultured and plasmids encoding the antibody genes of interest were isolated using a QIAprep 96 Turbo® Miniprep Kit (Qiagen) according to the manufacturer's instructions. DNA was added to 4 mL of cell-free reaction medium to achieve a final concentration of 10 μg/mL. The cell-free reaction medium was then incubated overnight for 12 hr at 30° C., at 650 rpm.

The expressed variants from clarified cell-free reactions were purified via immobilized metal ion affinity chromatography (IMAC) using a semi-automated high throughput batch purification method. Briefly, purifications were performed in a 96-well plate format where 50 μL/well of IMAC resin (Ni Sepharose® High Performance, GE Healthcare) was equilibrated in IMAC binding buffer (50 mM Tris pH 8.0, 300 mM NaCl, 10 mM imidazole), incubated with 1 mL cell-free reaction for 15 minutes, followed by two washes in IMAC binding buffer. His-tagged antibody variants were then eluted using 200 μL IMAC elution buffer (50 mM Tris pH 8.0, 300 mM NaCl, 500 mM imidazole), and buffer exchanged into PBS using a 96-well Zeba™ plate (7 kDa MWCO, Thermo Fisher). Purified antibodies were quantified via high throughput capillary electrophoresis using the LabChip GXII® (Perkin Elmer) against a trastuzumab standard curve, according to the manufacturer's instructions.

Example 3: Hybridoma Generation

Balb/C mice were immunized with the extracellular domain of human PD-1 fused with human Fc (R&D Systems, supra) using standard immunization methods. The spleens and/or lymph nodes of the mice were harvested and fused with P3X cells to generate the hybridomas (Aragen Biosciences, Morgan Hill, Calif.), similar to what has been previously described. See Chronopoulou et al., *Methods Mol. Biol.*, 2014, 1131:47-70; and Kim et al., *Methods Mol. Biol.*, 2014, 1131:33-45, each of which is incorporated by reference in its entirety.

Total RNA was extracted from hybridoma cells using an RNeasy® Mini Kit (Qiagen) and converted to cDNA using a SMARTer™ RACE cDNA Amplification Kit (Clontech). Positive clones were identified by gel electrophoresis, cloned using a TOPO® kit (Invitrogen), and sequenced using standard Sanger methods.

Mouse single-chain antibodies were constructed by using total gene synthesis using codons optimized for *E. coli*. The genes encoding the antibodies were cloned into a standard cell-free expression vector. See Yin et al., *mAbs*, 2012, 4:217-225, incorporated by reference in its entirety.

The CDRs from m1E9 were grafted onto human antibody frameworks VH3-21, VH3-7, Vκ1-9, and Vκ3-11 by standard methodology to yield humanized antibodies h1E9-1, h1E9-2, h1E9-4, and h1E9-5. See Kuramochi et al., *Methods Mole. Biol.*, 2014, 1060:123-137, incorporated by reference in its entirety. The same method was used to graft the CDRs from m4B10 onto human antibody frameworks VH3-15, Vκ3-11, Vκ3-20, and Vκ4-1 to yield humanized antibodies h4B10-1, h4B10-2, and h4B10-3.

Example 4: Kinetic Analysis of Selected Antibody Variants

Human PD-1 (ACROBiosystems, Inc., Catalog No. PD1-H5221), cynomolgus PD-1 (ACROBiosystems, Inc., Catalog No. PD1-H5254), and murine PD-1 (R&D Systems Inc., Catalog No. 1021-PD-100) were used, as indicated, for kinetic analysis.

Monoclonal anti-FLAG M2 IgG (Sigma-Aldrich # F9291) was immobilized onto a CMS chip (GE Life Sciences) using amine coupling chemistry (from Amine Coupling Kit, GE Life Sciences). The immobilization steps were carried out at a flow rate of 25 µl/min in 1×HBS-EP+ buffer (GE Life Sciences; 10× Stock diluted before use). The sensor surfaces were activated for 7 min with a mixture of NHS (0.05 M) and EDC (0.2 M). The Anti-FLAG M2 IgG was injected over all 4 flow cells at a concentration of 25 µg/ml in 10 mM sodium acetate, pH 4.5, for 7 min. Ethanolamine (1 M, pH 8.5) was injected for 7 min to block any remaining activated groups. An average of 12,000 response units (RU) of capture antibody was immobilized on each flow cell.

Off-rate and kinetic binding experiments were performed at 25° C. using 1× HBS-EP+ buffer. Test and control antibodies were injected over the Anti-FLAG surface at concentrations of 5-10 µg/mL for 12 seconds at a flow rate of 10 µl/min on flow cells 2, 3 and 4, followed by a buffer wash for 30 seconds at the same flow rate. Kinetic characterization of antibody samples was carried out with a single concentration of antigen (for off-rate ranking) or a 1:2 dilution series of antigen (for kinetic characterization) and 1 injection of 0 nM antigen (i.e., buffer alone). After capturing ligand (anti-PD-1 antibody) on the anti-FLAG surface, the analyte (huPD1-His) was bound at 50, 25, 12.5, 6.25 and 0 nM for 180 seconds, followed by a 600 second dissociation phase at a flow rate of 50 µl/min. Between each ligand capture and analyte binding cycle, regeneration was carried out using 2 injections of 10 mM glycine pH 2.0 for 30 seconds at 30 µL/min, followed by a 30 second buffer wash step.

The data was fit with the Biacore T200 Evaluation software, using a 1:1 Langmuir binding model. $K_D$ (affinity, nM) was determined as a ratio of the kinetic rate constants calculated from the fits of the association and dissociation phases.

Example 5: PD-1-PD-L1 Competition ELISA

Anti-PD1 antibodies were tested for their ability to block a PD-1/PD-L1 interaction. PD-1 (ACROBiosystems, Inc.) was adsorbed on 384-well white Maxisorp® plates (Nunc) at 2 µg/mL in sodium bicarbonate buffer (pH 8.9) and incubated at 30° C. for 1 hour or overnight at 4° C. The plate was washed 3 times with PBS pH 7.4 with 0.05% Tween20 and blocked with 2% bovine serum albumin (BSA) in PBS pH 7.4+0.1% Tween20 for 1 hour at 30° C.

The blocking solution was aspirated, and a dilution series of antibody was mixed with 100 nM PD-L1-Fc (ACROBiosystems, Inc.) in 0.2% BSA in PBS pH 7.4+0.1% Tween20 (diluent buffer) and incubated at 30° C. for 1 hour. The plate was washed, and 10 nM anti-PD-L1 antibody (BioLegend, clone 29E.2A3) in diluent buffer was added to all wells. After a 1 hour incubation at 30° C., the plate was washed and incubated with HRP-conjugated anti-mouse Fc (Jackson Laboratories), followed by detection with SuperSignal™ Pico Chemiluminescent Substrate (Thermo Pierce). Luminescence was detected on a SpectraMax® M5 plate reader (Molecular Devices).

Example 6: Cell Binding Experiments

Antibodies with expression levels >250 nM and mouse IgGs from hybridomas were tested in a fluorescence-activated cell sorting (FACS) cell-binding assay. Chinese Hamster Ovary (or CHO) Cells stably expressing the human target molecule PD-1 on the cell surface (CHO-PD1) were used to screen for binding. Parental CHO cells were used as a negative control to determine background-binding levels. Parental CHO cells and CHO-PD1 cells were cultured in RPMI w/10% FCS penicillin/streptomycin (Pen/Strep) and glutamine (or Gln) and split every 3-4 days at $10^5$ cells/mL.

A mix of parental CHO cells and CHO-PD1 cells was prepared as follows: Parental CHO cells were washed 2× in PBS then incubated in PBS containing 1 µM CellTrace™ Oregon Green488® (Life Technologies) at 37° C. for 30 minutes. Cells were then washed 2× with RPMI w/10% fetal calf serum (FCS), washed 2× with FACS buffer (PBS w/2% FCS), suspended thoroughly in ice-cold FACS buffer at a final concentration of $2\times10^6$ cells/mL and kept on ice. CHO-PD1 cells were similarly washed with FACS buffer and kept on ice at $2\times10^6$ cells/mL. Parental CHO cells and CHO-PD1 cells were then mixed to obtain a 1:1 cell suspension and seeded at 100 µL per well on 96 well polypropylene plates. Plates were spun at 1500 rpm for 5 minutes and cell pellets were suspended in 50 µL FACS buffer containing 6-12 point dilutions of anti-PD-1 variants starting from concentrations of ~100-200 nM antibody, dispensed using BioMek FX (Beckman Coulter). Cells were then incubated on ice for 1 hr, washed with FACS buffer and incubated for 1 hr on ice with 50 µL FACS buffer containing 2.5 µg/ml R-phycoerythrin-conjugated goat anti-Human IgG (Jackson ImmunoResearch) or AF647-conjugated goat anti-mouse IgG (Life Technologies) dispensed using BioMek FX (Beckman Coulter). Cells were then washed 2× with FACS buffer and fixed for 10 minutes in 200 µL PBS with 2% paraformaldehyde (PFA) prior to fluorescence detection. Samples were acquired using a Becton Dickinson LSRII FACS. Mean Fluorescence Intensity of PD-1 antibody binding was analyzed using FlowJo® software (Tree Star, Inc.).

Example 7: Cell-Based Ligand Competition Experiments

Variants that showed cell-binding activity were tested in a fluorescence-activated cell sorting (FACS) cell-based competition assay. CHO cells stably expressing the human target molecule PD-1 on the cell surface (CHO-PD1) were used to screen for antibodies that compete with hFc-tagged recombinant human PD-L1 or PD-L2 proteins (R&D systems) for binding to PD-L1 expressed on the cell surface.

CHO-PD1 cells were cultured in RPMI with 10% FCS Pen/Strep and Gln and split every 3-4 days at $10^5$ cells/ml. Cells were washed 2× with FACS buffer (PBS w/2% FCS), thoroughly in ice-cold FACS buffer at a final concentration of $1×10^6$ cells/ml and seeded at 100 μL per well on 96 well polypropylene plates. Plates were spun at 1500 rpm for 5 minutes and cell pellets were suspended in 50 μL FACS buffer containing 8 point 1:3 dilutions (2× concentrated) of anti-PD-1 antibody variants, starting from high concentration of ~200 nM. 50 μL FACS buffer containing a fixed amount of either 6 μg/ml rhPDL2-Fc or 50 μg/ml rhPDL1-Fc proteins were then added to the cells. Cell were then incubated on ice for 1 hr, washed with FACS buffer and incubated for 1 hr on ice with 50 μl FACS buffer containing 2.5 μg/ml R-phycoerythrin-conjugated anti-human IgG (Jackson ImmunoResearch). Cells were then washed 2× with FACS buffer and fixed for 10 minutes in 200 μl PBS with 2% PFA prior to acquisition. Samples were acquired using a Becton Dickinson LSRII FACS. Mean Fluorescence Intensity of rhPDL1 or rhPDL2 protein binding was analyzed using FlowJo® software (Tree Star, Inc.).

Example 8: Evaluating the Effect of Anti-PD-1 Antibodies on Interferon Gamma Production in a Mixed Lymphocyte Reaction Anti-PD-1 antibodies were functionally tested for potency in blocking the PD-1 pathway in a peripheral blood mononuclear cell (PBMC) two-way mixed lymphocyte reaction (MLR) assay by measuring interferon gamma (IFN-g) secretion in cell culture medium. $1×10^5$ human PBMC from 2 allogeneic donors were co-cultured in RPMI media+10% FBS in a total volume of 150 μl in a 96-well U-bottom plate. Anti-PD-1 antibodies were added at specific concentrations to each well. Isotype control antibody, non-PD-1 targeting antibody, or nothing were used as a negative controls. Cells were cultured for 5 days at 37° C. At day 5, conditioned media was collected and levels of IFN-g were measured using DuoSet® ELISA kits (R&D Systems).

Example 9: Characteristics of Antibodies Isolated from Primary and Secondary Screen Table 1 shows the characteristics of scFv-Fc antibodies (VH1-18Vλ3-25) isolated as described in Examples 1-2, and characterized as described above.

TABLE 1

Characteristics of antibodies isolated as described in Examples 1-2, and characterized as described above.

| Clone ID | $k_a$ (1/Ms) Human PD-1 | $k_d$ (1/s) Human PD-1 | $K_D$ (M) Human PD-1 | PD-L1 Competition | Cell Binding, $K_D$ (nM) Human PD-1 | Murine PD-1 Binding, $K_D$ (M) | Cynomolgus PD-1 Binding, $K_D$ (M) | MLR Activity (IFNg release) |
|---|---|---|---|---|---|---|---|---|
| 1353-A09 (SEQ ID NO: 238) | 4.88E+05 | 1.24E-02 | 2.55E-08 | yes, ++ | 0.2 | Not tested | Not tested | Not tested |
| 1353-C07 (SEQ ID NO: 239) | 1.23E+06 | 1.87E-02 | 1.52E-08 | yes | 0.4 | Not tested | Not tested | Not tested |
| 1353-E07 (SEQ ID NO: 240) | 7.37E+05 | 7.01E-03 | 9.52E-09 | yes | 0.9 | Not tested | Not tested | Not tested |
| 1353-F09 (SEQ ID NO: 241) | 6.87E+05 | 7.47E-03 | 1.09E-08 | yes | 1 | Not tested | Not tested | Not tested |
| 1353-G08 (SEQ ID NO: 242) | 5.63E+05 | 2.54E-03 | 4.50E-09 | yes, +++ | 0.3 | 6.09E-08 | 2.43E-08 | Not tested |
| 1353-G10 (SEQ ID NO: 243) | 5.16E+05 | 9.80E-04 | 1.90E-09 | yes, ++ | 0.7 | 6.22E-08 | 1.55E-08 | positive |
| 1353-H08 (SEQ ID NO: 244) | 2.48E+05 | 1.18E-03 | 4.76E-09 | yes, +++ | 0.2 | Not tested | Not tested | Not tested |
| 1353-H09 (SEQ ID NO: 245) | 7.98E+05 | 3.59E-03 | 4.50E-09 | yes, ++ | 0.8 | 9.08E-09 | 2.22E-08 | positive |

Example 10: Characteristics of Murine Hybridoma Antibodies

Table 2 shows the characteristics of IgG antibodies isolated as described in Example 3, and characterized as described above.

TABLE 2

Characteristics of murine hybridoma antibodies, characterized as described above.

| Clone ID | EC50[1] (nM) | IC50[2] (nM) | Cell Binding, $K_D$[3] (nM) | PD-L1 Competition, $IC_{50}$[4] (nM) | PD-L2 Competition, $IC_{50}$[4] (nM) | Biacore Human PD1 $K_D$ (M) | Biacore Cynomolgus $K_D$ (M) | MLR, IFNg secretion |
|---|---|---|---|---|---|---|---|---|
| 1B10 VH: SEQ ID NO: 255, with serine prepended to the sequence VL: SEQ ID NO: 279 | 1.71 | 9.47 | 3.2 | 5.96 | 0.56 | 1.04E-08 | 2.56E-09 | positive |

TABLE 2-continued

Characteristics of murine hybridoma antibodies, characterized as described above.

| Clone ID | EC50[1] (nM) | IC50[2] (nM) | Cell Binding, $K_D$[3] (nM) | PD-L1 Competition, $IC_{50}$[4] (nM) | PD-L2 Competition, $IC_{50}$[4] (nM) | Biacore Human PD1 $K_D$ (M) | Biacore Cynomolgus $K_D$ (M) | MLR, IFNg secretion |
|---|---|---|---|---|---|---|---|---|
| 1E9 VH: SEQ ID NO: 256 VL: SEQ ID NO: 280 | 0.33 | 0.89 | 2.9 | 5.86 | 0.58 | 9.90E−09 | 2.54E−09 | positive |
| 4B10 VH: SEQ ID NO: 257 VL: SEQ ID NO: 281 | 0.47 | 1.43 | 1.39 | 1.99 | 0.01 | 9.13E−10 | 5.61E−10 | positive |
| 10B4 VH: SEQ ID NO: 258 VL: SEQ ID NO: 282 | 0.59 | 1.32 | 1.34 | 2.53 | 0.18 | 2.52E−10 | 1.95E−10 | positive |

[1]Binding of human PD-1 (ACROBiosystems, Inc., Cat. No. PD1-H5221) via ELISA.
[2]Competition against PD-L1 (ACROBiosystems, Inc., Cat No. PD1-H5258) via ELISA.
[3]CHO cell line overexpressing human PD-1.
[4]Cell-based competition, i.e., Inhibition of PD-L1 or PD-L2 binding to CHO cells overexpressing human PD-1 is inhibited by IgG.

Example 11: Characteristics of Humanized Antibodies

Table 3 shows the characteristics of humanized scFv antibodies derived from the murine hybridoma antibodies of Example 10, and characterized as described above.

TABLE 3

Characteristics of humanized antibodies, characterized as described above.

| Clone | $k_a$ (1/Ms) Human PD-1 | $k_d$ (1/s) Human PD-1 | $K_D$ (M) Human PD-1 |
|---|---|---|---|
| h1E9-1 (VH3-21-Vκ1-9) scFv (SEQ ID NO: 227) | 1.82E+05 | 4.68E−04 | 2.58E−09 |
| h1E9-2 (VH3-21-Vκ3-11) scFv (SEQ ID NO: 228) | 4.74E+04 | 1.82E−03 | 3.85E−08 |
| h1E9-4 (VH3-7-Vκ1-9) scFv (SEQ ID NO: 229) | 1.85E+05 | 6.79E−04 | 3.66E−09 |
| h1E9-5 (VH3-7-Vκ3-11) scFv (SEQ ID NO: 230) | 2.00E+05 | 6.28E−04 | 3.15E−09 |
| m4B10 scFv (SEQ ID NO: 237) | 8.12E+04 | 4.17E−04 | 5.14E−09 |
| h4B10-1 (VH3-15-Vκ3-11) scFv (SEQ ID NO: 231) | 1.21E+06 | 2.99E−03 | 2.47E−09 |
| h4B10-2 (VH3-15-Vκ3-20) scFv (SEQ ID NO: 232) | 1.16E+06 | 3.24E−03 | 2.79E−09 |
| h4B10-3 (VH3-15-Vκ4-1) scFv (SEQ ID NO: 233) | 5.13E+05 | 6.17E−04 | 1.20E−09 |
| m1B10 scFv (SEQ ID NO: 235) | 1.86E+05 | 2.39E−03 | 1.28E−08 |

Example 12: Thermal Stability Data

Table 4 provides thermal stability of selected antibodies, as determined by differential scanning fluorimetry (DSF).

TABLE 4

Thermal stability of selected antibodies, as determined by DSF.

| Variant ID | Target | Scaffold | Tm1 (° C.) | Tm2 (° C.) |
|---|---|---|---|---|
| 1353-G12 | PD1 | scFv-Fc | 48.2 | |
| 1353-G08 | PD1 | scFv-Fc | 45.3 | |
| 1353-G10 | PD1 | scFv-Fc | 48.6 | |
| 1353-H09 | PD1 | scFv-Fc | 49.4 | |
| m1B10 | PD1 | scFv | 55.3 | |
| h1E9-1 | PD1 | scFv | 52.5 | |
| h1E9-2 | PD1 | scFv | 50.9 | |
| h1E9-4 | PD1 | scFv | 55.2 | |
| h1E9-5 | PD1 | scFv | 51.7 | |
| h4b10-1 | PD1 | scFv | 45.5 | 59.4 |
| h4b10-2 | PD1 | scFv | 45 | 61.7 |
| h4b10-3 | PD1 | scFv | 52.1 | 59.3 |

Example 13: Construction and Evaluation of h1E9-4 and h1E9-5 IgGs

Variable domains from h1E9-4 scFv ($V_H$: SEQ ID NO: 260; $V_L$: SEQ ID NO: 284), and h1E9-5 scFv ($V_H$: SEQ ID NO: 261; $V_L$: SEQ ID NO: 285) were grafted onto human antibody constant domains to generate human IgG1 antibodies based on these scFvs.

Specifically, the $V_H$ sequences were grafted onto $C_{H1}$—$C_{H2}$—$C_{H3}$ constant domains to yield full-length IgG HCs with C-terminal FlagHis tags (GSGDYKDDDDKGSGHH-HHHH; SEQ ID NO: 294) for ease of purification and assay development. The $V_L$ sequences were grafted onto $C_L$ domains to yield full-length IgG LCs. The sequence for both the h1E9-4 and h1E9-5 HCs, with C-terminal FlagHis tag, is provided in SEQ ID NO: 302. The sequence for the h1E9-4 LC is provided in SEQ ID NO: 304. The sequence for the h1E9-5 LC is provided in SEQ ID NO: 303.

The IgGs were expressed in a cell-free reaction, as described in Example 1, and purified using the FlagHis tags. The affinity of the IgGs for PD-1 was measured by surface plasmon resonance (Biacore®) and determined to be essentially equivalent to that of the parent scFvs. Affinity data is provided in Table 5.

TABLE 5

Affinity of h1E9-4 and h1E9-5 IgGs for PD-1 antigen.

| Sample | Ligand | $k_a$ (1/Ms) | $k_d$ (1/s) | $K_D$ (M) |
|---|---|---|---|---|
| PD-1-his | h1E9-4 IgG | 3.56E+04 | 4.42E-04 | 1.24E-08 |
| PD-1-his | h1E9-5 IgG | 2.43E+04 | 4.71E-04 | 1.94E-08 |

Example 14: Construction and Evaluation of h1E9 Humanized IgGs

The CDRs for m1E9 were grafted onto human antibody frameworks VH3-23, VH3-30, Vk4-1, Vk3-20, Vk2-28, and Vk1-33 by standard methodology (T. Kuramochi, T. Igawa, H. Tsunoda, and K. Hattori, Method in Molecular Biology, Human Monoclonal Antibodies: Methods and Protocols, 1060, 123-137) to yield humanized antibodies h1E9-HC1, h1E9-HC2, h1E9-HC3, h1E9-LC1, h1E9-LC2, h1E9-LC3, and h1E9-LC4. The HC constructs included C-terminal FlagHis tags (GSGDYKDDDDKGSGHHHHHH; SEQ ID NO: 294) for ease of purification and assay development. The resulting h1E9 heavy chains were: h1E9-HC3 (SEQ ID NO:324), h1E9-HC2 (SEQ ID NO:325), and h1E9-HC3 (SEQ ID NO:326). The resulting light chains were: h1E9-LC4 (SEQ ID NO:327), h1E9-LC3 (SEQ ID NO:328), h1E9-LC2 (SEQ ID NO:329), and h1E9-LC1 (SEQ ID NO:330).

The humanized heavy chains h1E9-HC1, h1E9-HC2, h1E9-HC3, and h1E9-5 were paired with humanized IgG light chains h1E9-LC1, h1E9-LC2, h1E9-LC3, and h1E9-LC4. These 16 combinations were then assessed for binding to human PD1 in vitro by surface plasmon resonance (Biacore®) and subsequently human and cynomolgus PD1 binding on CHO cells using FACS as described below.

Surface plasmon resonance (Biacore®) data is provided in Table 6.

TABLE 6

Affinity of h1E9 humanized IgGs for PD-1 antigen.

| Sample | Ligand | SEQ ID NOS | | $K_D$ (M) |
|---|---|---|---|---|
| PD-1-his | h1E9-HC1 × h1E9-LC1 | 326 | 330 | 5.08E-09 |
| PD-1-his | h1E9-HC1 × h1E9-LC2 | 326 | 329 | 1.90E-08 |
| PD-1-his | h1E9-HC1 × h1E9-LC3 | 326 | 328 | 6.38E-09 |
| PD-1-his | h1E9-HC1 × h1E9-LC4 | 326 | 327 | 6.33E-09 |
| PD-1-his | h1E9-HC2 × h1E9-LC1 | 325 | 330 | 3.11E-09 |
| PD-1-his | h1E9-HC2 × h1E9-LC2 | 325 | 329 | 1.23E-08 |
| PD-1-his | h1E9-HC2 × h1E9-LC3 | 325 | 328 | 1.09E-08 |
| PD-1-his | h1E9-HC2 × h1E9-LC4 | 325 | 327 | 4.96E-09 |
| PD-1-his | h1E9-HC3 × h1E9-LC1 | 324 | 330 | 3.60E-09 |
| PD-1-his | h1E9-HC3 × h1E9-LC2 | 324 | 329 | 3.19E-09 |
| PD-1-his | h1E9-HC3 × h1E9-LC3 | 324 | 328 | 1.69E-08 |
| PD-1-his | h1E9-HC3 × h1E9-LC4 | 324 | 327 | 9.40E-09 |
| PD-1-his | h1E9-5-IgG-HC-FLAG-HIS × h1E9-LC1 | 261 | 330 | 3.70E-09 |
| PD-1-his | h1E9-5-IgG-HC-FLAG-HIS × h1E9-LC2 | 261 | 329 | 1.62E-08 |
| PD-1-his | h1E9-5-IgG-HC-FLAG-HIS × h1E9-LC3 | 261 | 328 | 1.63E-08 |
| PD-1-his | h1E9-5-IgG-HC-FLAG-HIS × h1E9-LC4 | 261 | 327 | 7.31E-09 |

The affinity of the IgGs for cell-surface expressed human PD-1 were measured according to Example 6, above. Affinity data is provided in Table 7.

TABLE 7

Affinity of h1E9 humanized IgGs for Cell-Surface Human PD-1 antigen (nM).

| | | h1E9-HC1 SEQ ID NO: 326 | h1E9-HC2 SEQ ID NO: 325 | h1E9-HC3 SEQ ID NO: 324 | h1E9-5 HC SEQ ID NO: 261 |
|---|---|---|---|---|---|
| h1E9-LC1 | SEQ ID NO: 330 | 6 | 7 | 8 | 9 |
| h1E9-LC2 | SEQ ID NO: 329 | 12 | 11 | 19 | 16 |
| h1E9-LC3 | SEQ ID NO: 328 | 12 | 9 | 12 | 11 |
| h1E9-LC4 | SEQ ID NO: 327 | 8 | 4 | 9 | 14 |

The affinity of the IgGs for cell-surface expressed cynomolgus PD-1 were measured according to Example 6, above. Affinity data is provided in Table 8.

TABLE 8

Affinity of h1E9 humanized IgGs for Cell-Surface Cynomolgus PD-1 antigen (nM).

| | | h1E9-HC1 SEQ ID NO: 326 | h1E9-HC2 SEQ ID NO: 325 | h1E9-HC3 SEQ ID NO: 324 | h1E9-5 HC SEQ ID NO: 261 |
|---|---|---|---|---|---|
| h1E9-LC1 | SEQ ID NO: 330 | 7 | 6 | 4 | 4 |
| h1E9-LC2 | SEQ ID NO: 329 | 19 | 9 | 11 | 11 |
| h1E9-LC3 | SEQ ID NO: 328 | 15 | 9 | 8 | 9 |
| h1E9-LC4 | SEQ ID NO: 327 | 11 | 6 | 5 | 12 |

Example 15: In Vivo Efficacy of Anti-PD-1 Antibodies on Tumor Establishment and Growth MC38 colorectal cancer cells (2×10$^6$ cells in 0.1 mL PBS) were implanted subcutaneously on the right flank of C57BL/6 mice (Charles River Laboratories). On day 2 post-cell implantation (day 0), mice were treated with anti-PD-1 or control antibody at a dose of 5 mg/kg intraperitoneally. Animals were dosed on dosing days 0, 4, 8, 11, and 14.

The treatment groups were as follows:
(1) PBS vehicle;
(2) control rat IgG2a, clone 2A3;
(3) anti-PD-1 rat IgG2a, clone RMP1-14;
(4) anti-PD-1 human scFv-Fc, clone PD1-F2 (see SEQ ID NOs: 306 and 293 for $V_H$ and $V_L$ sequences, respectively, and SEQ ID NO: 305 for the scFv-Fc);
(5) anti-PD-1 human scFv-Fc, clone 1353-G08 (see SEQ ID NOs: 251 and 275 for $V_H$ and $V_L$ sequences, respectively, and SEQ ID NO: 242 for the scFv-Fc);
(6) anti-PD-1 human scFv-Fc, clone 1353-G10 (see SEQ ID NOs: 252 and 276 for $V_H$ and $V_L$ sequences, respectively, and SEQ ID NO: 243 for the scFv-Fc); and
(7) anti-PD-1 human IgG, clone PD1-F2v (see SEQ ID NOs: 603 and 293 for $V_H$ and $V_L$ sequences, respectively, SEQ ID NO: 307 for the HC sequence, and SEQ ID NO: 308 for the LC sequence).

Antibodies (2) and (3) were obtained commercially from Bio X Cell. Antibodies (4)-(6) were produced using the cell-free expression methods described in Example 1. Antibody 7 was produced by mammalian cell expression using HEK293 cells and standard techniques.

Tumors were measured using an electronic caliper and tumor volumes were calculated using the formula, volume=(width$^2$×length)/2. Statistical analysis was performed via a two-tailed Mann-Whitney test at day 17 post-treatment.

At day 17 post-treatment, all anti-PD-1 antibodies with strong mouse PD-1 reactivity (i.e., antibodies RMP1-14, PD1-F2, and 1353-G08) resulted in a significant delay in tumor establishment and growth (p<0.01) compared to the PBS and control rat IgG2a treatment groups. In contrast, antibody 1353-G10, which binds human PD-1 but has weaker reactivity with mouse PD-1, showed no significant effect on tumor establishment and growth (p>0.05).

Figure 2:
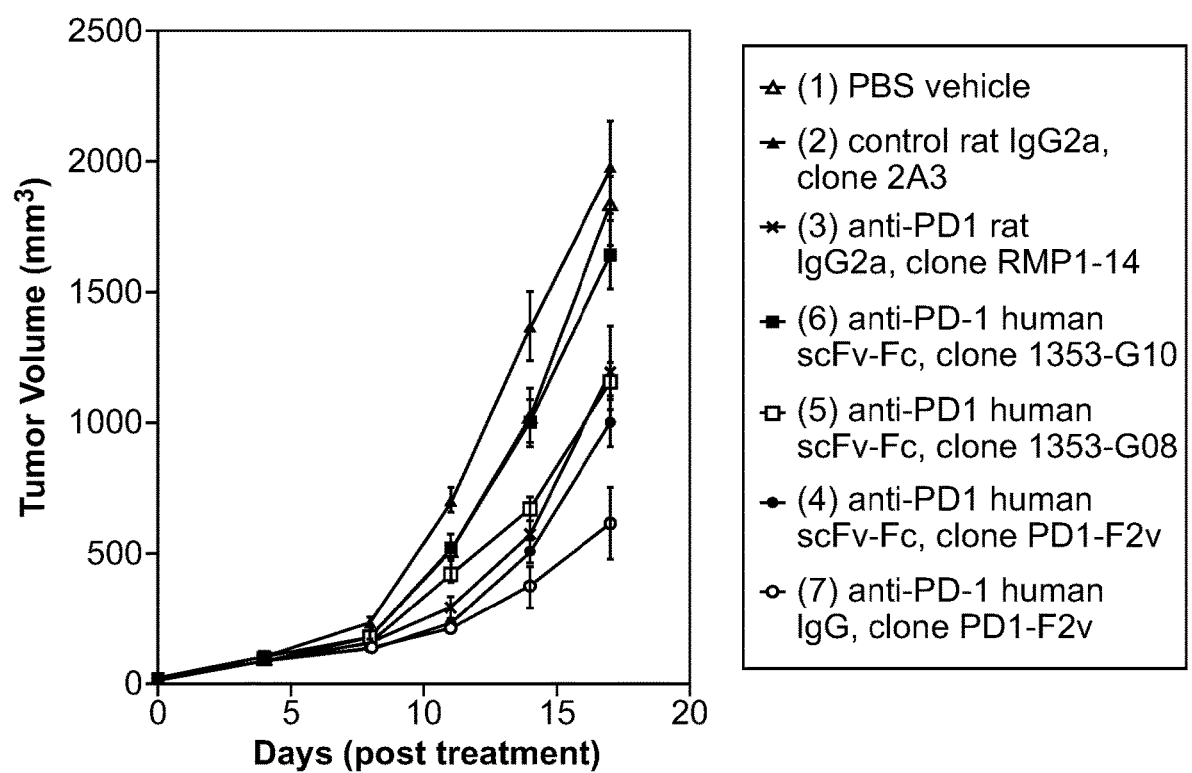
FIG. 2 provides a chart of tumor volume over 17-days of treatment with various anti-PD-1 antibodies, as described in Example 15.

FIG. 2 provides a chart of the tumor volume over the 17-days of treatment with the various antibodies.

Example 16: Cytomegalovirus (CMV) Recall Assay

Anti-PD-1 antibodies were functionally tested for potency in blocking the PD-1 pathway in restimulating peripheral blood mononuclear cells (PBMC) from cytomegalovirus-positive (CMV+) human donors by measuring IFN-g secretion in cell culture medium.

CD14+ monocytes and CD3+ T cells were obtained from peripheral blood mononuclear cells (PBMC) isolated from CMV+ human donors (AllCells, Alameda, Calif.) using MACS Cell Separation kits (Miltenyi Biotec).

CD14+ monocytes were differentiated into immature dendritic cells (DC) by culturing cells at 1×10$^6$ cells/ml for 7 days in presence of GM-CSF and IL-4 (Peprotech) in X-Vivo 15 media (Lonza) containing 2% human AB serum (Sigma-Aldrich), penicillin-streptomycin (Corning Mediatech) and GlutaMAX (Life Technologies). Following differentiation, DCs were matured by culturing in X-Vivo 15+2% human AB serum media at 1×10$^6$ cells/ml for 2 days in the presence of GM-CSF, IL-4, TNF-a, IL-1b, IL-6 (Peprotech) and prostaglandin E2 (Sigma-Aldrich).

To set-up the CMV recall assay, mature DCs were collected and washed. 10,000 DCs and 100,000 pan CD3+ T cells were plated per well in a 96-well U-bottom plate in a total volume of 100 µl media containing peptide pools for the CMV IE-1 and CMV pp65 proteins (Miltenyi Biotec).

Anti-PD-1 or control human IgG antibody (50 µl, final volume of 150 µl per well) were added starting at a final concentration of 400 nM with 5-fold serial dilutions. Cells were co-cultured with peptides and antibodies for 5-6 days. Conditioned media was collected and tested for human IFN-g levels by ELISA (BD Biosciences).

As shown in FIG. 3, anti-PD-1 human IgG 1353-G10 (SEQ ID NOs: 252 and 276) showed significant fold-increase in IFN-g levels (closed circles). The IFN-g levels were substantial compared to Nivolumab IgG (open circles).

Example 17: DC/CD4+ T cell Mixed Lymphocyte Reaction (MLR) Assay

Anti-PD-1 antibodies were functionally tested for potency in blocking the PD-1 pathway in a peripheral blood mononuclear cell (PBMC) two-way mixed lymphocyte reaction (MLR) assay by measuring interferon gamma (IFN-g) secretion in cell culture medium.

CD14+ monocytes and CD4+ T cells were obtained from PBMC isolated from human donors using MACS Cell Separation kits. CD14+ monocytes were differentiated into immature DC by culturing cells at 1×10$^6$ cells/ml cell density for 7 days in presence of GM-CSF and IL-4 in RPMI media containing 10% fetal bovine serum, penicillin-streptomycin and GlutaMAX.

Following differentiation, DCs were matured by culturing in RPMI+10% FBS media at 1×10$^6$ cells/ml cell density for 2 days in the presence of GM-CSF, IL-4, TNF-a, IL-1b, IL-6 and prostaglandin E2.

To set-up the DC/CD4+ T cell MLR, mature DCs were collected and washed. 10,000 DCs and 100,000 CD4+ T cells were plated per well in a 96-well U-bottom plate in a total volume of 100 µl media. Anti-PD-1 or control human IgG antibody (50 µl, final volume of 150 µl per well) were added starting at a final concentration of 400 nM with 5-fold serial dilutions. Cells were co-cultured with peptides and antibodies for 5-6 days. Conditioned media was collected and tested for human IFN-g levels by ELISA.

As shown in FIG. 4, anti-PD-1 human IgG 1353-G10 (SEQ ID NOs: 252 and 276) showed significant fold-increase in IFN-g levels (closed circles). The IFN-g levels were substantial compared to Nivolumab IgG (open circles).

Example 18: Effect of PD-1 Blockade on Graft Versus Host Disease (GVHD) Response Anti-PD-1 antibodies described herein were evaluated for acceleration of graft versus host disease (GVHD) in a mouse model. Since PD-1 negatively regulates immune response, blockade of PD-1 by an effective antibody should accelerate the immune and GVHD response.

40 female NSG mice aged 7 weeks and weighing approximately 19-22 g were used as human PBMC recipients. Groups were randomized into four groups of ten. On day 0, all animals received 2×10$^7$ human PBMC injected via the tail vein. Prior to PBMC injection, animals were dosed intraperitoneally (IP) with either control anti-GFP, Nivolumab anti-PD-1 antibody, or 1353-G10 anti-PD1 antibody (SEQ ID NOs: 252 and 276) as detailed in Table 9. Treatment was administered 2× per week until study conclusion.

TABLE 9

Treatment groups

| Group | huPBMC concentration | Test article | Dose | Dosing frequency | Total number of doses | Route | N |
|---|---|---|---|---|---|---|---|
| 1 | $2 \times 10^7$ | Control Anti-GFP | 10 mg/kg | 2x/week | 10 | IP | 10 |
| 2 | $2 \times 10^7$ | Anti-PD1 Nivolumab | 10 mg/kg | 2x/week | 10 | IP | 10 |
| 3 | $2 \times 10^7$ | Anti-PD1 1353-G10 | 10 mg/kg | 2x/week | 10 | IP | 10 |
| 4 | $2 \times 10^7$ | Anti-PD1 1353-G10 | 3 mg/kg | 2x/week | 10 | IP | 10 |

Animals were weighed and observed at least two times per week for 5 weeks. Monitoring increased to daily when 10% body weight loss (compared to initial mouse weight) occurred. Animals were euthanized with $CO_2$ at the end of five weeks (end of study), when they exhibited weight loss greater than 20%, or were unable to right themselves, cold to the touch, and moribund (severe hair ruffling, body weight loss, hunched posture, or decreased activity).

Upon sacrifice (after 5 weeks) or pre-mature euthanasia (due to body weight loss or moribundity), the spleen, liver, and serum were collected for further analyses. The liver and spleen were placed in formalin for 24 hours then transferred to 70% ethanol for storage. The serum was flash frozen and stored at −80° C. All procedures were conducted according to the guidelines of the Sutro Institutional Animal Care and Use Committee (IACUC) and Sutro IACUC protocol SU-001-2013

As shown in FIG. 5, anti-PD-1 treatment with human IgG 1353-G10 (SEQ ID NOs: 252 and 276) showed accelerated mouse morbidity by approximately two weeks (median survival of 13 days for 10 mg/kg 1353-G10 versus 27 days for anti-GFP control). The onset of GVHD severity was similar in mice treated with high (10 mg/kg) and low (3 mg/kg) 1353-G10. Body weight loss was also faster with both doses of 1353-G10 compared to control and Nivolumab (data not shown). Median survival with both doses of 1353-G10 was less compared to Nivolumab, indicating greater PD-1 blockade potency for 1353-G10 in vivo.

Example 19: Sequences

Table 10 provides sequences referred to herein.

TABLE 10

Sequences.

| SEQ ID NO | Molecule | Region | Scheme | Sequence |
|---|---|---|---|---|
| 1 | hPD-1 | | | MQIPQAPWPVVWAVLQLGWRPGWFLDSPDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQFQTLVVGVVGGLLGSLVLLVWVLAVICSRAARGTIGARRTGQPLKEDPSAVPVFSVDYGELDFQWREKTPEPPVPCVPEQTEYATIVFPSGMGTSSPARRGSADGPRSAQPLRPEDGHCSWPL |
| 2 | PD1-17 | CDR-H1 | | SGGSIRSTRWWS |
| 3 | PD1-28 | CDR-H1 | | SYGIS |
| 4 | PD1-33 | CDR-H1 | | SYYIH |
| 5 | PD1-35 | CDR-H1 | | SGAYYWS |
| 6 | PD1-F2 | CDR-H1 | | SSYWMS |
| 7 | 10B4 | CDR-H1 | Chothia | GYIFSSY |
| 8 | 1353-A09 | CDR-H1 | Chothia | GYRFTWY |
| 9 | 1353-C07 | CDR-H1 | Chothia | GYRFSTF |
| 10 | 1353-E07 | CDR-H1 | Chothia | GYRFETY |
| 11 | 1353-F09 | CDR-H1 | Chothia | GYRFRQY |
| 12 | 1353-G08 | CDR-H1 | Chothia | GYRFTRY |
| 13 | 1353-G10 | CDR-H1 | Chothia | GYRFPHY |

TABLE 10-continued

Sequences.

| SEQ ID NO | Molecule | Region | Scheme | Sequence |
|---|---|---|---|---|
| 14 | 1353-H08 | CDR-H1 | Chothia | GYRFTRQ |
| 15 | 1353-H09 | CDR-H1 | Chothia | GYRFPHY |
| 16 | 1B10 | CDR-H1 | Chothia | GHSITSDY |
| 17 | 1E9 | CDR-H1 | Chothia | GFTFSTF |
| 18 | 4B10 | CDR-H1 | Chothia | GFTFSTY |
| 19 | h1E9-1 | CDR-H1 | Chothia | GFTFSTF |
| 20 | h1E9-2 | CDR-H1 | Chothia | GFTFSTF |
| 21 | h1E9-4 | CDR-H1 | Chothia | GFTFSTF |
| 22 | h1E9-5 | CDR-H1 | Chothia | GFTFSTF |
| 23 | h4B10-1 | CDR-H1 | Chothia | GFTFSTY |
| 24 | h4B10-2 | CDR-H1 | Chothia | GFTFSTY |
| 25 | h4B10-3 | CDR-H1 | Chothia | GFTFSTY |
| 26 | PD1-17 | CDR-H1 | Chothia | GGSIGSGGSIRSTR |
| 27 | PD1-28 | CDR-H1 | Chothia | GYRFTSY |
| 28 | PD1-33 | CDR-H1 | Chothia | GYTLTSY |
| 29 | PD1-35 | CDR-H1 | Chothia | GGSISSGAY |
| 30 | PD1-F2 | CDR-H1 | Chothia | GFTFSSYWCD |
| 31 | 10B4 | CDR-H1 | Kabat | SYWIG |
| 32 | 1353-A09 | CDR-H1 | Kabat | WYGIS |
| 33 | 1353-C07 | CDR-H1 | Kabat | TFGIS |
| 34 | 1353-E07 | CDR-H1 | Kabat | TYGIS |
| 35 | 1353-F09 | CDR-H1 | Kabat | QYGIS |
| 36 | 1353-G08 | CDR-H1 | Kabat | RYGIS |
| 37 | 1353-G10 | CDR-H1 | Kabat | HYGIS |
| 38 | 1353-H08 | CDR-H1 | Kabat | RQGIS |
| 39 | 1353-H09 | CDR-H1 | Kabat | HYGIS |
| 40 | 1B10 | CDR-H1 | Kabat | SDYAWN |
| 41 | 1E9 | CDR-H1 | Kabat | TFGMS |
| 42 | 4B10 | CDR-H1 | Kabat | TYGMS |
| 43 | h1E9-1 | CDR-H1 | Kabat | TFGMS |
| 44 | h1E9-2 | CDR-H1 | Kabat | TFGMS |
| 45 | h1E9-4 | CDR-H1 | Kabat | TFGMS |
| 46 | h1E9-5 | CDR-H1 | Kabat | TFGMS |
| 47 | h4B10-1 | CDR-H1 | Kabat | TYGMS |
| 48 | h4B10-2 | CDR-H1 | Kabat | TYGMS |
| 49 | h4B10-3 | CDR-H1 | Kabat | TYGMS |
| 50 | PD1-17 | CDR-H1 | Kabat | SGGSIRSTRWWS |

TABLE 10-continued

Sequences.

| SEQ ID NO | Molecule | Region | Scheme | Sequence |
|---|---|---|---|---|
| 51 | PD1-28 | CDR-H1 | Kabat | SYGIS |
| 52 | PD1-33 | CDR-H1 | Kabat | SYYIH |
| 53 | PD1-35 | CDR-H1 | Kabat | SGAYYWS |
| 54 | PD1-F2 | CDR-H1 | Kabat | SYWCDRMS |
| 55 | PD1-17 | CDR-H2 | | EIYHSGSTNYNPSLKS |
| 56 | PD1-28 | CDR-H2 | | WISAYNGNTNYAQKLQG |
| 57 | PD1-33 | CDR-H2 | | IINPRGATISYAQKFQG |
| 58 | PD1-35 | CDR-H2 | | YIYYNGNTYYNPSLRS |
| 59 | PD1-F2 | CDR-H2 | | AISGSGGSTYYADSVKG |
| 60 | 10B4 | CDR-H2 | Chothia | FPGSGS |
| 61 | 1353-A09 | CDR-H2 | Chothia | SAYNGN |
| 62 | 1353-C07 | CDR-H2 | Chothia | SAYNGN |
| 63 | 1353-E07 | CDR-H2 | Chothia | SAYNGN |
| 64 | 1353-F09 | CDR-H2 | Chothia | SAYNGN |
| 65 | 1353-G08 | CDR-H2 | Chothia | SAHNGN |
| 66 | 1353-G10 | CDR-H2 | Chothia | SAYNGN |
| 67 | 1353-H08 | CDR-H2 | Chothia | SAYNGN |
| 68 | 1353-H09 | CDR-H2 | Chothia | SAYNGN |
| 69 | 1B10 | CDR-H2 | Chothia | SYSGR |
| 70 | 1E9 | CDR-H2 | Chothia | SGGGSD |
| 71 | 4B10 | CDR-H2 | Chothia | SGGGSN |
| 72 | h1E9-1 | CDR-H2 | Chothia | SGGGSD |
| 73 | h1E9-2 | CDR-H2 | Chothia | SGGGSD |
| 74 | h1E9-4 | CDR-H2 | Chothia | SGGGSD |
| 75 | h1E9-5 | CDR-H2 | Chothia | SGGGSD |
| 76 | h4B10-1 | CDR-H2 | Chothia | SGGGSN |
| 77 | h4B10-2 | CDR-H2 | Chothia | SGGGSN |
| 78 | h4B10-3 | CDR-H2 | Chothia | SGGGSN |
| 79 | PD1-17 | CDR-H2 | Chothia | YHSGS |
| 80 | PD1-28 | CDR-H2 | Chothia | SAYNGN |
| 81 | PD1-33 | CDR-H2 | Chothia | NPRGAT |
| 82 | PD1-35 | CDR-H2 | Chothia | YYNGN |
| 83 | PD1-F2 | CDR-H2 | Chothia | SGSGGS |
| 84 | 10B4 | CDR-H2 | Kabat | KIFPGSGSADYNENFKG |
| 85 | 1353-A09 | CDR-H2 | Kabat | WISAYNGNTNYAQKLQG |
| 86 | 1353-C07 | CDR-H2 | Kabat | WISAYNGNTNYAQKLQG |
| 87 | 1353-E07 | CDR-H2 | Kabat | WISAYNGNTNYAQKLQG |

TABLE 10-continued

Sequences.

| SEQ ID NO | Molecule | Region | Scheme | Sequence |
|---|---|---|---|---|
| 88 | 1353-F09 | CDR-H2 | Kabat | WISAYNGNTNYAQKLQG |
| 89 | 1353-G08 | CDR-H2 | Kabat | WVSAHNGNTNYAQKLQG |
| 90 | 1353-G10 | CDR-H2 | Kabat | WISAYNGNTNYAQKLQG |
| 91 | 1353-H08 | CDR-H2 | Kabat | WISAYNGNTKYAQKLQG |
| 92 | 1353-H09 | CDR-H2 | Kabat | WISAYNGNTNYAQKLQG |
| 93 | 1B10 | CDR-H2 | Kabat | YISYSGRTSYNPSLTS |
| 94 | 1E9 | CDR-H2 | Kabat | TISGGGSDTYYPDSVQG |
| 95 | 4B10 | CDR-H2 | Kabat | TISGGGSNTYYSDSVKG |
| 96 | h1E9-1 | CDR-H2 | Kabat | TISGGGSDTYYPDSVQG |
| 97 | h1E9-2 | CDR-H2 | Kabat | TISGGGSDTYYPDSVQG |
| 98 | h1E9-4 | CDR-H2 | Kabat | TISGGGSDTYYPDSVQG |
| 99 | h1E9-5 | CDR-H2 | Kabat | TISGGGSDTYYPDSVQG |
| 100 | h4B10-1 | CDR-H2 | Kabat | TISGGGSNTYYSDSVKG |
| 101 | h4B10-2 | CDR-H2 | Kabat | TISGGGSNTYYSDSVKG |
| 102 | h4B10-3 | CDR-H2 | Kabat | TISGGGSNTYYSDSVKG |
| 103 | PD1-17 | CDR-H2 | Kabat | EIYHSGSTNYNPSLKS |
| 104 | PD1-28 | CDR-H2 | Kabat | WISAYNGNTNYAQKLQG |
| 105 | PD1-33 | CDR-H2 | Kabat | IINPRGATISYAQKFQG |
| 106 | PD1-35 | CDR-H2 | Kabat | YIYYNGNTYYNPSLRS |
| 107 | PD1-F2 | CDR-H2 | Kabat | AISGSGGSTYYADSVKG |
| 108 | PD1-17 | CDR-H3 | | QDYGDSGDWYFDL |
| 109 | PD1-28 | CDR-H3 | | DADYSSGSGY |
| 110 | PD1-33 | CDR-H3 | | AGIYGFDFDY |
| 111 | PD1-35 | CDR-H3 | | ASDYVWGGYRYMDAFDI |
| 112 | PD1-F2 | CDR-H3 | | ENWGSYFDL |
| 113 | 10B4 | CDR-H3 | | GYGNYLYFDV |
| 114 | 1353-A09 | CDR-H3 | | DSEYSSGSGY |
| 115 | 1353-C07 | CDR-H3 | | DVDYSSGSGY |
| 116 | 1353-E07 | CDR-H3 | | DAEYSLGSGY |
| 117 | 1353-F09 | CDR-H3 | | DAEYGSGSGY |
| 118 | 1353-G08 | CDR-H3 | | DADYGSGSGY |
| 119 | 1353-G10 | CDR-H3 | | DVDYGTGSGY |
| 120 | 1353-H08 | CDR-H3 | | DVDYGSGSGY |
| 121 | 1353-H09 | CDR-H3 | | DAEYGSGSGY |
| 122 | 1B10 | CDR-H3 | | GYALDY |
| 123 | 1E9 | CDR-H3 | | QGYDVYSWFAY |
| 124 | 4B10 | CDR-H3 | | QRDSAWFAS |

TABLE 10-continued

Sequences.

| SEQ ID NO | Molecule | Region | Scheme | Sequence |
|---|---|---|---|---|
| 125 | h1E9-1 | CDR-H3 | | QGYDVYSWFAY |
| 126 | h1E9-2 | CDR-H3 | | QGYDVYSWFAY |
| 127 | h1E9-4 | CDR-H3 | | QGYDVYSWFAY |
| 128 | h1E9-5 | CDR-H3 | | QGYDVYSWFAY |
| 129 | h4B10-1 | CDR-H3 | | QRDSAWFAS |
| 130 | h4B10-2 | CDR-H3 | | QRDSAWFAS |
| 131 | h4B10-3 | CDR-H3 | | QRDSAWFAS |
| 132 | PD1-17 | CDR-H3 | | QDYGDSGDWYFDL |
| 133 | PD1-28 | CDR-H3 | | DADYSSGSGY |
| 134 | PD1-33 | CDR-H3 | | AGIYGFDFDY |
| 135 | PD1-35 | CDR-H3 | | ASDYVWGGYRYMDAFDI |
| 136 | PD1-F2 | CDR-H3 | | ENWGSYFDL |
| 137 | PD1-17 | CDR-L1 | | TRSSGSIASNSVQ |
| 138 | PD1-28 | CDR-L1 | | SGDALPKQYAY |
| 139 | PD1-33 | CDR-L1 | | TGTSNDVGGYNYVS |
| 140 | PD1-35 | CDR-L1 | | SGSNSNIGSNSVN |
| 141 | PD1-F2 | CDR-L1 | | RASQGISSWLA |
| 142 | 10B4 | CDR-L1 | | KASQSVSDDVA |
| 143 | 1353-A09 | CDR-L1 | | SGDALTTQYAY |
| 144 | 1353-C07 | CDR-L1 | | SGDALSEQYAY |
| 145 | 1353-E07 | CDR-L1 | | SGDALPKQYAY |
| 146 | 1353-F09 | CDR-L1 | | SGDALPKQYAY |
| 147 | 1353-G08 | CDR-L1 | | SGDALPMQYGY |
| 148 | 1353-G10 | CDR-L1 | | SGDALPKQYAY |
| 149 | 1353-H08 | CDR-L1 | | SGDALPKQYAY |
| 150 | 1353-H09 | CDR-L1 | | SGDALPKQYAY |
| 151 | 1B10 | CDR-L1 | | RTSSSVNYMH |
| 152 | 1E9 | CDR-L1 | | RASESVDNSGISFMS |
| 153 | 4B10 | CDR-L1 | | RASENVDDYGVSFMN |
| 154 | h1E9-1 | CDR-L1 | | RASESVDNSGISFMS |
| 155 | h1E9-2 | CDR-L1 | | RASESVDNSGISFMS |
| 156 | h1E9-4 | CDR-L1 | | RASESVDNSGISFMS |
| 157 | h1E9-5 | CDR-L1 | | RASESVDNSGISFMS |
| 158 | h4B10-1 | CDR-L1 | | RASENVDDYGVSFMN |
| 159 | h4B10-2 | CDR-L1 | | RASENVDDYGVSFMN |
| 160 | h4B10-3 | CDR-L1 | | RASENVDDYGVSFMN |
| 161 | PD1-17 | CDR-L1 | | TRSSGSIASNSVQ |

TABLE 10-continued

Sequences.

| SEQ ID NO | Molecule | Region | Scheme | Sequence |
|---|---|---|---|---|
| 162 | PD1-28 | CDR-L1 | | SGDALPKQYAY |
| 163 | PD1-33 | CDR-L1 | | TGTSNDVGGYNYVS |
| 164 | PD1-35 | CDR-L1 | | SGSNSNIGSNSVN |
| 165 | PD1-F2 | CDR-L1 | | RASQGISSWLA |
| 166 | PD1-17 | CDR-L2 | | EDNQRPS |
| 167 | PD1-28 | CDR-L2 | | KDTERPS |
| 168 | PD1-33 | CDR-L2 | | DVTNRPS |
| 169 | PD1-35 | CDR-L2 | | GNNQRPS |
| 170 | PD1-F2 | CDR-L2 | | KASTLES |
| 171 | 10B4 | CDR-L2 | | YAFKRYI |
| 172 | 1353-A09 | CDR-L2 | | KDTERPS |
| 173 | 1353-C07 | CDR-L2 | | KDTERPS |
| 174 | 1353-E07 | CDR-L2 | | KDTERPS |
| 175 | 1353-F09 | CDR-L2 | | KDTERPS |
| 176 | 1353-G08 | CDR-L2 | | KDTERPS |
| 177 | 1353-G10 | CDR-L2 | | KDTERPS |
| 178 | 1353-H08 | CDR-L2 | | KDTERPS |
| 179 | 1353-H09 | CDR-L2 | | KDTERPS |
| 180 | 1B10 | CDR-L2 | | ATSKLAS |
| 181 | 1E9 | CDR-L2 | | TASNQGS |
| 182 | 4B10 | CDR-L2 | | PASNQGS |
| 183 | h1E9-1 | CDR-L2 | | TASNQGS |
| 184 | h1E9-2 | CDR-L2 | | TASNQGS |
| 185 | h1E9-4 | CDR-L2 | | TASNQGS |
| 186 | h1E9-5 | CDR-L2 | | TASNQGS |
| 187 | h4B10-1 | CDR-L2 | | PASNQGS |
| 188 | h4B10-2 | CDR-L2 | | PASNQGS |
| 189 | h4B10-3 | CDR-L2 | | PASNQGS |
| 190 | PD1-17 | CDR-L2 | | EDNQRPS |
| 191 | PD1-28 | CDR-L2 | | KDTERPS |
| 192 | PD1-33 | CDR-L2 | | DVTNRPS |
| 193 | PD1-35 | CDR-L2 | | GNNQRPS |
| 194 | PD1-F2 | CDR-L2 | | KASTLES |
| 195 | PD1-17 | CDR-L3 | | QSSDSSAVV |
| 196 | PD1-28 | CDR-L3 | | QSADNSITYRV |
| 197 | PD1-33 | CDR-L3 | | SSYTIVTNFEVL |
| 198 | PD1-35 | CDR-L3 | | AAWDDSLNGPV |

TABLE 10-continued

Sequences.

| SEQ ID NO | Molecule | Region | Scheme | Sequence |
|---|---|---|---|---|
| 199 | PD1-F2 | CDR-L3 | | QQSYSTPWT |
| 200 | 10B4 | CDR-L3 | | QQNYNSPYT |
| 201 | 1353-A09 | CDR-L3 | | QSADNSITYRV |
| 202 | 1353-C07 | CDR-L3 | | QSADNSITYRV |
| 203 | 1353-E07 | CDR-L3 | | QSADNSITYRV |
| 204 | 1353-F09 | CDR-L3 | | QSADNSITYRV |
| 205 | 1353-G08 | CDR-L3 | | QSADNSITYRV |
| 206 | 1353-G10 | CDR-L3 | | QSADNSITYRV |
| 207 | 1353-H08 | CDR-L3 | | QSADNSITYRV |
| 208 | 1353-H09 | CDR-L3 | | QSADNSITYRV |
| 209 | 1B10 | CDR-L3 | | QQWISDPWT |
| 210 | 1E9 | CDR-L3 | | QQSKEVPWT |
| 211 | 4B10 | CDR-L3 | | QQSKEVPWT |
| 212 | h1E9-1 | CDR-L3 | | QQSKEVPWT |
| 213 | h1E9-2 | CDR-L3 | | QQSKEVPWT |
| 214 | h1E9-4 | CDR-L3 | | QQSKEVPWT |
| 215 | h1E9-5 | CDR-L3 | | QQSKEVPWT |
| 216 | h4B10-1 | CDR-L3 | | QQSKEVPWT |
| 217 | h4B10-2 | CDR-L3 | | QQSKEVPWT |
| 218 | h4B10-3 | CDR-L3 | | QQSKEVPWT |
| 219 | PD1-17 | CDR-L3 | | QSSDSSAVV |
| 220 | PD1-28 | CDR-L3 | | QSADNSITYRV |
| 221 | PD1-33 | CDR-L3 | | SSYTIVTNFEVL |
| 222 | PD1-35 | CDR-L3 | | AAWDDSLNGPV |
| 223 | PD1-F2 | CDR-L3 | | QQSYSTPWT |
| 224 | HC Constant | | | ASTKGPSVFPLAPSSKSTSGGTAALGCLVKD YFPEPVTVSWNSGALTSGVHTFPAVLQSS GLYSLSSVVTVPSSSLGTQTYINVNHKPSN TKVDKKVEPKSCDKTHTCPPCPAPELLGG PSVFLFPPKPKDTLMISRTPEVTCVVVDVSH EDPEVKFNWYVDGVEVHNAKTKPREEQYN STYRVVSVLTVLHQDWLNGKEYKCKVSNKAL PAPIEKTISKAKGQPREPQVYTLPPSREE MTKNQVSLTCLVKGFYPSDIAVEWESNGQPE NNYKTTPPVLDSDGSFFLYSKLTVDKSRW QQGNVFSCSVMHEALHNHYTQKSLSLSPGK |
| 225 | Kappa LC | | | HMTVAAPSVFIFPPSDEQLKSGTASVVCLLN NFYPREAKVQWKVDNALQSGNSQESVTEQ DSKDSTYSLSSTLTLSKADYEKHKVYACEVT HQGLSSPVTKSFNRGEC |
| 226 | Lambda LD | | | GQPKAAPSVTLFPPSSEELQANKATLVCLIS DFYPGAVTVAWKADSSPVKAGVETTTPSK QSNNKYAASSYLSLTPEQWKSHRSYSCQVTH EGSTVEKTVAPTECS |
| 227 | h1E9-1 | scFv | | MEVQLVESGGGLVKPGGSLRLSCAASGFTFS TFGMSWVRQAPGKGLEWVSTISGGGSDTY |

TABLE 10-continued

Sequences.

| SEQ ID NO | Molecule | Region | Scheme | Sequence |
|---|---|---|---|---|
| | | | | YPDSVQGRFTISRDNAKNSLYLQMNSLRAED<br>TAVYYCARQGYDVYSWFAYWGQGTLVTVS<br>SGGGGSGGGGSGGGGSDIQLTQSPSFLSASV<br>GDRVTITCRASESVDNSGISFMSWYQQKP<br>GKAPKLLIYTASNQGSVPSRFSGSGSGTEF<br>TLTISSLQPEDFATYYCQQSKEVPWTFGQ<br>GTKVEIKGSGDYKDDDDKGSGHHHHHH |
| 228 | h1E9-2 | scFv | | MEVQLVESGGGLVKPGGSLRLSCAASGFTFS<br>TFGMSWVRQAPGKGLEWVSTISGGGSDTY<br>YPDSVQGRFTISRDNAKNSLYLQMNSLRAED<br>TAVYYCARQGYDVYSWFAYWGQGTLVTVS<br>SGGGGSGGGGSGGGGSEIVLTQSPATLSLSP<br>GERATLSCRASESVDNSGISFMSWYQQKP<br>GQAPRLLIYTASNQGSGIPARFSGSGSGTDF<br>TLTISSLEPEDFAVYYCQQSKEVPWTFGQ<br>GTKVEIKGSGDYKDDDDKGSGHHHHHH |
| 229 | h1E9-4 | scFv | | MEVQLVESGGGLVQPGGSLRLSCAASGFTFS<br>TFGMSWVRQAPGKGLEWVATISGGGSDTY<br>YPDSVQGRFTISRDNAKNSLYLQMNSLRAED<br>TAVYYCARQGYDVYSWFAYWGQGTLVTVS<br>SGGGGSGGGGSGGGGSDIQLTQSPSFLSASV<br>GDRVTITCRASESVDNSGISFMSWYQQKP<br>GKAPKLLIYTASNQGSVPSRFSGSGSGTEF<br>TLTISSLQPEDFATYYCQQSKEVPWTFGQ<br>GTKVEIKGSGDYKDDDDKGSGHHHHHH |
| 230 | h1E9-5 | scFv | | MEVQLVESGGGLVQPGGSLRLSCAASGFTFS<br>TFGMSWVRQAPGKGLEWVATISGGGSDTY<br>YPDSVQGRFTISRDNAKNSLYLQMNSLRAED<br>TAVYYCARQGYDVYSWFAYWGQGTLVTVS<br>SGGGGSGGGGSGGGGSEIVLTQSPATLSLSP<br>GERATLSCRASESVDNSGISFMSWYQQKP<br>GQAPRLLIYTASNQGSGIPARFSGSGSGTDF<br>TLTISSLEPEDFAVYYCQQSKEVPWTFGQ<br>GTKVEIKGSGDYKDDDDKGSGHHHHHH |
| 231 | h4B10-1 | scFv | | MEVQLVESGGGLVKPGGSLRLSCAASGFTFS<br>TYGMSWVRQAPGKGLEWVATISGGGSNTY<br>YSDSVKGRFTISRDDSKNTLYLQMNSLKTED<br>TAVYYCARQRDSAWFASWGQGTLVTVSSG<br>GGGSGGGGSGGGGSEIVLTQSPATLSLSPGE<br>RATLSCRASENVDDYGVSFMNWYQQKPGQ<br>APRLLIYPASNQGSGIPARFSGSGSGTDFTL<br>TISSLEPEDFAVYYCQQSKEVPWTFGQGT<br>KVEIKGSGDYKDDDDKGSGHHHHHH |
| 232 | h4B10-2 | scFv | | MEVQLVESGGGLVKPGGSLRLSCAASGFTFS<br>TYGMSWVRQAPGKGLEWVATISGGGSNTY<br>YSDSVKGRFTISRDDSKNTLYLQMNSLKTED<br>TAVYYCARQRDSAWFASWGQGTLVTVSSG<br>GGGSGGGGSGGGGSEIVLTQSPGTLSLSPGE<br>RATLSCRASENVDDYGVSFMNWYQQKPGQ<br>APRLLIYPASNQGSGIPDRFSGSGSGTDFTL<br>TISRLEPEDFAVYYCQQSKEVPWTFGQGT<br>KVEIKGSGDYKDDDDKGSGHHHHHH |
| 233 | h4B10-3 | scFv | | MEVQLVESGGGLVKPGGSLRLSCAASGFTFS<br>TYGMSWVRQAPGKGLEWVATISGGGSNTY<br>YSDSVKGRFTISRDDSKNTLYLQMNSLKTED<br>TAVYYCARQRDSAWFASWGQGTLVTVSSG<br>GGGSGGGGSGGGGSDIVMTQSPDSLAVSLGE<br>RATINCRASENVDDYGVSFMNWYQQKPGQ<br>PPKLLIYPASNQGSGVPDRFSGSGSGTDFTL<br>TISSLQAEDVAVYYCQQSKEVPWTFGGGT<br>KLEIKGSGDYKDDDDKGSGHHHHHH |
| 234 | m10B4 | scFv | | MQVQLQQSGAELMKPGASVKMSCKTTGYIFS<br>SYWIGWVKQRPGHGLEWIGKIFPGSGSADYN<br>ENFKGKATFTVDTSSNTAYMQLSSLTSEDSA<br>VYYCARGYGNYLYFDVWGAGTTVTVSSGGGG<br>SGGGGSGGGGSNIVMTQTPKFLLVSAGDRIT<br>ITCKASQSVSDDVAWYQQKPGQSPKLLISYA |

TABLE 10-continued

Sequences.

| SEQ ID NO | Molecule | Region | Scheme | Sequence |
|---|---|---|---|---|
| | | | | FKRYIGVPDRFTGSGYGTDFTFTISTVQAED LAVYFCQQNYNSPYTFGGGTKLELKGSGDYK DDDDKGSGHHHHHH |
| 235 | m1B10 | scFv | | MSDVQLQESGPGLVKPSQSLSLTCTVTGHSI TSDYAWNWIRQFPGNKLEWMGYISYSGRTSY NPSLTSRISITRDTSKNQFFLQLNSVTTEDT ATYYCARGYALDYWGQGTSVTVSSGGGGSGG GGSGGGGSQIVLSQSPAILSASPGEKVTMTC RTSSSVNYMHWFQQKPGSSPKPWIYATSKLA SGVPARFSGSGSGTSYSLTISRVEAEDAATY FCQQWISDPWTFGGGTKLEIKGSGDYKDDDD KGSGHHHHHH |
| 236 | m1E9 | scFv | | MEVKLVESGGGLVSPGGSLKLSCAASGFTFS TFGMSWVRQTPEKRLEWVATISGGGSDTYYP DSVQGRFIISRYNAKNNLYLQMNSLRPEDTA LYYCARQGYDVYSWFAYWGQGTLVTVSAGGG GSGGGGSGGGGSDIILTQSPASLAVSLGQRA AISCRASESVDNSGISFMSWFQQKPGQPPKL LIYTASNQGSGVPARFSGSGSGTEFSLNIHP MEEDDTAMYFCQQSKEVPWTFGGGTKLEIRG SGDYKDDDDKGSGHHHHHH |
| 237 | m4B10 | scFv | | MEVKLVESGGGLVKPGGSLKLSCAASGFTFS TYGMSWVRQTPEKRLQWVATISGGGSNTYYS DSVKGRFTISRDNAKNNLYLQMSSLRSEDTA LYYCARQRDSAWFASWGQGTLVTVSAGGGGS GGGGSGGGGSDIVLTQSPASLAVSLGQRATI SCRASENVDDYGVSFMNWFQQKPGQPPKLLI YPASNQGSGVPARFSGSGSGTDFSLNIHPME EDDTAMYFCQQSKEVPWTFGGGTKLEIKGSG DYKDDDDKGSGHHHHHH |
| 238 | 1353-A09 | scFv-Fc | | MEVQLVQSGAEVKKPGASVKVSCKASGYRFT WYGISWVRQAPGQGLEWMGWISAYNGNTN YAQKLQGRVTMTTDTSTNTAYMELRSLRSDD TAVYYCARDSEYSSGSGYWGQGTLVTVSS GGGGSGGGGSGGGGSSYELTQPPSVSVSPGQ TARITCSGDALTTQYAYWYQQKPGQAPVM VIYKDTERPSGIPERFSGSSSGTKVTLTISG VQAEDEADYYCQSADNSITYRVFGGGTKV TVLAAGSDQEPKKLAAGSDQEPKSSDKTHTC PPCSAPELLGGSSVFLFPPKPKDTLMISR TPEVTCVVVDVSHEDPEVKFNWYVDGVEVHN AKTKPREEQYNSTYRVVSVLTVLHQDWLN GKEYKCKVSNKALPAPIEKTISKAKGQPREP QVYTLPPSRDELTKNQVSLTCLVKGFYPS DIAVEWESNGQPENNYKTTPPVLDSDGSFFL YSKLTVDKSRWQQGNVFSCSVMHEALHNH YTQKSLSLSPGKGSGDYKDDDDKGSGHHHHH H |
| 239 | 1353-C07 | scFv-Fc | | MEVQLVQSGAEVKKPGASVKVSCKASGYRFS TFGISWVRQAPGQGLEWMGWISAYNGNTN YAQKLQGRVTMTTDTSTNTAYMELRSLRSDD TAVYYCARDVDYSSGSGYWGQGTLVTVSS GGGGSGGGGSGGGGSSYELTQPPSVSVSPGQ TARITCSGDALSEQYAYWYQQKPGQAPVM VIYKDTERPSGIPERFSGSSSGTKVTLTISG VQAEDEADYYCQSADNSITYRVFGGGTKV TVLAAGSDQEPKKLAAGSDQEPKSSDKTHTC PPCSAPELLGGSSVFLFPPKPKDTLMISR TPEVTCVVVDVSHEDPEVKFNWYVDGVEVHN AKTKPREEQYNSTYRVVSVLTVLHQDWLN GKEYKCKVSNKALPAPIEKTISKAKGQPREP QVYTLPPSRDELTKNQVSLTCLVKGFYPS DIAVEWESNGQPENNYKTTPPVLDSDGSFFL YSKLTVDKSRWQQGNVFSCSVMHEALHNH YTQKSLSLSPGKGSGDYKDDDDKGSGHHHHH H |
| 240 | 1353-E07 | scFv-Fc | | MEVQLVQSGAEVKKPGASVKVSCKASGYRFE TYGISWVRQAPGQGLEWMGWISAYNGNTN |

TABLE 10-continued

Sequences.

| SEQ ID NO | Molecule | Region | Scheme | Sequence |
|---|---|---|---|---|
| | | | | YAQKLQGRVTMTTDTSTNTAYMELRSLRSDD TAVYYCARDAEYSLGSGYWGQGTLVTVSS GGGGSGGGGSGGGGSSYELTQPPSVSVSPGQ TARITCSGDALPKQYAYWYQQKPGQAPVM VIYKDTERPSGIPERFSGSSSGTKVTLTISG VQAEDEADYYCQSADNSITYRVFGGGTKV TVLAAGSDQEPKKLAAGSDQEPKSSDKTHTC PPCSAPELLGGSSVFLFPPKPKDTLMISR TPEVTCVVVDVSHEDPEVKFNWYVDGVEVHN AKTKPREEQYNSTYRVVSVLTVLHQDWLN GKEYKCKVSNKALPAPIEKTISKAKGQPREP QVYTLPPSRDELTKNQVSLTCLVKGFYPS DIAVEWESNGQPENNYKTTPPVLDSDGSFFL YSKLTVDKSRWQQGNVFSCSVMHEALHNH YTQKSLSLSPGKGSGDYKDDDDKGSGHHHHH H |
| 241 | 1353-F09 | scFv-Fc | | MEVQLVQSGAEVKKPGASVKVSCKASGYRFR QYGISWVRQAPGQGLEWMGWISAYNGNTN YAQKLQGRVTMTTDTSTNTAYMELRSLRSDD TAVYYCARDAEYGSGSGYWGQGTLVTVSS GGGGSGGGGSGGGGSSYELTQPPSVSVSPGQ TARITCSGDALPKQYAYWYQQKPGQAPVM VLYKDTERPSGIPERFSGSSSGTKVTLTISG VQAEDEADYYCQSADNSITYRVFGGGTKV TVLAAGSDQEPKKLAAGSDQEPKSSDKTHTC PPCSAPELLGGSSVFLFPPKPKDTLMISR TPEVTCVVVDVSHEDPEVKFNWYVDGVEVHN AKTKPREEQYNSTYRVVSVLTVLHQDWLN GKEYKCKVSNKALPAPIEKTISKAKGQPREP QVYTLPPSRDELTKNQVSLTCLVKGFYPS DIAVEWESNGQPENNYKTTPPVLDSDGSFFL YSKLTVDKSRWQQGNVFSCSVMHEALHNH YTQKSLSLSPGKGSGDYKDDDDKGSGHHHHH H |
| 242 | 1353-G08 | scFv-Fc | | MEVQLVQSGAEVKKPGASVKVSCKASGYRFT RYGISWVRQAPGQGLEWMGWVSAHNGNTN YAQKLQGRVTMTTDTSTNTAYMELRSLRSDD TAVYYCARDADYGSGSGYWGQGTLVTVSS GGGVSGGGGSGGGGSSYELTQPPSVSVSPGQ TARITCSGDALPMQYGYWYQQKPGQAPVM VIYKDTERPSGIPERFSGSSSGTKVTLTISG VQAEDEADYYCQSADNSITYRVFGGGTKV TVLAAGSDQEPKKLAAGSDQEPKSSDKTHTC PPCSAPELLGGSSVFLFPPKPKDTLMISR TPEVTCVVVDVSHEDPEVKFNWYVDGVEVHN AKTKPREEQYNSTYRVVSVLTVLHQDWLN GKEYKCKVSNKALPAPIEKTISKAKGQPREP QVYTLPPSRDELTKNQVSLTCLVKGFYPS DIAVEWESNGQPENNYKTTPPVLDSDGSFFL YSKLTVDKSRWQQGNVFSCSVMHEALHNH YTQKSLSLSPGKGSGDYKDDDDKGSGHHHHH H |
| 243 | 1353-G10 | scFv-Fc | | MEVQLVQSGAEVKKPGASVKVSCKASGYRFP HYGISWVRQAPGQGLEWMGWISAYNGNTN YAQKLQGRVTMTTDTSTNTAYMELRSLRSDD TAVYYCARDVDYGTGSGYWGQGTLVTVSS GGGGSGGGGSGGGGSSYELTQPPSVSVSPGQ TARITCSGDALPKQYAYWYQQKPGQAPVM VIYKDTERPSGIPERFSGSSSGTKVTLTISG VQAEDEADYYCQSADNSITYRVFGGGTKV TVLAAGSDQEPKKLAAGSDQEPKSSDKTHTC PPCSAPELLGGSSVFLFPPKPKDTLMISR TPEVTCVVVDVSHEDPEVKFNWYVDGVEVHN AKTKPREEQYNSTYRVVSVLTVLHQDWLN GKEYKCKVSNKALPAPIEKTISKAKGQPREP QVYTLPPSRDELTKNQVSLTCLVKGFYPS DIAVEWESNGQPENNYKTTPPVLDSDGSFFL YSKLTVDKSRWQQGNVFSCSVMHEALHNH YTQKSLSLSPGKGSGDYKDDDDKGSGHHHHH H |

TABLE 10-continued

Sequences.

| SEQ ID NO | Molecule | Region | Scheme | Sequence |
|---|---|---|---|---|
| 244 | 1353-H08 | scFv-Fc | | MEVQLVQSGAEVKKPGASVKVSCKASGYRFT RQGISWVRQAPGQGLEWMGWISAYNGNTK YAQKLQGRVTMTTDTSTNTAYMELRSLRSDD TAVYYCARDVDYGSGSGYWGQGTLVTVSS GGGGSGGGGSGGGGSSYELTQPPSVSVSPGQ TARITCSGDALPKQYAYWYQQKPGQAPVM VIYKDTERPSGIPERFSGSSSGTKVTLTISG VQAEDEADYYCQSADNSITYRVFGGGTKV TVLAAGSDQEPKKLAAGSDQEPKSSDKTHTC PPCSAPELLGGSSVFLFPPKPKDTLMISR TPEVTCVVVDVSHEDPEVKFNWYVDGVEVHN AKTKPREEQYNSTYRVVSVLTVLHQDWLN GKEYKCKVSNKALPAPIEKTISKAKGQPREP QVYTLPPSRDELTKNQVSLTCLVKGFYPS DIAVEWESNGQPENNYKTTPPVLDSDGSFFL YSKLTVDKSRWQQGNVFSCSVMHEALHNH YTQKSLSLSPGKGSGDYKDDDDKGSGHHHHH H |
| 245 | 1353-H09 | scFv-Fc | | MEVQLVQSGAEVKKPGASVKVSCKASGYRFP HYGISWVRQAPGQGLEWMGWISAYNGNTN YAQKLQGRVTMTTDTSTNTAYMELRSLRSDD TAVYYCARDAEYGSGSGYWGQGTLVTVSS GGGGSGGGGSGGGGSSYELTQPPSVSVSPGQ TARITCSGDALPKQYAYWYQQKPGQAPVM VIYKDTERPSGIPERFSGSSSGTKVTLTISG VQAEDEADYYCQSADNSITYRVFGGGTKV TVLAAGSDQEPKKLAAGSDQEPKSSDKTHTC PPCSAPELLGGSSVFLFPPKPKDTLMISR TPEVTCVVVDVSHEDPEVKFNWYVDGVEVHN AKTKPREEQYNSTYRVVSVLTVLHQDWLN GKEYKCKVSNKALPAPIEKTISKAKGQPREP QVYTLPPSRDELTKNQVSLTCLVKGFYPS DIAVEWESNGQPENNYKTTPPVLDSDGSFFL YSKLTVDKSRWQQGNVFSCSVMHEALHNH YTQKSLSLSPGKGSGDYKDDDDKGSGHHHHH H |
| 246 | 10B4 | VH | | QVQLQQSGAELMKPGASVKMSCKTTGYIFSS YWIGWVKQRPGHGLEWIGKIFPGSGSADYNE NFKGKATFTVDTSSNTAYMQLSSLTSEDSAV YYCARGYGNYLYFDVWGAGTTVTVSS |
| 247 | 1353-A09 | VH | | EVQLVQSGAEVKKPGASVKVSCKASGYRFTW YGISWVRQAPGQGLEWMGWISAYNGNTN YAQKLQGRVTMTTDTSTNTAYMELRSLRSDD TAVYYCARDSEYSSGSGYWGQGTLVTVSS |
| 248 | 1353-C07 | VH | | EVQLVQSGAEVKKPGASVKVSCKASGYRFST FGISWVRQAPGQGLEWMGWISAYNGNTN YAQKLQGRVTMTTDTSTNTAYMELRSLRSDD TAVYYCARDVDYSSGSGYWGQGTLVTVSS |
| 249 | 1353-E07 | VH | | EVQLVQSGAEVKKPGASVKVSCKASGYRFET YGISWVRQAPGQGLEWMGWISAYNGNTN YAQKLQGRVTMTTDTSTNTAYMELRSLRSDD TAVYYCARDAEYSLGSGYWGQGTLVTVSS |
| 250 | 1353-F09 | VH | | EVQLVQSGAEVKKPGASVKVSCKASGYRFRQ YGISWVRQAPGQGLEWMGWISAYNGNTN YAQKLQGRVTMTTDTSTNTAYMELRSLRSDD TAVYYCARDAEYGSGSGYWGQGTLVTVSS |
| 251 | 1353-G08 | VH | | EVQLVQSGAEVKKPGASVKVSCKASGYRFTR YGISWVRQAPGQGLEWMGWVSAHNGNTN YAQKLQGRVTMTTDTSTNTAYMELRSLRSDD TAVYYCARDADYGSGSGYWGQGTLVTVSS |
| 252 | 1353-G10 | VH | | EVQLVQSGAEVKKPGASVKVSCKASGYRFPH YGISWVRQAPGQGLEWMGWISAYNGNTN YAQKLQGRVTMTTDTSTNTAYMELRSLRSDD TAVYYCARDVDYGTGSGYWGQGTLVTVSS |

TABLE 10-continued

Sequences.

| SEQ ID NO | Molecule | Region | Scheme | Sequence |
|---|---|---|---|---|
| 253 | 1353-H08 | VH | | EVQLVQSGAEVKKPGASVKVSCKASGYRFTRQGISWVRQAPGQGLEWMGWISAYNGNTKYAQKLQGRVTMTTDTSTNTAYMELRSLRSDDTAVYYCARDVDYGSGSGYWGQGTLVTVSS |
| 254 | 1353-H09 | VH | | EVQLVQSGAEVKKPGASVKVSCKASGYRFPHYGISWVRQAPGQGLEWMGWISAYNGNTNYAQKLQGRVTMTTDTSTNTAYMELRSLRSDDTAVYYCARDAEYGSGSGYWGQGTLVTVSS |
| 255 | 1B10 | VH | | DVQLQESGPGLVKPSQSLSLTCTVTGHSITSDYAWNWIRQFPGNKLEWMGYISYSGRTSYNPSLTSRISITRDTSKNQFFLQLNSVTTEDTATYYCARGYALDYWGQGTSVTVSS |
| 256 | 1E9 | VH | | EVKLVESGGGLVSPGGSLKLSCAASGFTFSTFGMSWVRQTPEKRLEWVATISGGGSDTYYPDSVQGRFIISRYNAKNNLYLQMNSLRPEDTALYYCARQGYDVYSWFAYWGQGTLVTVSA |
| 257 | 4B10 | VH | | EVKLVESGGGLVKPGGSLKLSCAASGFTFSTYGMSWVRQTPEKRLQWVATISGGGSNTYYSDSVKGRFTISRDNAKNNLYLQMSSLRSEDTALYYCARQRDSAWFASWGQGTLVTVSA |
| 258 | h1E9-1 | VH | | EVQLVESGGGLVKPGGSLRLSCAASGFTFSTFGMSWVRQAPGKGLEWVSTISGGGSDTYYPDSVQGRFTISRDNAKNSLYLQMNSLRAEDTAVYYCARQGYDVYSWFAYWGQGTLVTVS S |
| 259 | h1E9-2 | VH | | EVQLVESGGGLVKPGGSLRLSCAASGFTFSTFGMSWVRQAPGKGLEWVSTISGGGSDTYYPDSVQGRFTISRDNAKNSLYLQMNSLRAEDTAVYYCARQGYDVYSWFAYWGQGTLVTVS S |
| 260 | h1E9-4 | VH | | EVQLVESGGGLVQPGGSLRLSCAASGFTFSTFGMSWVRQAPGKGLEWVATISGGGSDTYYPDSVQGRFTISRDNAKNSLYLQMNSLRAEDTAVYYCARQGYDVYSWFAYWGQGTLVTVS S |
| 261 | h1E9-5 | VH | | EVQLVESGGGLVQPGGSLRLSCAASGFTFSTFGMSWVRQAPGKGLEWVATISGGGSDTYYPDSVQGRFTISRDNAKNSLYLQMNSLRAEDTAVYYCARQGYDVYSWFAYWGQGTLVTVS S |
| 262 | h4B10-1 | VH | | EVQLVESGGGLVKPGGSLRLSCAASGFTFSTYGMSWVRQAPGKGLEWVATISGGGSNTYYSDSVKGRFTISRDDSKNTLYLQMNSLKTEDTAVYYCARQRDSAWFASWGQGTLVTVSS |
| 263 | h4B10-2 | VH | | EVQLVESGGGLVKPGGSLRLSCAASGFTFSTYGMSWVRQAPGKGLEWVATISGGGSNTYYSDSVKGRFTISRDDSKNTLYLQMNSLKTEDTAVYYCARQRDSAWFASWGQGTLVTVSS |
| 264 | h4B10-3 | VH | | EVQLVESGGGLVKPGGSLRLSCAASGFTFSTYGMSWVRQAPGKGLEWVATISGGGSNTYYSDSVKGRFTISRDDSKNTLYLQMNSLKTEDTAVYYCARQRDSAWFASWGQGTLVTVSS |
| 265 | PD1-17 | VH | | QVQLQESGPGVVKPSGTLSLTCAISGGSIGSGGSIRSTRWWSWVRQSPGKGLEWIGEIYHSGSTNYNPSLKSRVTISLDKSRNHFSLRLNSVTAADTAVYYCARQDYGDSGDWYFDLWGKGTMVTVSS |
| 266 | PD1-28 | VH | | EVQLVQSGAEVKKPGASVKVSCKASGYRFTSYGISWVRQAPGQGLEWMGWISAYNGNTNYAQKLQGRVTMTTDTSTNTAYMELRSLRSDDTAVYYCARDADYSSGSGYWGQGTLVTVSS |
| 267 | PD1-33 | VH | | QVQLVQSGAEVKKPGASVRVSCKASGYTLTSYYIHWVRQAPGQGLEWMGIINPRGATISY |

TABLE 10-continued

Sequences.

| SEQ ID NO | Molecule | Region | Scheme | Sequence |
|---|---|---|---|---|
| | | | | AQKFQGRVTMTRDTSTSTVYMELRNLKSEDT ALYYCATAGIYGFDFDYWGRGTLVTVSS |
| 268 | PD1-35 | VH | | QVQLQESGPGLVKPSQTLSLTCTVSGGSISS GAYYWSWIRQHPGKGLEWIGYIYYNGNTY YNPSLRSLVTISVDASKNQFSLKLSSVTAAD TAVYYCARASDYVWGGYRYMDAFDIWGRG TLITVSS |
| 269 | PD1-F2 | VH | | EVQLVQSGGGVVQPGRSLRLSCAASGFTFSS YWCDRMSWVRQAPGKGLEWVSAISG SGGSTYYADSVKGRFTISRDNSKNTLYLQMN SLRAEDTAVYYCAKENWGSYFDLWGQGTT VTVSS |
| 270 | 10B4 | VL | | NIVMTQTPKFLLVSAGDRITITCKASQSVSD DVAWYQQKPGQSPKLLISYAFKRYIGVPDRF TGSGYGTDFTFTISTVQAEDLAVYFCQQNYN SPYTFGGGTKLELKR |
| 271 | 1353-A09 | VL | | SYELTQPPSVSVSPGQTARITCSGDALTTQY AYWYQQKPGQAPVM VIYKDTERPSGIPERFSGSSSGTKVTLTISG VQAEDEADYYCQSADNSITYRVFGGGTKV TVL |
| 272 | 1353-C07 | VL | | SYELTQPPSVSVSPGQTARITCSGDALSEQY AYWYQQKPGQAPVM VIYKDTERPSGIPERFSGSSSGTKVTLTISG VQAEDEADYYCQSADNSITYRVFGGGTKV TVL |
| 273 | 1353-E07 | VL | | SYELTQPPSVSVSPGQTARITCSGDALPKQY AYWYQQKPGQAPVM VIYKDTERPSGIPERFSGSSSGTKVTLTISG VQAEDEADYYCQSADNSITYRVFGGGTKV TVL |
| 274 | 1353-F09 | VL | | SYELTQPPSVSVSPGQTARITCSGDALPKQY AYWYQQKPGQAPVM VLYKDTERPSGIPERFSGSSSGTKVTLTISG VQAEDEADYYCQSADNSITYRVFGGGTKV TVL |
| 275 | 1353-G08 | VL | | SYELTQPPSVSVSPGQTARITCSGDALPMQY GYWYQQKPGQAPVM VIYKDTERPSGIPERFSGSSSGTKVTLTISG VQAEDEADYYCQSADNSITYRVFGGGTKV TVL |
| 276 | 1353-G10 | VL | | SYELTQPPSVSVSPGQTARITCSGDALPKQY AYWYQQKPGQAPVM VIYKDTERPSGIPERFSGSSSGTKVTLTISG VQAEDEADYYCQSADNSITYRVFGGGTKV TVL |
| 277 | 1353-H08 | VL | | SYELTQPPSVSVSPGQTARITCSGDALPKQY AYWYQQKPGQAPVM VIYKDTERPSGIPERFSGSSSGTKVTLTISG VQAEDEADYYCQSADNSITYRVFGGGTKV TVL |
| 278 | 1353-H09 | VL | | SYELTQPPSVSVSPGQTARITCSGDALPKQY AYWYQQKPGQAPVM VIYKDTERPSGIPERFSGSSSGTKVTLTISG VQAEDEADYYCQSADNSITYRVFGGGTKV TVL |
| 279 | 1B10 | VL | | QIVLSQSPAILSASPGEKVTMTCRTSSSVNY MHWFQQKPGSSPKPWIYATSKLASGVPARFS GSGSGTSYSLTISRVEAEDAATYFCQQWISD PWTFGGGTKLEIK |

TABLE 10-continued

Sequences.

| SEQ ID NO | Molecule | Region | Scheme | Sequence |
|---|---|---|---|---|
| 280 | 1E9 | VL | | DIILTQSPASLAVSLGQRAAISCRASESVDN SGISFMSWFQQKPGQPPKLLIYTASNQGSGV PARFSGSGSGTEFSLNIHPMEEDDTAMYFCQ QSKEVPWTFGGGTKLEIR |
| 281 | 4B10 | VL | | DIVLTQSPASLAVSLGQRATISCRASENVDD YGVSFMNWFQQKPGQPPKLLIYPASNQGSGV PARFSGSGSGTDFSLNIHPMEEDDTAMYFCQ QSKEVPWTFGGGTKLEIK |
| 282 | h1E9-1 | VL | | DIQLTQSPSFLSASVGDRVTITCRASESVDN SGISFMSWYQQKP GKAPKLLIYTASNQGSGVPSRFSGSGSGTEF TLTISSLQPEDFATYYCQQSKEVPWTFGQ GTKVEIK |
| 283 | h1E9-2 | VL | | EIVLTQSPATLSLSPGERATLSCRASESVDN SGISFMSWYQQKP GQAPRLLIYTASNQGSGIPARFSGSGSGTDF TLTISSLEPEDFAVYYCQQSKEVPWTFGQ GTKVEIK |
| 284 | h1E9-4 | VL | | DIQLTQSPSFLSASVGDRVTITCRASESVDN SGISFMSWYQQKPGKAPKLLIYTASNQGSGV PSRFSGSGSGTEFTLTISSLQPEDFATYYCQ QSKEVPWTFGQ GTKVEIK |
| 285 | h1E9-5 | VL | | EIVLTQSPATLSLSPGERATLSCRASESVDN SGISFMSWYQQKP GQAPRLLIYTASNQGSGIPARFSGSGSGTDF TLTISSLEPEDFAVYYCQQSKEVPWTFGQ GTKVEIK |
| 286 | h4B10-1 | VL | | EIVLTQSPATLSLSPGERATLSCRASENVDD YGVSFMNWYQQKPGQ APRLLIYPASNQGSGIPARFSGSGSGTDFTL TISSLEPEDFAVYYCQQSKEVPWTFGQGT KVEIK |
| 287 | h4B10-2 | VL | | EIVLTQSPGTLSLSPGERATLSCRASENVDD YGVSFMNWYQQKPGQ APRLLIYPASNQGSGIPDRFSGSGSGTDFTL TISRLEPEDFAVYYCQQSKEVPWTFGQGT KVEIK |
| 288 | h4B10-3 | VL | | DIVMTQSPDSLAVSLGERATINCRASENVDD YGVSFMNWYQQKPGQ PPKLLIYPASNQGSGVPDRFSGSGSGTDFTL TISSLQAEDVAVYYCQQSKEVPWTFGGGT KLEIK |
| 289 | PD1-17 | VL | | NFMLTQPHSVSESPGKTVTISCTRSSGSIAS NSVQWYQQRPGSSPTTVIYEDNQRPSGVP DRFSGSIDSSSNSASLTVSGLKTEDEADYYC QSSDSSAVVFGSGTKLTVL |
| 290 | PD1-28 | VL | | SYELTQPPSVSVSPGQTARITCSGDALPKQY AYWYQQKPGQAPVMVIYKDTERPSGIPER FSGSSSGTKVTLTISGVQAEDEADYYCQSAD NSITYRVFGGGTKVTVL |
| 291 | PD1-33 | VL | | QSALTQPASVSGSPGQSITISCTGTSNDVGG YNYVSWYQHHPGKAPKLIIYDVTNRPSGV SDRFSGSKSGNTASLTISGLLAEDEGDYYCS SYTIVTNFEVLFGGGTKLTV |
| 292 | PD1-35 | VL | | QSVLTQPPSASGTPGQRVTISCSGSNSNIGS NSVNWYQQLPGTAPKLLIYGNNQRPSGVP DRFSGSKSGTSASLAISGLQSENEADYYCAA WDDSLNGPVFGRGTKVTVL |
| 293 | PD1-F2 | VL | | DIVMTQSPSTLSASVGDRVTITCRASQGISS WLAWYQQKPGRAPKVLIYKASTLES |

TABLE 10-continued

Sequences.

| SEQ ID NO | Molecule | Region | Scheme | Sequence |
|---|---|---|---|---|
| | | | | GVPSRFSGSGSGTDFTLTISSLQPEDFATYY CQQSYSTPWTFGQGTKLEIK |
| 294 | FlagHis Tag | | | GSGDYKDDDDKGSGHHHHHH |
| 295 | IgG1 Fc from scFv-Fc | | | AAGSDQEPKSSDKTHTCPPCSAPELLGGSSV FLFPPKPKDTLMISRTPEVTCVVVDVSHEDP EVKFNWYVDGVEVHNAKTKPREEQYNSTYRV VSVLTVLHQDWLNGKEYKCKVSNKALPAPIE KTISKAKGQPREPQVYTLPPSRDELTKNQVS LTCLVKGFYPSDIAVEWESNGQPENNYKTTP PVLDSDGSFFLYSKLTVDKSRWQQGNVFSCS VMHEALHNHYTQKSLSLSPGKGSGDYKDDDD KGSG |
| 296 | HC Constant | | | ASTKGPSVFPLAPSSKSTSGGTAALGCLVKD YFPEPVTVSWNSGALTSGVHTFPAVLQSS GLYSLSSVVTVPSSSLGTQTYICNVNHKPSN TKVDKKVEPKSCDKTHTCPPCPAPELLGG PSVFLFPPKPKDTLMISRTPEVTCVVVDVSH EDPEVKFNWYVDGVEVHNAKTKPREEQYN STYRVVSVLTVLHQDWLNGKEYKCKVSNKAL PAPIEKTISKAKGQPREPQVYTLPPSREE MTKNQVSLTCLVKGFYPSDIAVEWESNGQPE NNYKTTPPVLDSDGSFFLYSKLTVDKSRW QQGNVFSCSVMHEALHNHYTQKSLSLSPGK |
| 297 | LC Constant | | | RTVAAPSVFIFPPSDEQLKSGTASVVCLLNN FYPREAKVQWKVDNALQSGNSQESVTEQD SKDSTYSLSSTLTLSKADYEKHKVYACEVTH QGLSSPVTKSFNRGEC |
| 298 | Linker | | | GGGGSGGGGSGGGGS |
| 299 | murine PD-1 | | | MWVRQVPWSFTWAVLQLSWQSGWLLEVPNGP WRSLTFYPAWLTVSEGANATFTCSLSNWSED LMLNWNRLSPSNQTEKQAAFCNGLSQPVQDA RFQIIQLPNRHDFHMNILDTRRNDSGIYLCG AISLHPKAKIEESPGAELVVTERILETSTRY PSPSPKPEGRFQGMVIGIMSALVGIPVLLLL AWALAVFCSTSMSEARGAGSKDDTLKEEPSA APVPSVAYEELDFQGREKTPELPTACVHTEY ATIVFTEGLGASAMGRRGSADGLQGPRPPRH EDGHCSWPL |
| 300 | cyno PD-1 | | | MWVRQVPWSFTWAVLQLSWQSGWLLEVPNGP WRSLTFYPAWLTVSEGANATFTCSLSNWSED LMLNWNRLSPSNQTEKQAAFCNGLSQPVQDA RFQIIQLPNRHDFHMNILDTRRNDSGIYLCG AISLHPKAKIEESPGAELVVTERILETSTRY PSPSPKPEGRFQGMVIGIMSALVGIPVLLLL AWALAVFCSTSMSEARGAGSKDDTLKEEPSA APVPSVAYEELDFQGREKTPELPTACVHTEY ATIVFTEGLGASAMGRRGSADGLQGPRPPRH EDGHCSWPL |
| 301 | Linker | | | AAGSDQEPK |
| 302 | h1E9-4 & h1E9-5 | HC-FlagHis | | MEVQLVESGGGLVQPGGSLRLSCAASGFTFS TFGMSWVRQAPGKGLEWVATISGGGSDTYYP DSVQGRFTISRDNAKNSL YLQMNSLRAEDTAVYYCARQGYDVYSWFAYW GQGTLVTVSSASTKGPSVFPLAPSSKSTSGG TAALGCLVKDYFPEPVTV SWNSGALTSGVHTFPAVLQSSGLYSLSSVVT VPSSSLGTQTYICNVNHKPSNTKVDKKVEPK SCDKTHTCPPCPAPELLG GPSVFLFPPKPKDTLMISRTPEVTCVVVDVS HEDPEVKFNWYVDGVEVHNAKTKPREEQYNS TYRVVSVLTVLHQDWLNG KEYKCKVSNKALPAPIEKTISKAKGQPREPQ VYTLPPSREEMTKNQVSLTCLVKGFYPSDIA VEWESNGQPENNYKTTPP |

TABLE 10-continued

Sequences.

| SEQ ID NO | Molecule | Region | Scheme | Sequence |
|---|---|---|---|---|
| | | | | VLDSDGSFFLYSKLTVDKSRWQQGNVFSCSV MHEALHNHYTQKSLSLSPGKGSGDYKDDDDK GSGHHHHHH |
| 303 | h1E9-5 | LC | | MEIVLTQSPATLSLSPGERATLSCRASESVD NSGISFMSWYQQKPGQAPRLLIYTASNQGSG IPARFSGSGSGTDFTLTI SSLEPEDFAVYYCQQSKEVPWTFGQGTKVEI KRTVAAPSVFIFPPSDEQLKSGTASVVCLLN NFYPREAKVQWKVDNALQ SGNSQESVTEQDSKDSTYSLSSTLTLSKADY EKHKVYACEVTHQGLSSPVTKSFNRGEC |
| 304 | h1E9-4 | LC | | MDIQLTQSPSFLSASVGDRVTITCRASESVD NSGISFMSWYQQKPGKAPKLLIYTASNQGSG VPSRFSGSGSGTEFTLTI SSLQPEDFATYYCQQSKEVPWTFGQGTKVEI KRTVAAPSVFIFPPSDEQLKSGTASVVCLLN NFYPREAKVQWKVDNALQ SGNSQESVTEQDSKDSTYSLSSTLTLSKADY EKHKVYACEVTHQGLSSPVTKSFNRGEC |
| 305 | PD1-F2v-scFvFcFlag His | scFv-Fc | | MGAHSEVQLVQSGGGVVQPGRSLRLSCAASG FTFSSYWMSWVRQAPGKGLEWVSAISGSGGS TYYADSVKGRFTISRDNS KNTLYLQMNSLRAEDTAVYYCAKENWGSYFD LWGQGTTVTVSSGGGGSGGGGSGGGGSGVHS DIVMTQSPSTLSASVGDR VTITCRASQGISSWLAWYQQKPGRAPKVLIY KASTLESGVPSRFSGSGSGTDFTLTISSLQP EDFATYYCQQSYSTPWTF GQGTKLEIKAAGSDQEPKSSDKTHTCPPCSA PELLGGSSVFLFPPKPKDTLMISRTPEVTCV VVDVSHEDPEVKFNWYVD GVEVHNAKTKPREEQYNSTYRVVSVLTVLHQ DWLNGKEYKCKVSNKALPAPIEKTISKAKGQ PREPQVYTLPPSRDELTK NQVSLTCLVKGFYPSDIAVEWESNGQPENNY KTTPPVLDSDGSFFLYSKLTVDKSRWQQGNV FSCSVMHEALHNHYTQKS LSLSPGKGSGDYKDDDDKGSGHHHHHH |
| 306 | PD1-F2v | VH | | EVQLVQSGGGVVQPGRSLRLSCAASGFTFSS YWMSWVRQAPGKGLEWVSAISG SGGSTYYADSVKGRFTISRDNSKNTLYLQMN SLRAEDTAVYYCAKENWGSYFDLWGQGTT VTVSS |
| 307 | PD1-F2v | HC | | GAHSEVQLVQSGGGVVQPGRSLRLSCAASGF TFSSYWMSWVRQAPGKGLEWVSAISGSGGST YYADSVKGRFTISRDNSKNTLYLQMNSLRAE DTAVYYCAKENWGSYFDLWGQGTTVTVSSAS TKGPSVFPLAPSSKSTSGGTAALGCLVKDYF PEPVTVSWNSGALTSGVHTFPAVLQSSGLYS LSSVVTVPSSSLGTQTYICNVNHKPSNTKVD KKVEPKSCDKTHTCPPCPAPELLGGPSVFLF PPKPKDTLMISRTPEVTCVVVDVSHEDPEVK FNWYVDGVEVHNAKTKPREEQYNSTYRVVSV LTVLHQDWLNGKEYKCKVSNKALPAPIEKTI SKAKGQPREPQVYTLPPSREEMTKNQVSLTC LVKGFYPSDIAVEWESNGQPENNYKTTPPVL DSDGSFFLYSKLTVDKSRWQQGNVFSCSVMH EALHNHYTQKSLSLPGK |
| 308 | PD1-F2v | LC | | GVHSDIVMTQSPSTLSASVGDRVTITCRASQ GISSWLAWYQQKPGRAPKVLIYKASTLESGV PSRFSGSGSGTDFTLTISSLQPEDFATYYCQ QSYSTPWTFGQGTKLEIKRHMTVAAPSVFIF PPSDEQLKSGTASVVCLLNNFYPREAKVQWK VDNALQSGNSQESVTEQDSKDSTYSLSSTLT LSKADYEKHKVYACEVTHQGLSSPVTKSFNR GEC |

TABLE 10-continued

Sequences.

| SEQ ID NO | Molecule | Region | Scheme | Sequence |
|---|---|---|---|---|
| 309 | 1353-E07-R5 | CDR-H3 | | DAEYRLGSGY |
| 310 | 1353-A09-R5 | CDR-H3 | | DSEYRSGSGY |
| 311 | 1353-F09-R5 | CDR-H3 | | DAEYRSGSGY |
| 312 | 1353-G08-R5 | CDR-H3 | | DADYRSGSGY |
| 313 | 1353-G10-R5 | CDR-H3 | | DVDYRTGSGY |
| 314 | 1353-C07-R5 | CDR-H3 | | DVDYRSGSGY |
| 315 | 1353-H08-R5 | CDR-H3 | | DVDYRSGSGY |
| 316 | 1353-E07-R5 | VH | | EVQLVQSGAEVKKPGASVKVSCKASGYRFET YGISWVRQAPGQGLEWMGWISAYNGNTN YAQKLQGRVTMTTDTSTNTAYMELRSLRSDD TAVYYCARDAEYRLGSGYWGQGTLVTVSS |
| 317 | 1353-A09-R5 | VH | | EVQLVQSGAEVKKPGASVKVSCKASGYRFTW YGISWVRQAPGQGLEWMGWISAYNGNTN YAQKLQGRVTMTTDTSTNTAYMELRSLRSDD TAVYYCARDSEYRSGSGYWGQGTLVTVSS |
| 318 | 1353-F09-R5 | VH | | EVQLVQSGAEVKKPGASVKVSCKASGYRFRQ YGISWVRQAPGQGLEWMGWISAYNGNTN YAQKLQGRVTMTTDTSTNTAYMELRSLRSDD TAVYYCARDAEYRSGSGYWGQGTLVTVSS |
| 319 | 1353-G08-R5 | VH | | EVQLVQSGAEVKKPGASVKVSCKASGYRFTR YGISWVRQAPGQGLEWMGWVSAHNGNTN YAQKLQGRVTMTTDTSTNTAYMELRSLRSDD TAVYYCARDADYRSGSGYWGQGTLVTVSS |
| 320 | 1353-G10-R5 | VH | | EVQLVQSGAEVKKPGASVKVSCKASGYRFPH YGISWVRQAPGQGLEWMGWISAYNGNTN YAQKLQGRVTMTTDTSTNTAYMELRSLRSDD TAVYYCARDVDYRTGSGYWGQGTLVTVSS |
| 321 | 1353-C07-R5 | VH | | EVQLVQSGAEVKKPGASVKVSCKASGYRFST FGISWVRQAPGQGLEWMGWISAYNGNTN YAQKLQGRVTMTTDTSTNTAYMELRSLRSDD TAVYYCARDVDYRSGSGYWGQGTLVTVSS |
| 322 | 1353-H08-R5 | VH | | EVQLVQSGAEVKKPGASVKVSCKASGYRFTR QGISWVRQAPGQGLEWMGWISAYNGNTK YAQKLQGRVTMTTDTSTNTAYMELRSLRSDD TAVYYCARDVDYRSGSGYWGQGTLVTVSS |
| 323 | 1353-H09-R5 | VH | | EVQLVQSGAEVKKPGASVKVSCKASGYRFPH YGISWVRQAPGQGLEWMGWISAYNGNTN YAQKLQGRVTMTTDTSTNTAYMELRSLRSDD TAVYYCARDAEYRSGSGYWGQGTLVTVSS |
| 324 | H1E9-HC3 | HC-FlagHis | | MEVQLVESGGGLVQPGGSLRLSCAASGFTFS TFGMSWVRQAPGKGLEWVATISGGGSDTYYP DSVKGRFTISRDNAKNSLYLQMNSLRAEDTA VYYCARQGYDVYSWFAYWGQGTLVTVSSAST KGPSVFPLAPSSKSTSGGTAALGCLVKDYFP EPVTVSWNSGALTSGVHTFPAVLQSSGLYSL SSVVTVPSSSLGTQTYICNVNHKPSNTKVDK KVEPKSCDKTHTCPPCPAPELLGGPSVFLFP PKPKDTLMISRTPEVTCVVVDVSHEDPEVKF NWYVDGVEVHNAKTKPREEQYNSTYRVVSVL TVLHQDWLNGKEYKCKVSNKALPAPIEKTIS KAKGQPREPQVYTLPPSREEMTKNQVSLTCL |

TABLE 10-continued

Sequences.

| SEQ ID NO | Molecule | Region | Scheme | Sequence |
|---|---|---|---|---|
| | | | | VKGFYPSDIAVEWESNGQPENNYKTTPPVLD SDGSFFLYSKLTVDKSRWQQGNVFSCSVMHE ALHNHYTQKSLSLSPGKGSGDYKDDDDKGSG HHHHHH |
| 325 | H1E9-HC2 | HC- FlagHis | | MQVQLVESGGGVVQPGRSLRLSCAASGFTFS TFGMSWVRQAPGKGLEWVATISGGGSDTYYP DSVKGRFTISRDNSKNTLYLQMNSLRAEDTA VYYCARQGYDVYSWFAYWGQGTLVTVSSAST KGPSVFPLAPSSKSTSGGTAALGCLVKDYFP EPVTVSWNSGALTSGVHTFPAVLQSSGLYSL SSVVTVPSSSLGTQTYICNVNHKPSNTKVDK KVEPKSCDKTHTCPPCPAPELLGGPSVFLFP PKPKDTLMISRTPEVTCVVVDVSHEDPEVKF NWYVDGVEVHNAKTKPREEQYNSTYRVVSVL TVLHQDWLNGKEYKCKVSNKALPAPIEKTIS KAKGQPREPQVYTLPPSREEMTKNQVSLTCL VKGFYPSDIAVEWESNGQPENNYKTTPPVLD SDGSFFLYSKLTVDKSRWQQGNVFSCSVMHE ALHNHYTQKSLSLSPGKGSGDYKDDDDKGSG HHHHHH |
| 326 | H1E9-HC1 | HC- FlagHis | | MEVQLLESGGGLVQPGGSLRLSCAASGFTFS TFGMSWVRQAPGKGLEWVATISGGGSDTYYP DSVKGRFTISRDNSKNTLYLQMNSLRAEDTA VYYCARQGYDVYSWFAYWGQGTLVTVSSAST KGPSVFPLAPSSKSTSGGTAALGCLVKDYFP EPVTVSWNSGALTSGVHTFPAVLQSSGLYSL SSVVTVPSSSLGTQTYICNVNHKPSNTKVDK KVEPKSCDKTHTCPPCPAPELLGGPSVFLFP PKPKDTLMISRTPEVTCVVVDVSHEDPEVKF NWYVDGVEVHNAKTKPREEQYNSTYRVVSVL TVLHQDWLNGKEYKCKVSNKALPAPIEKTIS KAKGQPREPQVYTLPPSREEMTKNQVSLTCL VKGFYPSDIAVEWESNGQPENNYKTTPPVLD SDGSFFLYSKLTVDKSRWQQGNVFSCSVMHE ALHNHYTQKSLSLSPGKGSGDYKDDDDKGSG HHHHHH |
| 327 | H1E9-LC4 | LC | | MDIVLTQSPDSLAVSLGERATINCRASESVD NSGISFMSWYQQKPGQPPKLLIYTASNQGSG VPDRFSGSGSGTDFTLTISSLQAEDVAVYYC QQSKEVPWTFGQGTKVEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG EC |
| 328 | H1E9-LC3 | LC | | MEIVLTQSPGTLSLSPGERATLSCRASESVD NSGISFMSWYQQKPGQAPRLLIYTASNQGSG IPDRFSGSGSGTDFTLTISRLEPEDFAVYYC QQSKEVPWTFGQGTKVEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG EC |
| 329 | H1E9-LC2 | LC | | MDIVLTQSPLSLPVTPGEPASISCRASESVD NSGISFMSWYLQKPGQSPQLLIYTASNQGSG VPDRFSGSGSGTDFTLKISRVEAEDVGVYYC QQSKEVPWTFGQGTKVEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG EC |
| 330 | H1E9-LC1 | LC | | MDIQLTQSPSSLSASVGDRVTITCRASESVD NSGISFMSWYQQKPGKAPKLLIYTASNQGSG VPSRFSGSGSGTDFTFTISSLQPEDIATYYC QQSKEVPWTFGQGTKVEIKRTVAAPSVFIFP PSDEQLKSGTASVVCLLNNFYPREAKVQWKV |

TABLE 10-continued

Sequences.

| SEQ ID NO | Molecule | Region | Scheme | Sequence |
|---|---|---|---|---|
| | | | | DNALQSGNSQESVTEQDSKDSTYSLSSTLTL SKADYEKHKVYACEVTHQGLSSPVTKSFNRG EC |
| 331 | | CDR-H2 | Kabat | TISGGGSDTYYPDSVQG |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:

1. An isolated antibody that specifically binds to PD-1 comprising:
three heavy chain CDRs and three light chain CDRs comprised within a $V_H$ region of SEQ ID NO: 252 and a $V_L$ region of SEQ ID NO: 276.

2. The antibody of claim 1 that specifically binds to PD-1, wherein the antibody comprises:
m. a CDR-H1 comprising SEQ ID NO: 13; a CDR-H2 comprising SEQ ID NO: 66; a CDR-H3 comprising SEQ ID NO: 119; a CDR-L1 comprising SEQ ID NO: 148; a CDR-L2 comprising SEQ ID NO: 177; and a CDR-L3 comprising SEQ ID NO: 206;
n. a CDR-H1 comprising SEQ ID NO: 37; a CDR-H2 comprising SEQ ID NO: 90; a CDR-H3 comprising SEQ ID NO: 119; a CDR-L1 comprising SEQ ID NO: 148; a CDR-L2 comprising SEQ ID NO: 177; and a CDR-L3 comprising SEQ ID NO: 206.

3. An isolated antibody that specifically binds to PD-1, wherein the antibody comprises:
g. a $V_H$ comprising: a CDR-H1 comprising one or more of SEQ ID NOs: 13 and 37; a CDR-H2 comprising one or more of SEQ ID NOs: 66 and 90; and a CDR-H3 comprising SEQ ID NO: 119; and a $V_L$ region comprising: a CDR-L1 comprising SEQ ID NO: 148; a CDR-L2 comprising SEQ ID NO: 177; and a CDR-L3 comprising SEQ ID NO: 206.

4. The antibody of claim 3, wherein the antibody comprises a Vu region selected from:

a SEQ ID NO: 252, or a variant thereof having 4 or fewer amino acid substitutions;
wherein the substitutions are conservative amino acid substitutions.

5. The antibody of claim 3, wherein the antibody comprises a $V_L$ region selected from:
a. SEQ ID NO: 276 or a variant thereof having 20 or fewer amino acid substitutions,
wherein the substitutions are conservative amino acid substitutions.

6. The antibody of claim 3, wherein:
g. the $V_H$ region is SEQ ID NO: 252, and the $V_L$ region is SEQ ID NO: 276.

7. The antibody of claim 3, further comprising at least one constant region domain.

8. The antibody of claim 7, wherein the constant region domain comprises a sequence selected from SEQ ID NOs: 224-226 and 297.

9. The antibody of claim 3, wherein the antibody is a monoclonal antibody.

10. The antibody of claim 3, wherein the antibody is an IgA, an IgD, an IgE, an IgG, or an IgM.

11. The antibody of claim 3, wherein the antibody is aglycosylated.

12. The antibody of claim 3, wherein the antibody is an antibody fragment.

13. The antibody of claim 12, wherein the antibody fragment is selected from an Fv fragment, a Fab fragment, a F(ab')$_2$ fragment, a Fab' fragment, an scFv (sFv) fragment, and an scFv-Fc fragment.

14. The antibody of claim 13, wherein the antibody is an scFv fragment.

15. The antibody of claim 13, wherein the antibody is an scFv-Fc fragment.

16. The antibody of claim 15, wherein the scFv-Fc fragment comprises a sequence selected from SEQ ID NO: 243 with AAGSDQEPK (SEQ ID NO: 301) removed from the sequence.

17. The antibody of claim 3, wherein the antibody has a $k_a$ of about $4.74 \times 10^4$ M$^{-1}$×sec$^{-1}$ to about $1.23 \times 10^6$ M$^{-1}$×sec$^{-1}$ when associating with human PD-1 at a temperature of 25° C.

18. The antibody of claim 3, wherein the antibody has a $k_d$ of about $1.87 \times 10^{-2}$ sec$^{-1}$ to about $4.17 \times 10^{-4}$ sec$^{-1}$ when dissociating from human PD-1 at a temperature of 25° C.

19. The antibody of claim 3, wherein the antibody has a $K_D$ of about $3.85 \times 10^{-8}$ M to about $2.52 \times 10^{-10}$ M when bound to human PD-1 at a temperature of 25° C.

20. The antibody of claim 3, wherein the antibody specifically binds one or more of murine PD-1 and cynomolgus PD-1.

21. A kit comprising an antibody of claim 3, and instructions for use of the antibody.

22. A polynucleotide encoding an antibody of claim 3.

23. A vector comprising the polynucleotide of claim 22.

24. A host cell comprising the vector of claim 23.

25. A pharmaceutical composition comprising the antibody of claim 3 and a pharmaceutically acceptable carrier.

26. A method of treating a disease or condition in a subject in need thereof, comprising administering to the subject an effective amount of an antibody of claim 3, or a pharmaceutical composition of claim 25.

27. The method of claim 26, wherein the disease or condition is cancer.

28. A polynucleotide encoding an antibody of claim 1.

29. A vector comprising the polynucleotide of claim 28.

30. A host cell comprising the vector of claim 29.

31. A pharmaceutical composition comprising the antibody of claim 1 and a pharmaceutically acceptable carrier.

32. A method of treating a disease or condition in a subject in need thereof, comprising administering to the subject an effective amount of an antibody of claim 1.

33. A method of treating a disease or condition in a subject in need thereof, comprising administering to the subject an effective amount of a pharmaceutical composition of claim 31.

34. The method of claim 32, wherein the disease or condition is cancer.

35. The method of claim 33, wherein the disease or condition is cancer.

* * * * *